US006187904B1

(12) United States Patent
Broekaert et al.

(10) Patent No.: US 6,187,904 B1
(45) Date of Patent: *Feb. 13, 2001

(54) BIOCIDAL PROTEINS

(75) Inventors: Willem F. Broekaert, Dilbeek; Bruno P. A. Cammue, Alsemberg, both of (BE); Rupert W. Osborn, Middlesex; Sarah B. Rees, Berkshire, both of (GB); Franky R. G. Terras, Amzegem; Jozef Vanderleyden, Heverlee, both of (BE)

(73) Assignee: ZENECA Limited, London (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/971,982

(22) Filed: Nov. 17, 1997

Related U.S. Application Data

(60) Continuation of application No. 08/452,078, filed on May 26, 1995, now Pat. No. 5,689,043, which is a division of application No. 08/377,687, filed on Jan. 25, 1995, now Pat. No. 5,538,525, which is a continuation of application No. 08/002,480, filed on Jan. 4, 1993, now abandoned, which is a continuation of application No. PCT/GB92/01570, filed on Aug. 27, 1992, now abandoned.

(30) Foreign Application Priority Data

Aug. 29, 1991 (GB) .................................................. 9118523
Feb. 13, 1992 (GB) .................................................. 9203038
Jun. 25, 1992 (GB) .................................................. 9213526

(51) Int. Cl.[7] .................................................. C07K 14/00
(52) U.S. Cl. .................... 530/324; 530/326; 530/350; 514/12; 514/13
(58) Field of Search ...................... 514/12, 13; 530/324, 530/326, 350

(56) References Cited

U.S. PATENT DOCUMENTS

| 4,351,762 | 9/1982 | Verlander et al. | 260/112.5 |
|---|---|---|---|
| 4,940,840 | 7/1990 | Suslow et al. | 800/205 |
| 5,538,525 | * 7/1996 | Broekaert et al. | 47/58 |
| 5,689,043 | * 11/1997 | Broekaert et al. | 800/205 |

FOREIGN PATENT DOCUMENTS

| 0375091 | 6/1990 | (EP) . |
|---|---|---|
| 9011770 | 10/1990 | (WO) . |

OTHER PUBLICATIONS

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA. pp. 491–495, 1994.*

J.A. Parsons, 'Peptide Hormones', published 1976 by University Park Press (Baltimore), pp. 1–7.J.A Parsons, 'Peptide Hormones', published 1976 by University Park Press (Baltimore), pp. 1–7.*

Fernandez de Caleya et al (1972) Chemical Abstracts, vol. 77, abstract No. 70756.

Jones et al (1982) Chemical Abstracts, vol. 97, abstract No. 108755.

Garcia–Olmeda, "Trypsin/alpha–amylase Inhibitors and thionins from cereals: possible role in crop protection," J. Exp. Bot., 238 Supplement, Meeting Held Apr. 7–12, 1991, vol. 42, p. 4.

Bohlman et al (1988) "Leaf–specific thionins of barley— a novel class of cell wall proeins toxic to plant–pathogenic fungi and possibly involved in the defence mechanism of plants," EMBO Journal, vol. 7, No. 6, 1559–1565.

Terras et al (1992) "Analysis of Two Novel Classes of Plant Antifungal Proteins from Radish (*Radphanus sativus L.*) Seeds," The Journal of Chemistry, vol. 267, No. 22, pp. 15301–15309.

Chiang et al (1991) Molec Plant–Microbe Int. 4(4) 324–331 revd PTO Jun. 8, 1991.

Florack et al (1990) Agric. Biotechnol. In Focus in the Netherlands, pp. 39–48, Centre for AGric. Publ., Wageningen, Netherlands.

Mauch et al (1991) Plant Mold Biol 16:1089–1091.

Block et al (1991) FEBS Lett. 279 (1):101–104.

Pratt et al (1990) Plant Physiol 93: 1453–1459.

Ishibashi et al (1990) Plant Mol. Biol. 15:59–64.

Kusul et al (1991) J. Biochem. 109:899–903.

Ohguchi et al, Biol. Abst. BR 41:2924.

* cited by examiner

*Primary Examiner*—Christopher S. F. Low
*Assistant Examiner*—Anish Gupta
(74) *Attorney, Agent, or Firm*—Liza D. Hohenschutz

(57) ABSTRACT

Biocidal proteins isolated from seeds have been characterised, in particular proteins isolated from members of the Brassicaceae, Compositae and Leguminosae families including Raphanus, Brassica, Sinapis, Arabidopsis, Dahlia, Cnicus, Lathyrus and Clitoria. The proteins show a wide range of antifungal activity and some are active against Gram-positive bacteria. All share a common amino acid sequence. DNA encoding the proteins has been isolated and incorporated into vectors. Plants transformed with this DNA may be produced. The proteins find commercial application as antifungal or antibacterial agents; transformed plants will show increased disease-resistance.

2 Claims, 39 Drawing Sheets

IEC on S-Sepharose

IEC on S-Sepharose

IEC on S-SEPHAROSE

IEC on S-SEPHAROSE

```
Rs-AFP1  (Q) K L C E R P S G T W S G V C G N N
Rs-AFP2  (Q) K L C Q R P S G T W S G V C G N N
             N A C K N Q C I N L E K A R H G S C N Y V F P A H K
             N A C K N Q C I R L E K A R H G S C

Br-AFP1  . . . . . . . . . . . . . . . . . . . . . . . . . . . . . . . . . . . . . . . . . . .
Br-AFP2  . . . . . . . . . . . . . . . . . . . . . . . . . . . . . . . . . . . . . . . . . . R
Bn-AFP1  . . . . . . . . . . . . . . . . . . . . . . . ? . . . . . . . . . . . . . . . . . . .
Bn-AFP2  . . . . . . . . . . . . . . . . . . . . . . . . . . . . . . . . . . . . . . . . . . .
Sa-AFP1  . . . . . . . . . . . . . . . . . . . . . . . . . . . . . . . . . . . . . . . . . . .
Sa-AFP2  . . . . . . . . . . . . . . . . . . . . . Q . . . . . . . . . . . . . . . . R . . . .
At-AFP1  . . . . . . . . . . . . . . . . . . . . . . . . . . . . . . . . . S . . . . . . . . .
```

FIG. 21

| | | | |
|---|---|---|---|
| Dm-AMP1 | ELCEKASKTWSGNCGNTGHCDN | QCKSWEGAAHGACHVRNGKHMCFCYFNC | |
| Dm-AMP2 | EVCEKASKTWSGNCGNTGHC | | |
| Cb-AMP1 | ELCEKASKTWSGNCGNTKHCDD | QCKSWEGAAHGACHVRSGKHMCFCYFNC | |
| Cb-AMP2 | ELCEKASKTWSGNCGNTKHCDN | KCKSWEGAAHGACHVRSGKHMCFCYFNC | |

FIG. 22

```
Lc-AFP   KTCENLSGTFKGPCIPDGNCNKHCKN
Ct-AMP1  NLCERASLTWTGNCGNTGHCDTQCRN

NEHLLSGRCRDDF?--CWCTRNC
         WESAKHGACHKRGNWKCFCYFDC
```

FIG. 23

| | | | | | | | | | | | | | | | | |
|---|---|---|---|---|---|---|---|---|---|---|---|---|---|---|---|---|
| Rs-AFP1 (Q) | K | L | C | E | R | P | S | G | T | W | S | G | V | C | G | N | N | N | A | C |
| Dm-AMP1 | E | L | C | E | K | A | S | K | T | W | S | G | N | C | G | N | T | G | H | C |
| Cb-AMP1 | E | L | C | E | K | A | S | K | T | W | S | G | N | C | G | N | T | K | H | C |
| Cb-AMP2 | E | L | C | E | K | A | S | K | T | W | S | G | N | C | G | N | T | K | H | C |
| Lc-AFP | K | T | C | E | N | L | S | G | T | F | K | G | P | C | I | P | D | G | N | C |
| Ct-AMP1 | N | L | C | E | R | A | S | L | T | W | T | G | N | C | G | N | T | G | H | C |
| pI230 | N | T | C | E | N | L | A | G | S | Y | K | G | V | C | F | G | G | - | - | C |
| pI39 | N | T | C | E | H | L | A | D | T | Y | R | G | V | C | F | T | N | A | S | C |
| pSAS10 | K | T | C | E | L | N | A | D | T | Y | R | G | P | C | F | T | T | G | S | C |
| pI322 | R | H | C | E | S | L | S | H | R | F | K | G | P | C | T | R | D | S | N | C |
| SIα2 | R | V | C | M | G | K | S | A | G | F | K | G | L | C | M | R | D | Q | N | C |
| γ1pur | K | I | C | R | R | R | S | A | G | F | K | G | P | C | M | S | N | K | N | C |

| | | | | | | | | | |
|---|---|---|---|---|---|---|---|---|---|
| Dm-AMP1 | GAG | CTT | TGC | GAG | AAG | GCT | TCT | AAG | ACT | TGG | TCT | GGA | AAC |
| | TGG | GAG | GGA | GCT | GCT | CAT | GGA | GCT | TGC | CAT | GTT | AGA | AAC |
| Dm-AMP2 | GAG | GTT | TGC | GAG | AAG | GCT | TCT | AAG | ACT | TGG | TCT | GGA | AAC |
| Cb-AMP1 | GAG | CTT | TGC | GAG | AAG | GCT | TCT | AAG | ACT | TGG | TCT | GGA | AAC |
| | TGG | GAG | GGA | GCT | GCT | CAT | GGA | GCT | TGC | CAT | GTT | AGA | AAC |
| Cb-AMP2 | GAG | CTT | TGC | GAG | AAG | GCT | TCT | AAG | ACT | TGG | TCT | GGA | AAC |
| | TGG | GAG | GGA | GCT | GCT | CAT | GGA | GCT | TGC | CAT | GTT | AGA | TCT |

FIG. 25A-1

TGC GGA AAC ACT GGA CAT TGC GAT AAC CAA TGC AAG TCT

GGA AAG CAT ATG TGC TTC TGC TAC TTC AAC TGC

TGC GGA AAC ACT GGA CAT TGC ... ... ...

TGC GGA AAC ACT AAG CAT TGC GAT GAT CAA TGC AAG TCT

GGA AAG CAT ATG TGC TTC TGC TAC TTC AAC TGC

TGC GGA AAC ACT AAG CAT TGC GAT AAC AAG TGC AAG TCT

GGA AAG CAT ATG TGC TTC TGC TAC TTC AAC TGC

FIG. 25A-2

```
Lc-AFP    AAG ACT TGC GAG AAC CTT TCT GGA ACT TTC AAG GGA CCA
          AAC GAG CAT CTT CTT TCT GGA AGA TGC AGA GAT GAT TTC

Ct-AMP1   AAC CTT TGC GAG AGA GCT TCT CTT ACT TGG ACT GGA AAC
          TGG GAG TCT GCT AAG CAT GGA GCT TGC CAT AAG AGA GGA
          TGC ATT CCA GAT GGA AAC AAC AAG CAT TGC AAG AAC
          ??? TGC TGG TGC ACT AGA AAC TGC
          TGC GGA AAC ACT GGA CAT TGC GAT ACT CAA TGC AGA AAC
          AAC TGG AAG TGC TTC TGC TAC TTC GAT TGC
```

FIG. 25B

Rs-nsLTP  A L S C G T V N S N L A A C I G Y L T Q
          N A P L A R G C C T G V T N L N N M A ? T T P

FIG. 26

|        |   |   |   |   |   |   |   |   |   |   |   |   |   |   |   |
|--------|---|---|---|---|---|---|---|---|---|---|---|---|---|---|---|
| Rs-nsLTP | A | L | S | C | G | T | V | N | S | N | L | A | A | C | I | G | Y | L | T | Q |
| So-nsLTP | G | I | T | C | G | M | V | S | S | K | L | A | P | C | I | G | Y | L | K | G |
| Rc-nsLTP | V | D |   | C | G | Q | V | N | S | S | L | A | P | C | I | P | F | L | T | G |
| Dc-nsLTP | V | L | T | C | G | Q | V | T | G | A | L | A | P | C | L | G | Y | L | R | S |
| Hv-nsLTP | A | L | N | C | G | Q | V | D | S | K | N | P | C | L | T | Y | V | Q | G |
| Zm-nsLTP | A | I | S | C | G | Q | V | A | S | A | I | A | P | C | I | S | Y | A | R | G |

```
GTTTTATTAGTGATCATGGCTAAGTTTGCGTCCATCATCGCACTT              45
                 M  A  K  F  A  S  I  I  A  L

CTTTTTGCTGCTCTTGTTCTTTTTGCTGCTTTCGAAGCACCAACA              90
 L  F  A  A  L  V  L  F  A  A  F  E  A  E  T

ATGGTGGAAGCACAGAAGTTGTGCGAAAGGCCAAGTGGGACATGG             135
 M  V  E  A  Q  K  L  C  E  R  P  S  G  T  W

TCAGGAGTCTGTGTGGGAAAACAATAACGCAAGAATCAGTGCATT             180
 S  G  V  C  G  N  N  N  A  K  N  Q  C  I

AACCTTGAGAAAGCACGACATGGATCTTGCAACTATGTCTTCCCA             225
 N  L  E  K  A  R  H  G  S  C  N  Y  V  F  P

GCTCACAAGTGTATCTGCTACTTTCCTTGTAATTTATCGCAAAC              270
 A  H  K  C  I  C  Y  F  P  C  *

TCTTTGGTGAATAGTTTTTATGTAATTTACACAAAATAAGTCAGT             315

GTCACTATCCATGAGTGATTTTAAGACATGTACCAGATATGTTAT             360

GTTGGTTCGGTTATACAAATAAAGTTTTATTCACCAAAAAAAAAA             405

AAAAAAAAA                                                 414
```

FIG. 29

```
GGAAATAATAACGCATGCAAGAATCAGTGCATTCGACTTGAGAAA      45
 G  N  N  N  A  C  K  N  Q  C  I  R  L  E  K

GCACGACATGGGTCTTGCAACTATGTCTTCCCAGCTCACAAGTGT      90
 A  R  H  G  S  C  N  Y  V  F  P  A  H  K  C

ATCTGTTATTTCCCTTGTTAATTCCATAAACTCTTCGGTGGTTAA     135
 I  C  Y  F  P  C  *

TAGTGTGGCATATTACATATAATTAATAAGTTTGTGTCACTATT      180

TATTAGTGACTTTATGACATGTGCCAGGTATGTTTATGTTGGGTT     225

GGTTGTAATATATAAAAAAGTTCACGGATAATAAGATGATAAGCTCA   270

CGTCGCCAAAAAAA                                    284
```

FIG. 30

CCCCGGGCTGCAG

GAATTCGGGCCGC

```
         10        20        30        40        50        60
          |         |         |         |         |         |
GTTTATTAGTGATCATGGCTAAGTTTGCGTCCATCATCGCACTTCTTTTTGCTGCTCTT
                  M  A  K  F  A  S  I  I  A  L  L  F  A  A  L 70        80        90       100       110       120
          |         |         |         |         |         |
GTTCTTTTTGCTGCTTTCGAAGCACCAACAATGGTGGAAGCACAGAAGTTGTGCCAAAGG
 V  L  F  A  A  F  E  A  P  T  M  V  E  A  Q  K  L  C  Q  R
```

FIG. 31-1

```
          130         140         150         160         170         180
           |           |           |           |           |           |
CCAAGTGGACATGGTTCAGGAGTCTGTGGAAACAATAACGCATGCAAGAATCAGTGCATT
| P  S  G  T  W  S  G  V  C  G  N  N  N  A  C  K  N  Q  C  I |

190         200         210         220         230         240
           |           |           |           |           |           |
AGACTTGAGAAAGCACGACATGGATCTTGCAACTATGTCTTCCCAGCTCACAAGTGTATC
| R  L  E  K  A  R  H  G  S  C  N  Y  V  F  P  A  H  K  C  I |

250         260
                       |           |
TGCTACTTTCCTTGTTAATAG
| C  Y  F  P  - - |
```

FIG. 31-2

BIOCIDAL PROTEINS

This is a continuation of application Ser. No. 08/452,078, filed May 26, 1995 now U.S. Pat. No. 5,689,043, which is a Division of application Ser. No. 08/377,687, filed Jan. 25, 1995, U.S. Pat. No. 5,538,525, which is a Continuation of application Ser. No. 08/002,480, filed Jan. 4, 1993, now abandoned, which is a Continuation of PCT/GB92/01570, filed Aug. 27, 1992, now abandoned.

This invention relates to biocidal proteins, processes for their manufacture and use, and DNA sequences coding for them. In particular, it relates to antimicrobial proteins isolated from seeds such as those of members of the Brassicaceae, Compositae or Leguminosae families.

In this context, antimicrobial proteins are defined as proteins possessing at least one of the following activities: antifungal activity (which may include anti-yeast activity); antibacterial activity. Activity includes a range of antagonistic effects such as partial inhibition or death.

The Brassicaceae is a large family of herbs and shrubs which grow widely in tropical, sub-tropical and temperate regions. The Family Brassicaceae is also known as the "Cruciferae". *Raphanus sativus* (radish) belongs to this family and is cultivated widely as a vegetable.

Dahlia belongs to the Compositae and has been extensively cultivated as an ornamental garden plant. A number of hybrids are commercially available, belonging to the *Dahlia merckii* or *Dahlia variablis* species. *Cnicus benedictus*, another Compositae, is a native plant of the Mediterranean regions and was once used as a tonic and a cure for gout.

Lathyrus and Clitoria belong to the Leguminosae family. Lathyrus has been extensively cultivated as an ornamental garden plant, the most widely known being the sweet pea plant, Lathyrus odoratus. The genus Clitoria is less well known to European gardeners; *Clitoria ternatea* was originally introduced from the East Indies in the 1800s.

Although plants normally grow on substrates that are extremely rich in fungal organisms, infection remains a rare event. To keep out potential invaders, plants produce a wide array of antifungal compounds, either in a constitutive or an inducible manner. The best studied of these are phytoalexins which are secondary metabolites with a broad antimicrobial activity spectrum that are specifically synthesised upon perception of appropriate defence-related signal molecules. The production of phytoalexins depends on the transcriptional activation of a series of genes encoding enzymes of the phytoalexin biosynthetic pathway. During the last decade, however, it has become increasingly clear that some plant proteins can play a more direct role in the control of phytopathogenic fungi. Several classes of proteins with antifungal properties have now been identified, including chitinases, beta-1,3-glucanases, chitin-binding lectins, zeamatins, thionins and ribosome-inactivating proteins.

These proteins have gained considerable attention as they could potentially be used as biocontrol agents. The chitinases and beta-1,3-glucanases have weak activities by themselves, and are only inhibitory to plant pathogens when applied in combination (Mauch et al, 1988, Plant Physiol, 88, 936–942). The chitin-binding lectins can also be classified as rather weak antifungal factors (Broekaert et al, 1989, Science, 245, 1100–1102; Van Parijs et al, 1991, Planta, 183, 258–264). Zeamatin is a more potent antifungal protein but its activity is strongly reduced by the presence of ions at physiological concentrations (Roberts and Selitnermikoff, 1990, G Gen Microbiol, 136, 2150–2155). Finally, thionins and ribosome-inactivating proteins are potentially hazardous since they are known to be toxic for human cells (Carrasco et al, 1981, Eur J Biochem, 116, 185–189; Vernon et al, 1985, Arch Biochem Biophys, 238, 18–29; Stirpe and Barbieri, 1986, FEBS Lett, 195, 1–8).

We have now purified a new class of potent antimicrobial proteins with broad spectrum activity against plant pathogenic fungi and with some antibacterial activity, moderate sensitivity to ions and apparent low toxicity for cultured human cells.

According to the present invention, we provide antimicrobial proteins capable of being isolated from seeds and in particular from members of the Brassicaceae, the Compositae or the Leguminosae families including Raphanus, Brassica, Sinapis, Arabidopsis, Dahlia, Cnicus, Lathyrus or Clitoria.

In further aspects, this invention comprises a vector containing a DNA sequence coding for a protein according to the invention. The DNA may be cloned or transformed into a biological system allowing expression of the encoded protein.

The invention also comprises plants transformed with recombinant DNA encoding an antimicrobial protein according to the invention.

The invention also comprises a process of combating fungi or bacteria whereby they are exposed to the proteins according to the invention.

A new class of potent antimicrobial proteins has been isolated from seeds of the Brassicaceae, the Compositae, and the Leguminosae. Similar proteins may be found in other plant families, genera and species. The class includes proteins which share a common amino acid sequence and which show activity against a range of plant pathogenic fungi.

The antimicrobial proteins isolated from seeds of *Raphanus sativus* (radish) include two protein factors, hereafter called Rs-AFP1 (*Raphanus sativus*—Antifungal Protein 1) and Rs-AFP2 (*Raphanus sativus*—Antifungal Protein 2) respectively. Both are oligomeric proteins, composed of identical 5 kDa subunits. Both proteins are highly basic and have pI values above 10. Similar antifungal proteins have been isolated from other Brassicaceae, including *Brassica napus* (Bn-AFPs), *Brassica rapa* (Br-AFPs), *Sinapis alba* (Sa-AFPs) and *Arabidopsis thaliana* (At-AFP1).

The antimicrobial proteins isolated from seeds of Dahlia and Cnicus include four protein factors, hereafter called Dm-AMP1 (*Dahlia merckii*—Antimicrobial Protein 1), Dm-AMP2 (*Dahlia merckii*—Antimicrobial Protein 2), Cb-AMP1 (*Cnicus benedictus*—Antimicrobial Protein 1) and Cb-AMP2 (*Cnicus benedictus*—Antimicrobial Protein 2) respectively. The Dm-AMP proteins may be isolated from seed of the Dahlia genus. The Cb-AMP proteins may be isolated from seed of the Cnicus genus. All four proteins are closely related and are composed of 5 kDa subunits arranged as oligomeric structures. All four proteins are highly basic.

The antimicrobial proteins isolated from seeds of Lathyrus and Clitoria include three protein factors, hereafter called Lc-AFP (*Lathyrus cicera*—Antifungal Protein), Ct-AMP1 (*Clitoria ternatea*—Antimicrobial Protein 1) and Ct-AMP2 (*Clitoria ternatea*—Antimicrobial Protein 2) respectively. Lc-AFP may be isolated from seed of the Lathyrus genus. The Ct-AMP proteins may be isolated from seed of the Clitoria genus. All three proteins are composed of 5 kDa subunits arranged as oligomeric structures and are highly basic.

N-terminal amino acid sequence determination has shown that the above proteins isolated from the Brassicaceae, Compositae and Leguminosae are closely related and can be classified as a single protein family. Between the different plant families, the protein sequences are approximately 50% identical. These sequences enable manufacture of the proteins by chemical synthesis using a standard peptide synthesiser.

The antimicrobial proteins are partially homologous to the predicted protein products of the Fusarium-induced genes pI39 and pI230 in pea (*Pisum sativum*—a member of the Leguminosae family) as described by Chiang and Hadwiger, 1991 (Mol Plant Microbe Interact, 4, 324–331). This homology is shared with the predicted protein product of the pSAS10 gene from cowpea (*Vigna unguiculata*—another legume) as described by Ishibashi et al (Plant Mol Biol, 1990, 15, 59–64). The antimicrobial proteins are also partially homologous with the predicted protein product of gene pI322 in potato (*Solanum tuberosum*—a member of the Solanaceae family) as described by Stiekema et al, 1988 (Plant Mol Biol, 11, 255–269). Nothing is known about the biological properties of the proteins encoded by genes pI39, pI230, pSAS10 or pI322 as only the cDNA has been studied. However, the pI39, pI230 and pI322 genes are switched on after challenge to the plant by a disease or other stress. It has been proposed that the pSAS10 gene encodes a protein involved in germination. Due to their sequence similarity with the antimicrobial proteins of the invention, the proteins encoded by the pI39, pI230, pSAS10 or pI322 genes may be useful as fungicides or as antibiotics.

The antimicrobial protein sequences show a lower degree of partial homology with the sequences of a group of small α-amylase inhibitors found in the following members of the Gramineae: sorghum (Bloch and Richardson, 1991, FEBS Lett, 279:101–104), wheat (Colitta et al, 1990, FEBS Lett, 270:191–194) and barley (Mendez et al, 1990 Eur J Biochem, 194:533–539). Such proteins, including SIα2 from sorghum and γ-1-purothionin from wheat, are known to inhibit insect α-amylase and are toxic to insect larvae. It is not known if these α-amylase inhibitors show any antifungal or other antimicrobial activity: no other data on their biological activity has been reported. Due to their sequence similarity with the antimicrobial proteins of the invention, the α-amylase inhibitor proteins may be useful as fungicides or as antibiotics.

A third antifungal protein has been isolated from radish seeds, hereafter called Rs-nsLTP (*Raphanus sativus* non-specific lipid transfer protein). It is a dimeric protein, composed of two identical 9 kDa subunits. Amino acid sequence determination has identified the 43 N-terminal residues of Rs-nsLTP, and has shown it to be homologous with non-specific lipid transfer proteins isolated from other plants (Arondel and Kader, 1990, Experientia, 46:579–585) but not with the other antimicrobial proteins discussed above. The Rs-nsLTP sequence enables manufacture of the protein by chemical synthesis using a standard peptide synthesiser.

Knowledge of their primary structure, enables the production of DNA constructs encoding the antimicrobial proteins. The DNA sequence may be predicted from the known amino acid sequence or the sequence may be isolated from plant-derived DNA libraries.

Oligonucleotide probes may be derived from the known amino acid sequence and used to screen a cDNA library for cDNA clones encoding some or all of the protein. cDNA clones encoding the Rs-AFPs have been isolated in this way and sequenced. These same oligonucleotide probes or cDNA clones may be used to isolate the actual AFP, AMP or Rs-nsLTP gene(s) by screening genomic DNA libraries. Such genomic clones may include control sequences operating in the plant genome. Thus it is also possible to isolate promoter sequences which may be used to drive expression of the antimicrobial (or other) proteins. These promoters may be particularly responsive to environmental conditions (such as the presence of a fungal pathogen).

DNA encoding the antimicrobial proteins (which may be a cDNA clone, a genomic DNA clone or DNA manufactured using a standard nucleic acid synthesiser) can then be cloned into a biological system which allows expression of the proteins. Hence the proteins can be produced in a suitable micro-organism or cultured cell, extracted and isolated for use. Suitable micro-organisms include *Escherichia coli* and *Saccharomyces cerevisiae*. The genetic material can also be cloned into a virus or bacteriophage. Suitable cells include cultured insect cells and cultured mammalian cells. The DNA can also be transformed by known methods into any plant species, so that the antimicrobial proteins are expressed within the plant.

Plant cells according to the invention may be transformed with constructs of the invention according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocot and dicot plants may be obtained in this way, although the latter are usually more easy to regenerate.

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The AFP, AMP and Rs-nsLTP proteins show a wide range of antifungal activity, including anti-yeast activity, and the AMPs are also active against Gram positive bacteria. The proteins are useful as fungicides or antibiotics. Exposure of a plant pathogen to an antimicrobial protein may be achieved by application of the protein to plant parts using standard agricultural techniques (eg spraying). The proteins may also be used to combat fungal or bacterial disease by expression within plant bodies.

All the antimicrobial proteins show surprisingly high activity: they inhibit the growth of a variety of plant pathogenic fungi at submicromolar doses. Antifungal activity of the AMPs is only partially dependent on the ionic conditions. The antifungal effect of the AFPs is not affected by $K^+$ ions at physiological concentrations (50 mM). The antifungal effect of Rs-AFP1, but not Rs-AFP2, is antagonised by $Ca^{2+}$ at physiological concentrations (1 mM). Rs-nsLTP also inhibits growth of a variety of plant pathogenic fungi, but is less potent and more salt sensitive that the AFPs.

The antimicrobial proteins can be isolated and purified from appropriate seeds, synthesised artificially from their known amino acid sequence, or produced within a suitable micro-organism by expression of recombinant DNA. The proteins may also be expressed within a transgenic plant.

BRIEF DESCRIPTION OF THE DRAWINGS

The invention may be further understood by reference to the drawings, in which:

FIGS. 2B-1 and 2B-2 show the HPLC profile of purified Rs-AFP2 and Rs-nsLTP.

FIG. 21 shows the amino acid sequences of Rs-AFP1, Rs-AFP2 and the related Brassicaceae proteins.

FIG. 22 shows the amino acid sequences of the Dm-AMPs and the Cb-AMPs.

FIG. 23 shows the amino acid sequences of Lc-AFP and Ct-AMP1.

FIGS. 24-1, 24-2 and 24-3 show the alignment of the amino acid sequences of Rs-AFP1, Dm-AMP1, the Cb-AMPs, Lc-AFP, Ct-AMP1, sorghum SIα2, wheat γ1 purothionin, and the predicted products of the pea genes pI230 and pI39, of the cowpea gene pSAS10, and of the potato gene p322.

FIGS. 25A-1 and 25A-2 show predicted DNA sequences for the Dm-AMP and Cb-AMP genes.

FIG. 25B shows predicted DNA sequences for the Lc-AFP and Ct-AMP1 genes.

FIG. 26 shows the amino acid sequence of Rs-nsLTP.

FIGS. 27-1 and 27-2 show the alignment of the amino acid sequences of Rs-nsLTP and various plant non-specific lipid transfer proteins.

FIG. 29 shows the full length cDNA sequence of Rs-AFP1.

FIG. 30 shows the truncated cDNA sequence of Rs-AFP2.

FIGS. 31-1 and 31-2 show the full length DNA sequence of PCR assisted site directed mutagenesis of Rs-AFP2.

Figure 1A:
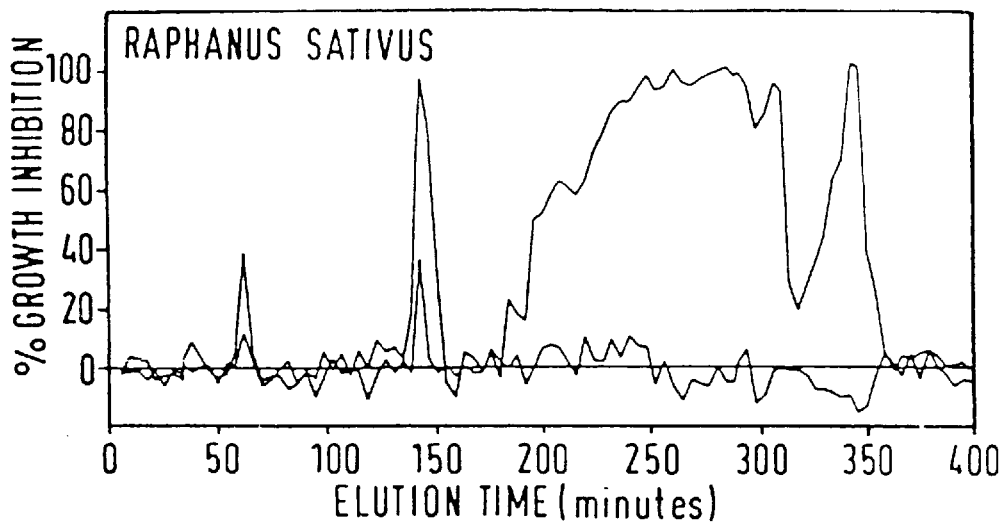
FIGS. 1A and 1B show the cation exchange chromatogram for the Raphanus antifungal proteins and the associated graph of fungal growth inhibition.
Figure 1B:
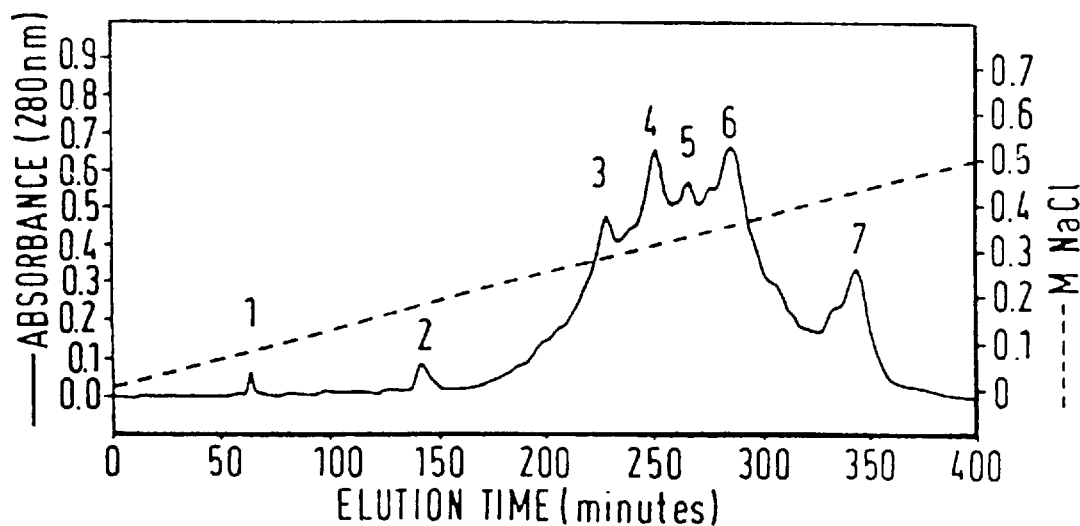

The following Examples illustrate the invention.

EXAMPLE 1
Antifungal and Antibacterial Activity Assays.

Antifungal activity was measured by microspectrophotometry as previously described (Broekaert, 1990, FEMS Microbiol Lett, 69:55–60). Routinely, tests were performed with 20 μl of a (filter-sterilized) test solution and 80 μl of a suspension of fungal spores ($2 \times 10^4$ spores/ml) in half strength potato dextrose broth (½ PDB). Some tests were performed using a suspension of mycelium fragments in a synthetic growth medium. The synthetic growth medium consisted of $K_2HPO_4$ (2.5 mM), $MgSO_4$ (50 μM), $CaCl_2$ (50 μM), $FeSO_4$ (5 μM), $CoCl_2$ (0.1 μM), $CuSO_4$ (0.1 μM), $Na_2MoO_4$ (2 μM), $H_3BO_3$ (0.5 μM), KI (0.1 μM), $ZnSO_4$ (0.5 μM), $MnSO_4$ (0.1 μM), glucose (10 g/l), asparagine (1 g/l), methionine (20 mg/l), myo-inositol (2 mg/1), biotin (0.2 mg/1), thiamine-HCl (1 mg/1), and pyridoxine-HCl (0.2 mg/l). Control microcultures contained 20 μl of sterile distilled water and 80 μl of the fungal suspension.

Unless otherwise stated the test organism was Fusarium culmorum (strain IMI 180420) and incubation was done at 25° C. for 48 hours. Percent growth inhibition is defined as 100 times the ratio of the corrected absorbance of the control microculture minus the corrected absorbance of the test microculture over the corrected absorbance at 595 nm of the control microculture. The corrected absorbance values equal the absorbance at 595 nm of the culture measured after 48 hours minus the absorbance at 595 nm measured after 30 min.

Antibacterial activity was measured microspectrophotometrically as follows. A bacterial suspension was prepared by inoculating soft nutrient agarose (tryptone, 10 g/l; Seaplaque agarose (FMC), 5 g/l). Aliquots (80 μl) of the bacterial suspension ($10^5$ colony forming units per ml) were added to filter-sterilized samples (20 μl) in flat-bottom 96-well microplates. The absorbance at 595 nm of the culture was measured with the aid of a microplate reader after 30 minutes and 24 hours of incubation at 28° C. Percent growth inhibition was calculated as described above for the antifungal activity assay.

EXAMPLE 2
Extraction of the Basic Protein Fraction from Raphanus sativus Seeds.

Ammonium sulphate fractionation of proteins precipitating in the interval of 30 to 70% relative saturation was followed by heat treatment to remove heat-labile proteins, and by isolation of the basic protein fraction (pI>9) by passage over a Q-Sepharose (Pharmacia) anion exchange column equilibrated at pH 9. The detailed methods are described below.

One kg of R sativus seeds (obtained from Aveve, Belgium) was ground in a coffee mill and the resulting meal was extracted for 2 hours at 4° C. with 2 litres of an ice-cold extraction buffer containing 10 mM $NaH_2PO_4$, 15 mM $Na_2HPO_4$, 100 mM KCl, 2 mM EDTA, 2 mM thiourea, and 1 mM PMSF. The homogenate was squeezed through cheesecloth and clarified by centrifugation (30 min at 7,000×g). Solid ammonium sulphate was added to the supernatant to obtain 30% relative saturation and the precipitate formed after standing overnight at room temperature was removed by centrifugation (30 min at 7,000×g). The supernatant was adjusted to 70% relative ammonium sulphate saturation and the precipitate formed overnight at room temperature collected by centrifugation (30 min at 7,000×g). After redissolving the pellet in 400 ml distilled water the solution was heated at 80° C. for 15 min. The coagulated insoluble material was removed by centrifugation (30 min at 7,000×g) and the supernatant was dialyzed extensively against distilled water using tubing (SpectralPor, Spectrum, USA) with a molecular weight cut off of 1,000 Da. After dialysis the solution was adjusted to 50 mM Tris-HCl (pH 9) by addition of the ten-fold concentrated buffer, and subsequently passed over a Q-Sepharose Fast Flow (Pharmacia, Uppsala, Sweden) column (12×5 cm) in equilibrium with 50 mM Tris-HCl (pH 9). The protein fraction passed through the column was dialyzed extensively against distilled water and adjusted to 50 mM sodium N-morpholinoethanesulphonic acid (Na-MES), pH6, by addition of the ten-fold concentrated buffer.

This material represents the basic heat-stable protein fraction of R sativus seeds. Its further chromatographic purification is described in Example 3.

EXAMPLE 3
Purification of Antifungal Proteins from R sativus Seeds.

Figures 1, 2A:
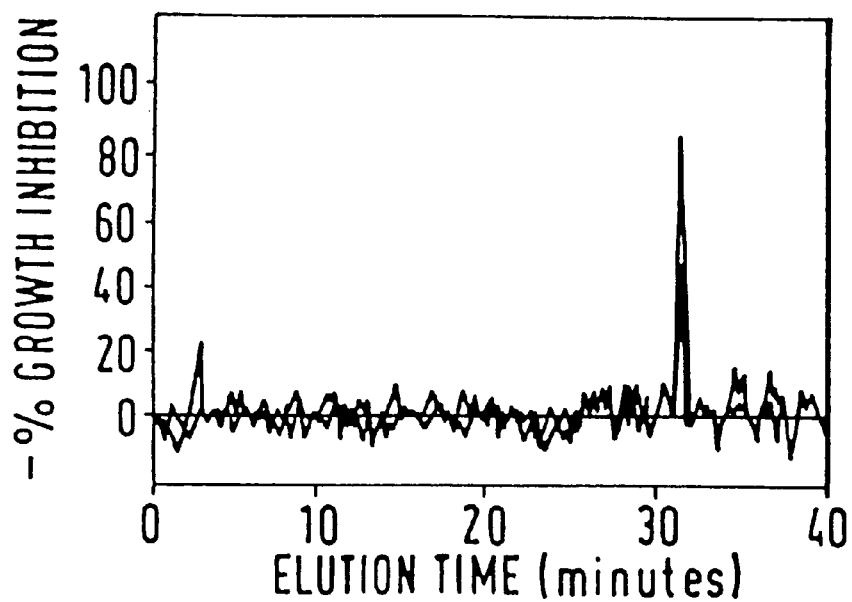
FIGS. 2A-1 and 2A-2 show the HPLC profile of purified Rs-AFP1.

The starting material for the isolation of the R sativus antifungal proteins was the basic heat-stable protein fraction extracted from the mature seeds as in Example 2. These proteins were further separated by cation exchange chromatography, as shown in FIG. 1.

About 150 mg of the basic heat-stable protein fraction dissolved in 50 mM sodium MES (pH 6) was applied on a S-Sepharose High Performance (Pharmacia) column (10× 1.6 cm) previously equilibrated with the sodium MES buffer. The column was eluted at 2.5 ml/min with a linear gradient of 1000 ml from 0 to 500 mM NaCl in 50 mM sodium MES buffer (pH 6). The eluate was monitored for protein by online measurement of the absorbance at 280 nm (results shown in the lower panel of FIG. 1) and collected in 10 ml fractions. Of these fractions, 20 $\mu$l was tested in the microspectrophotometric antifungal activity assay described in Example 1 using either the synthetic growth medium (Medium A: results shown as full lines in the upper panel of FIG. 1) or the same medium supplemented with 1 mM $CaCl_2$ and 50 mM KCl (Medium B: results shown as dashed lines in the upper panel of FIG. 1).

Upon fractionation, the mixture yielded a broad peak representing the unbound fraction, two well resolved peaks (peak 1 and peak 2) eluting around 100 and 200 mM NaCl respectively, and a group of five non-resolved peaks (peaks 3 to 7) eluting between 250 and 450 mM NaCl. No antifungal activity was associated with the unbound fraction, whereas all bound peak fractions displayed antifungal activity when assayed in medium A. However, tests performed in medium B only indicated growth inhibition for the fractions corresponding to peaks 1 and 2, respectively. It appears therefore that the antifungal activity of these fractions is less salt-dependent than that of the fractions from peaks 3 to 7.

The fractions showing antifungal activity in growth medium B (peaks 1 and 2) were further purified by reversed-phase chromatography. About 1 mg amounts of peak 1 material (FIG. 2A) and peak 2 material (FIG. 2B) were loaded on a Pep-S (porous silica $C_2/C_{18}$, Pharmacia) column (25×0.93 cm) in equilibrium with 0.1% TFA. The column was eluted at 5 ml/min with a linear gradient of 200 ml from 0.1% trifluoroacetic acid (TFA) to 40% acetonitrile/0.1% TFA. The eluate was monitored for protein by online measurement of the absorption at 214 nm. Five ml fractions of the eluate were collected, vacuum-dried, and finally dissolved in 0.5 ml distilled water of which 10 $\mu$l was used in a microspectrophotometric antifungal activity assay.

Figures 2, 2A:
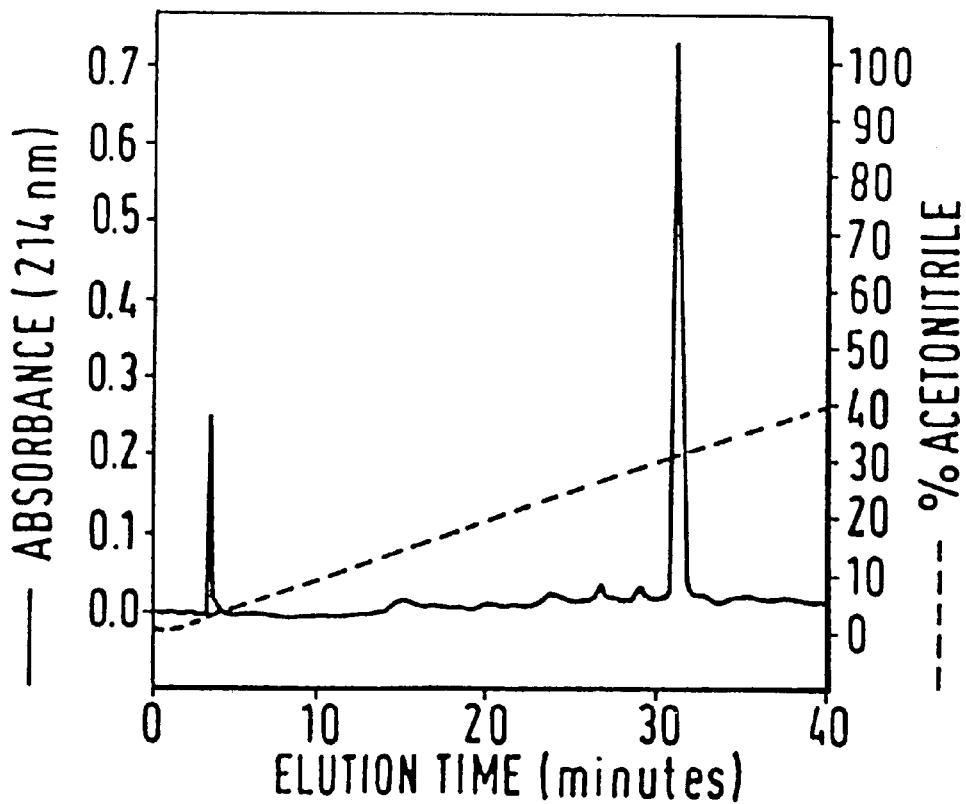
Figures 1, 2B:
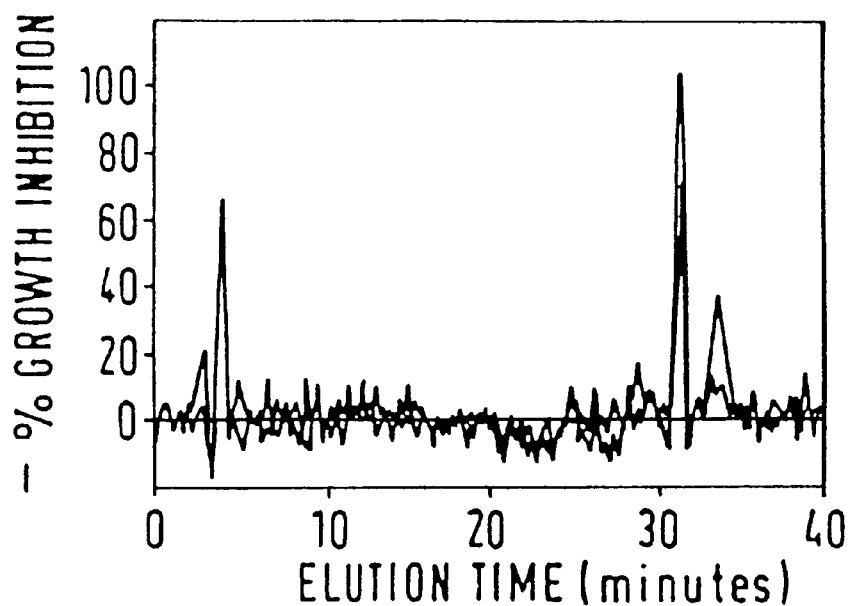
Figures 2, 2B:
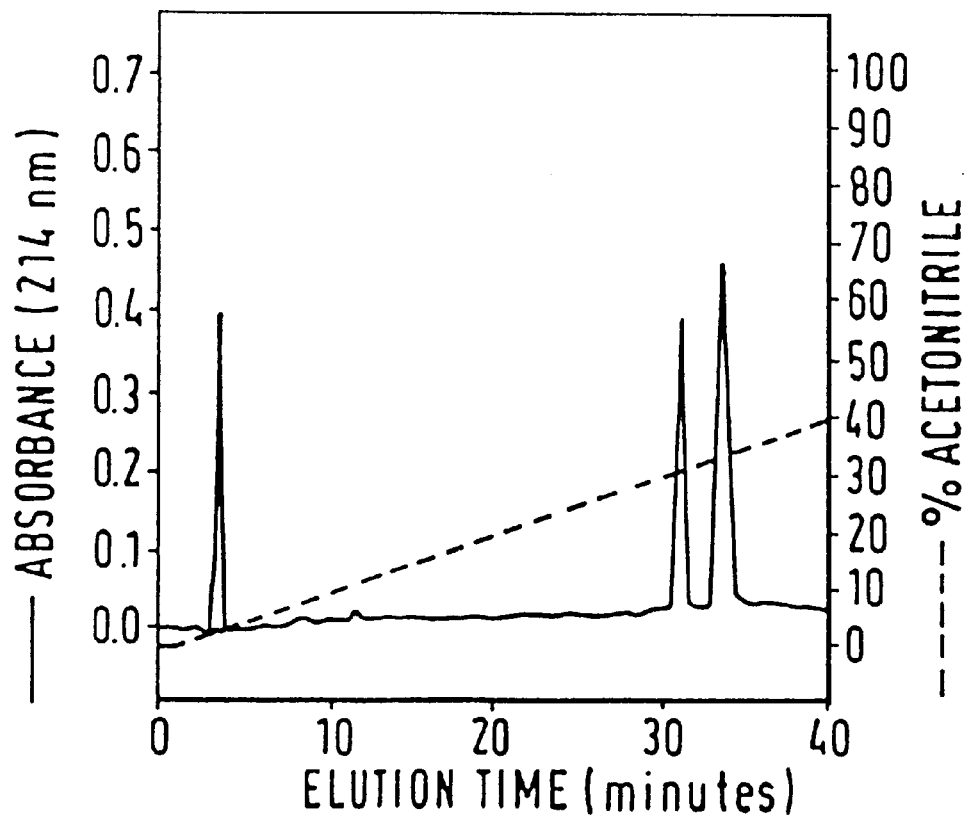

FIG. 2A and FIG. 2B show the HPLC profiles of purified peak 1 and peak 2 material respectively. The lower panels show monitoring of the eluate for protein by measurement of the absorbance at 214 nm. Results of the microspectrophotometric antifungal activity assay in medium A (full line) and medium B (dashed line) are shown in the upper panels.

The material from peak 1 yielded a single major peak eluting at 30% acetonitrile and co-eluting with the antifungal activity in both medium A and medium B. The active factor isolated from this peak is called Rs-AFP1 (*Raphanus sativus* antifungal protein 1). The peak 2 material, on the other hand, resolved into two major peaks eluting at 30% and 33% acetonitrile respectively. The peak eluting at 30% acetonitrile was active in both medium A and medium B, whereas the peak eluting at 33% was active only in medium A. The active factor purified from the 30% acetonitrile peak is called Rs-AFP2 (*Raphanus sativus* antifungal protein 2), and that from the 33% acetonitrile peak is designated Rs-nsLTP (Raphanus sativus non-specific lipid transfer protein) because of its homology with non-specific lipid transfer proteins isolated from other plant species (see Example 13).

EXAMPLE 4
Purity of the Isolated Rs-AFPs.

The purity of the isolated antifungal proteins was verified by native cathodic gel electrophoresis followed by protein staining and in situ detection of antifungal activity using a bio-zymographic technique.

Native cathodic gel electrophoresis and bio-zymography were done as previously described (De Bolle et al, 1991, Electrophoresis, 12, 442–444) with some modifications. Electrophoresis was performed on continuous 10% acrylamide gels containing 60 mM Tris/70 mM MES (pH 7). The electrophoresis buffer consisted of 100 mM L-histidine/41 mM MES (pH 6.5) Gels were cooled at 10° C. during electrophoresis. The samples contained 20% glycerol, 0.0025% methylene blue, and 10 $\mu$g of purified Rs-AFP1 or 20 $\mu$g of Rs-AFP2. Proteins were detected by silver-staining of a diffusion blot prepared from the gel (Kovarik et al, 1987, Folia Biological, 33, 253–257). The gel was overlaid with a soft agar gel (De Bolle et al, 1991, Electrophoresis, 12, 442–444) containing viable *Trichoderma hamatum* spores and incubated at 25° C. for 3 days.

Rs-AFP1 and Rs-AFP2 migrate as single protein bands after cathodic gel electrophoresis. Moreover, the antifungal activity co-migrated exactly with the protein bands in the gel. These results indicate that the isolated factors are highly pure and that the antifungal activity is not attributable to minor contaminants.

EXAMPLE 5
Antifungal Proteins Related to Rs-AFPs from other Species of Brassicaceae.

Using the purification procedure described in Example 3, we have isolated antifungal proteins from other Brassicaceae, including *Brassica napus, Brassica rapa, Sinapis alba* and *Arabidopsis thaliana*.

Figures 3A, 3B:
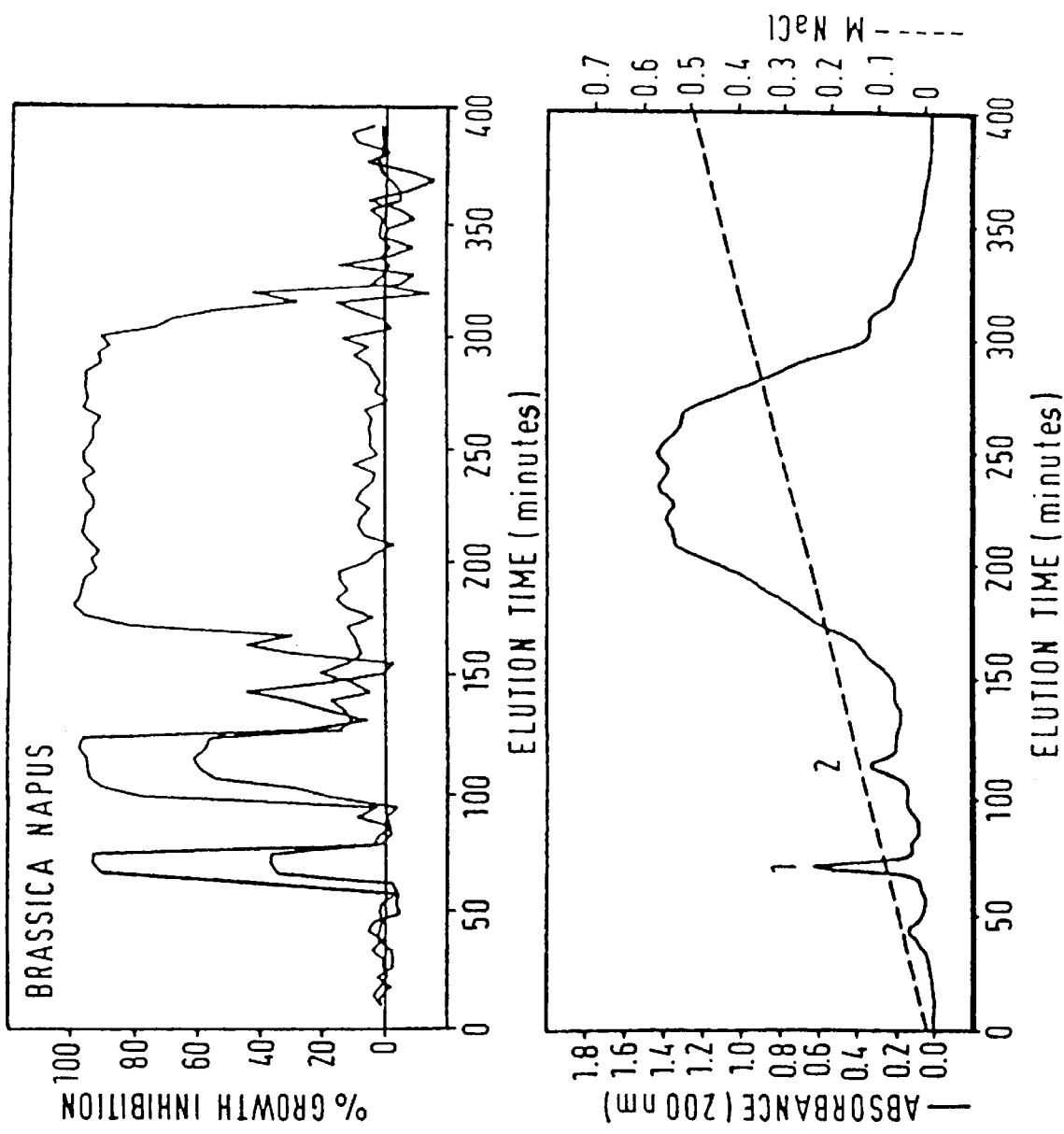
FIGS. 3A and 3B show the cation exchange chromatogram for the *B napus* antifungal proteins and the associated graph of fungal growth inhibition.
Figure 4B:
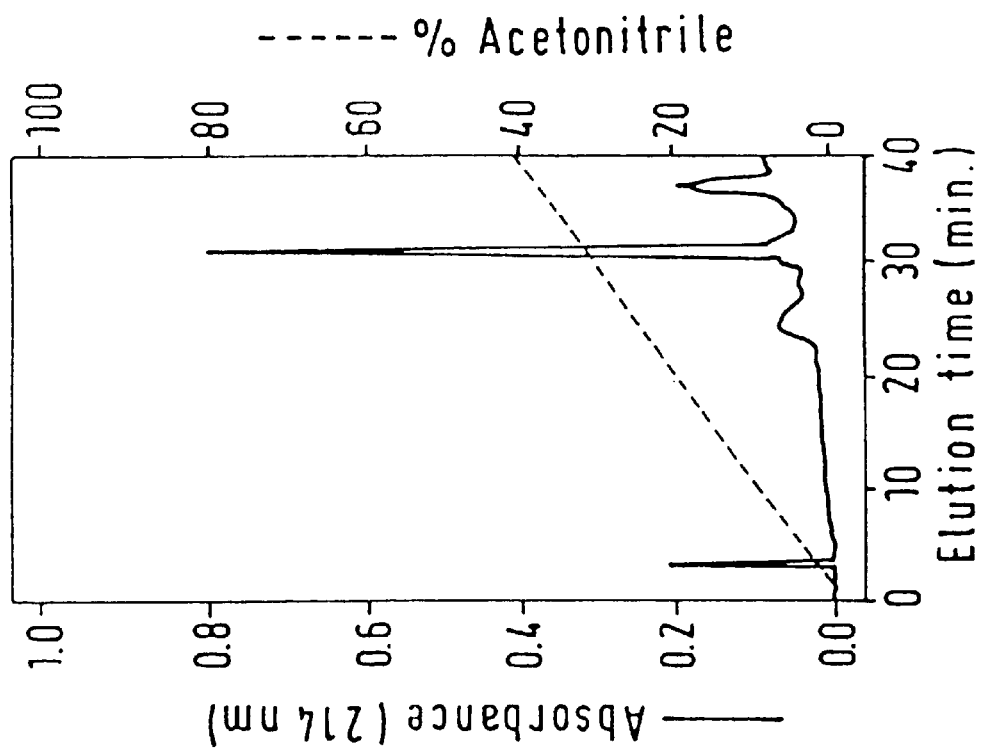
FIGS. 4A and 4B show the HPLC profile of purified *B napus* antifungal proteins.
Figure 4A:
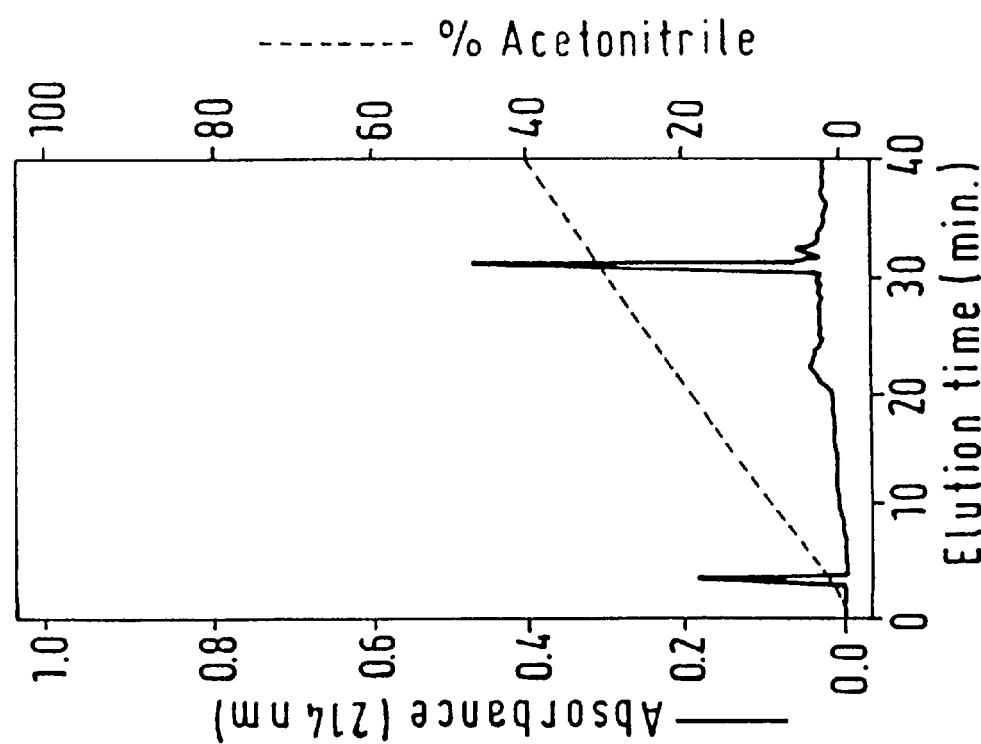

FIGS. 3A and 3B shows the cation exchange chromatogram for antifungal protein isolated from *B napus*, and the associated graph of fungal growth inhibition. FIGS. 4A and 4B show the HPLC profile of the purified *B napus* antifungal proteins, isolated from peak 1 (Bn-AFP1, FIG. 4A) and peak 2 (Bn-AFP2, FIG. 4B).

Figures 5A, 5B:
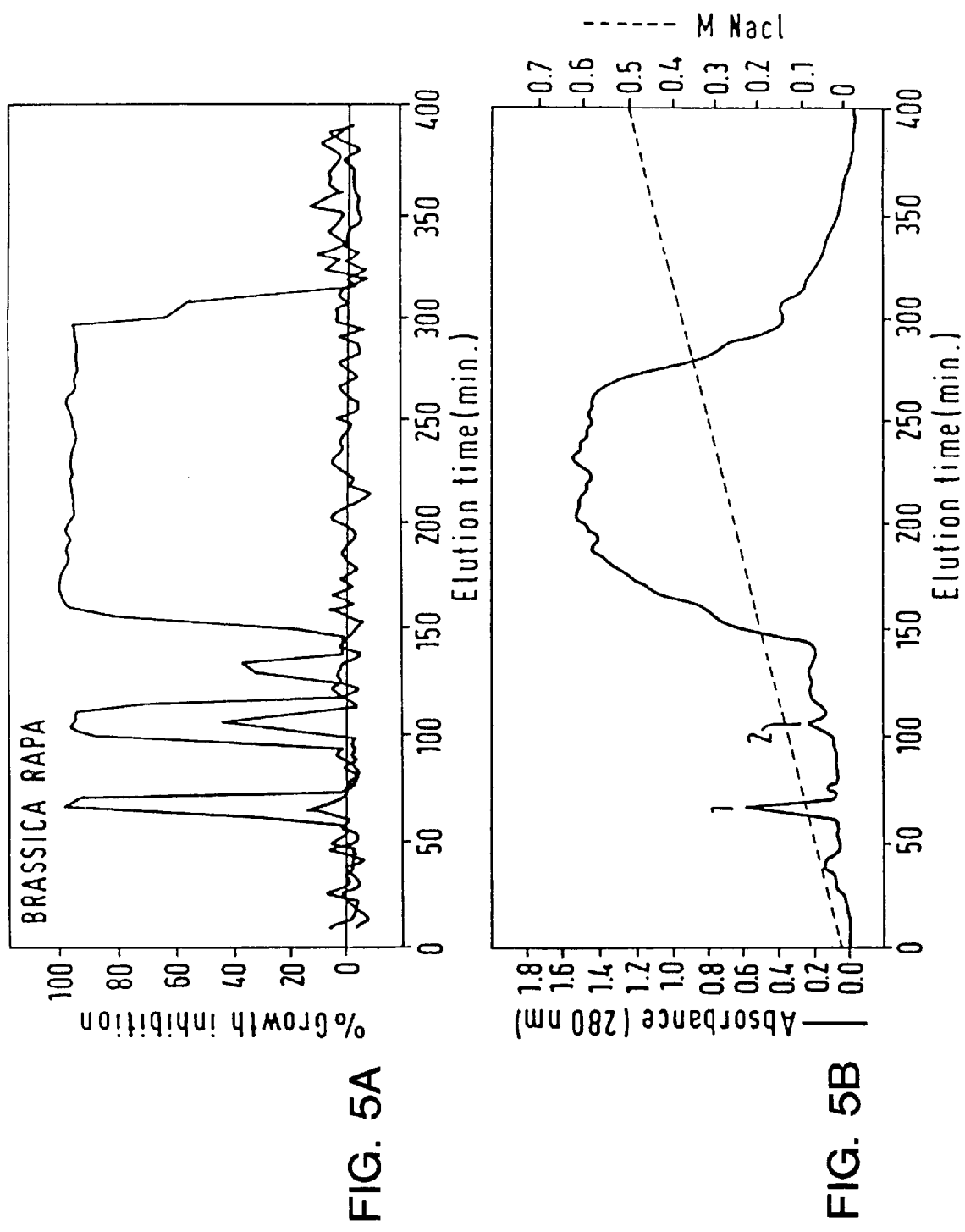
FIGS. 5A and 5B show the cation exchange chromatogram for *B rapa* antifungal proteins and the associated graph of fungal growth inhibition.
Figure 6B:
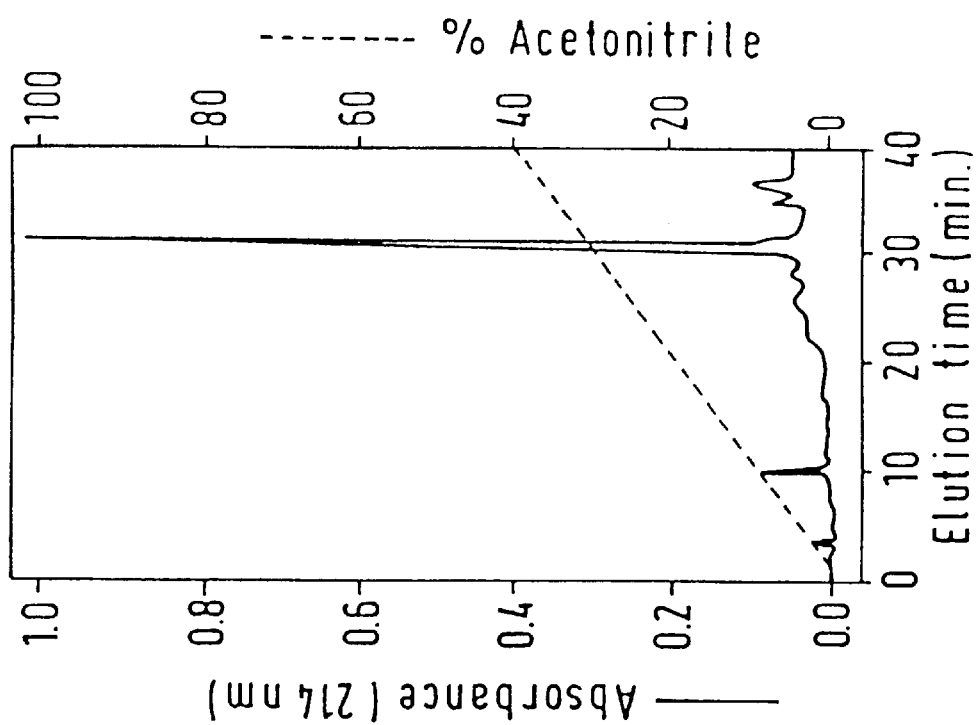
FIGS. 6A and 6B show the HPLC profile of purified *B rapa* antifungal proteins.
Figure 6A:
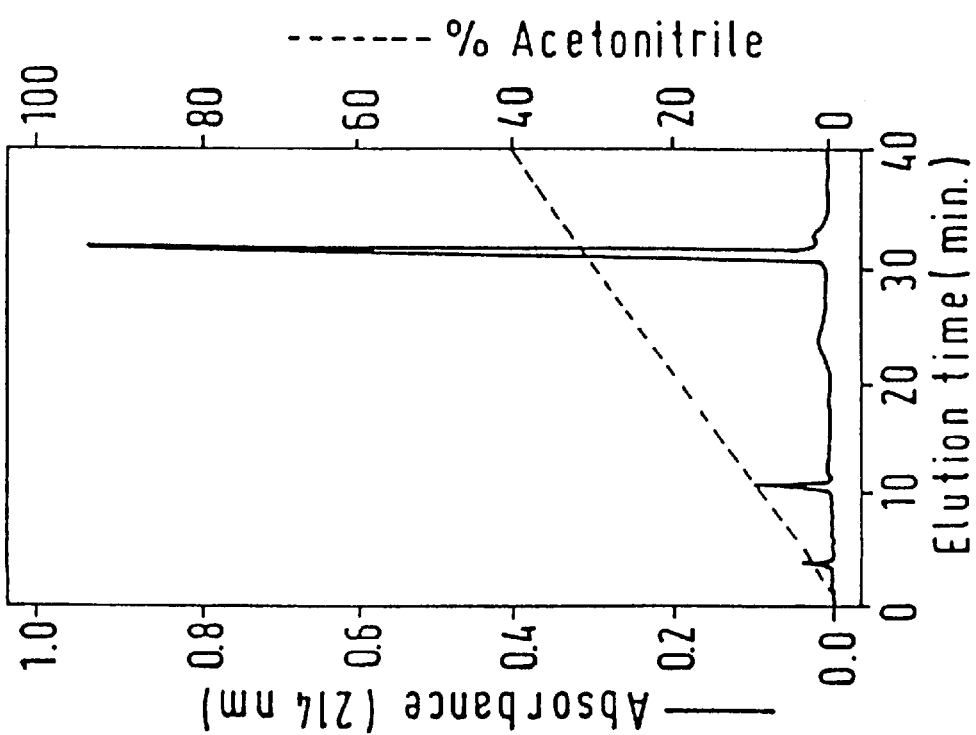

FIGS. 5A and 5B show the cation exchange chromatogram for antifungal protein isolated from *B rapa*, and the associated graph of fungal growth inhibition. FIGS. 6A and 6B show the HPLC profile of the purified *B rapa* antifungal proteins, isolated from peak 1 (Br-AFP1, FIG. 6A) and peak 2 (Br-AFP2, FIG. 6B).

Figure 7A:
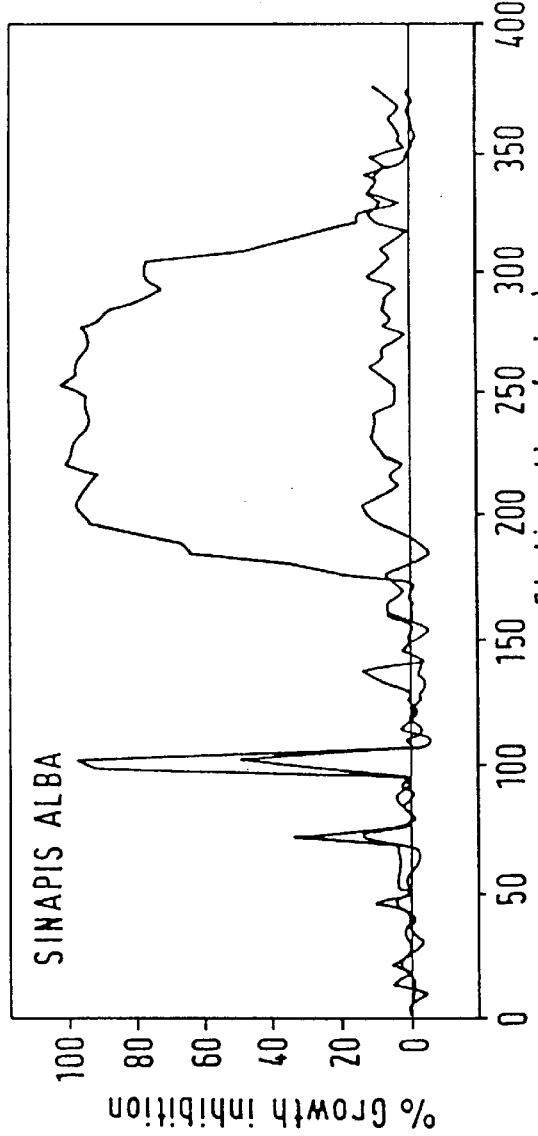
FIGS. 7A and 7B show the cation exchange chromatogram for *S alba* antifungal proteins and the associated graph of fungal growth inhibition.
Figure 7B:
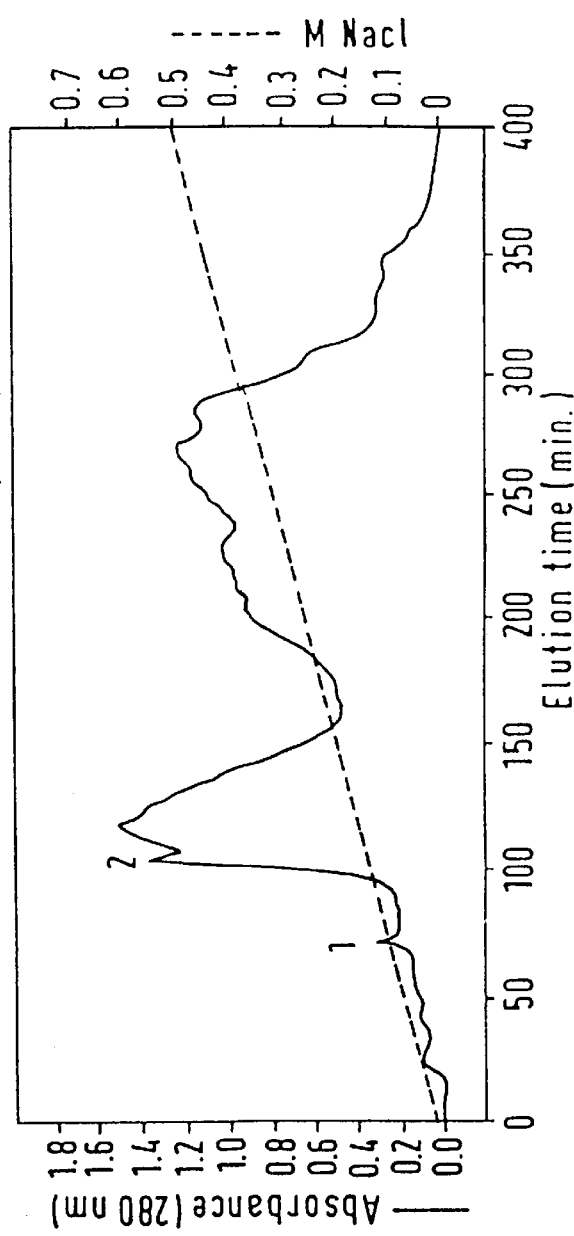
Figure 8B:
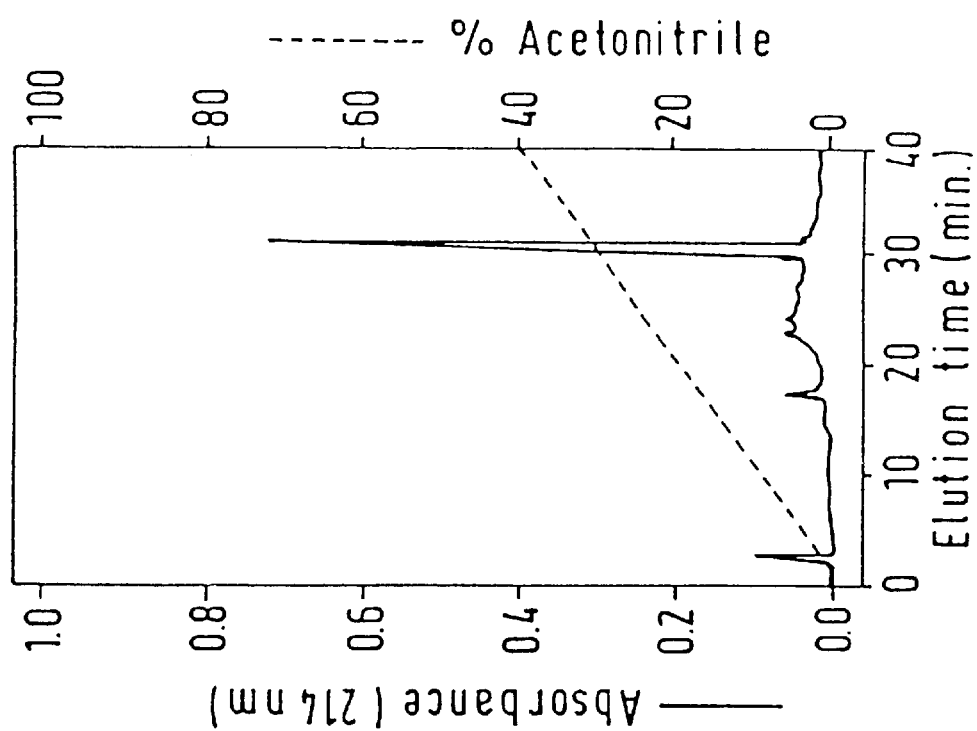
FIGS. 8A and 8B show the HPLC profile of purified *S alba* antifungal proteins.
Figure 8A:
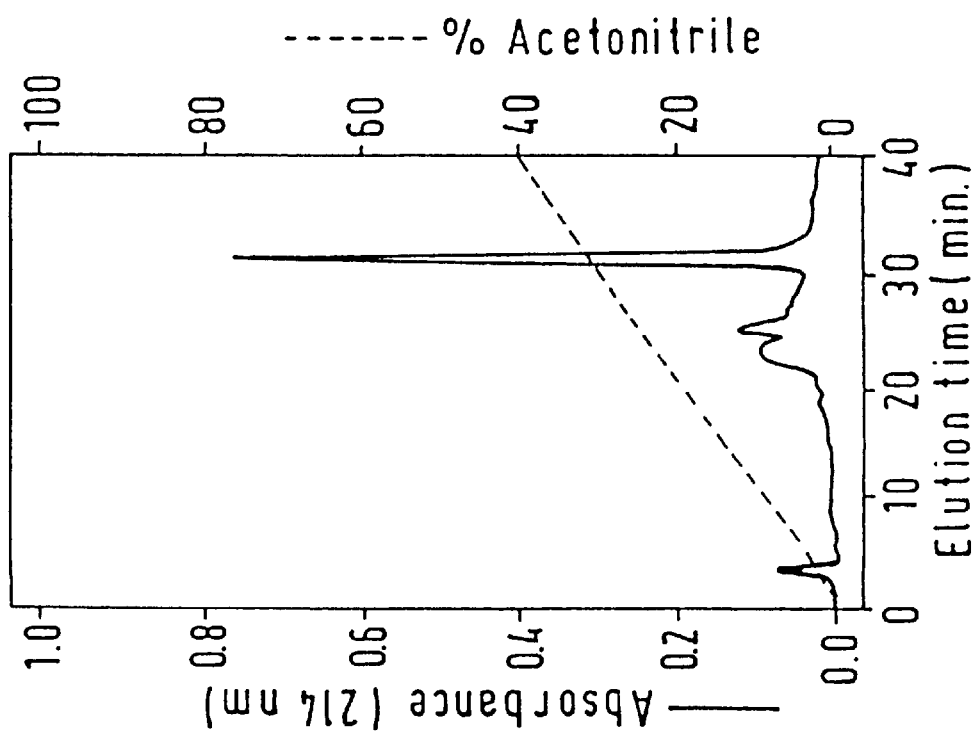

FIGS. 7A and 7B show the cation exchange chromatogram for antifungal protein isolated from *S alba*, and the associated graph of fungal growth inhibition (upper panel). FIGS. 8A and 8B show the HPLC profile of the purified *S alba* antifungal proteins, isolated from peak 1 (Sa-AFP1, FIG. 8A) and peak 2 (Sa-AFP2, FIG. 8B).

Figures 9A, 9B:
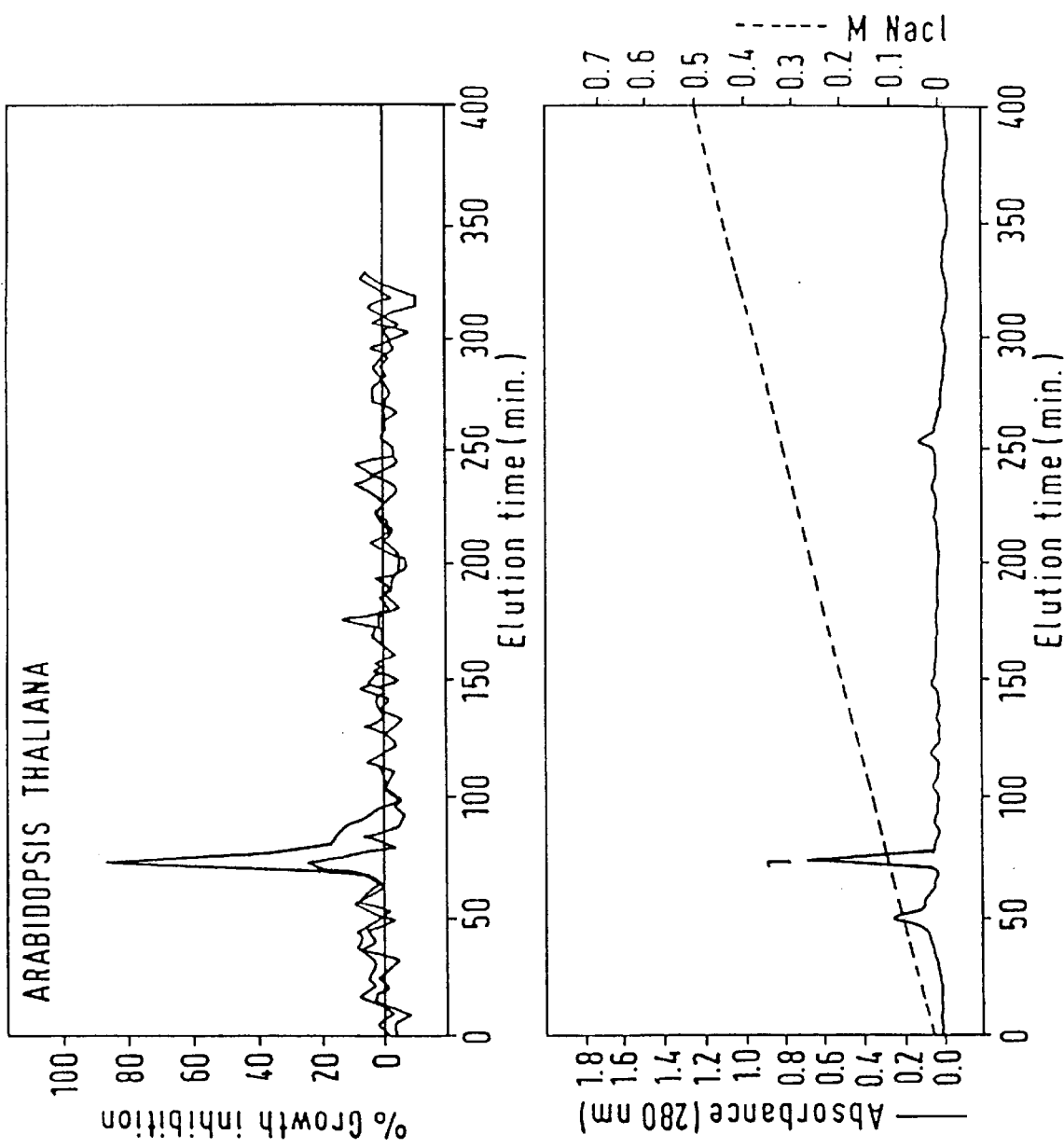
FIGS. 9A and 9B show the cation exchange chromatogram for A thaliana antifungal protein and the associated graph of fungal growth inhibition.
Figure 10:
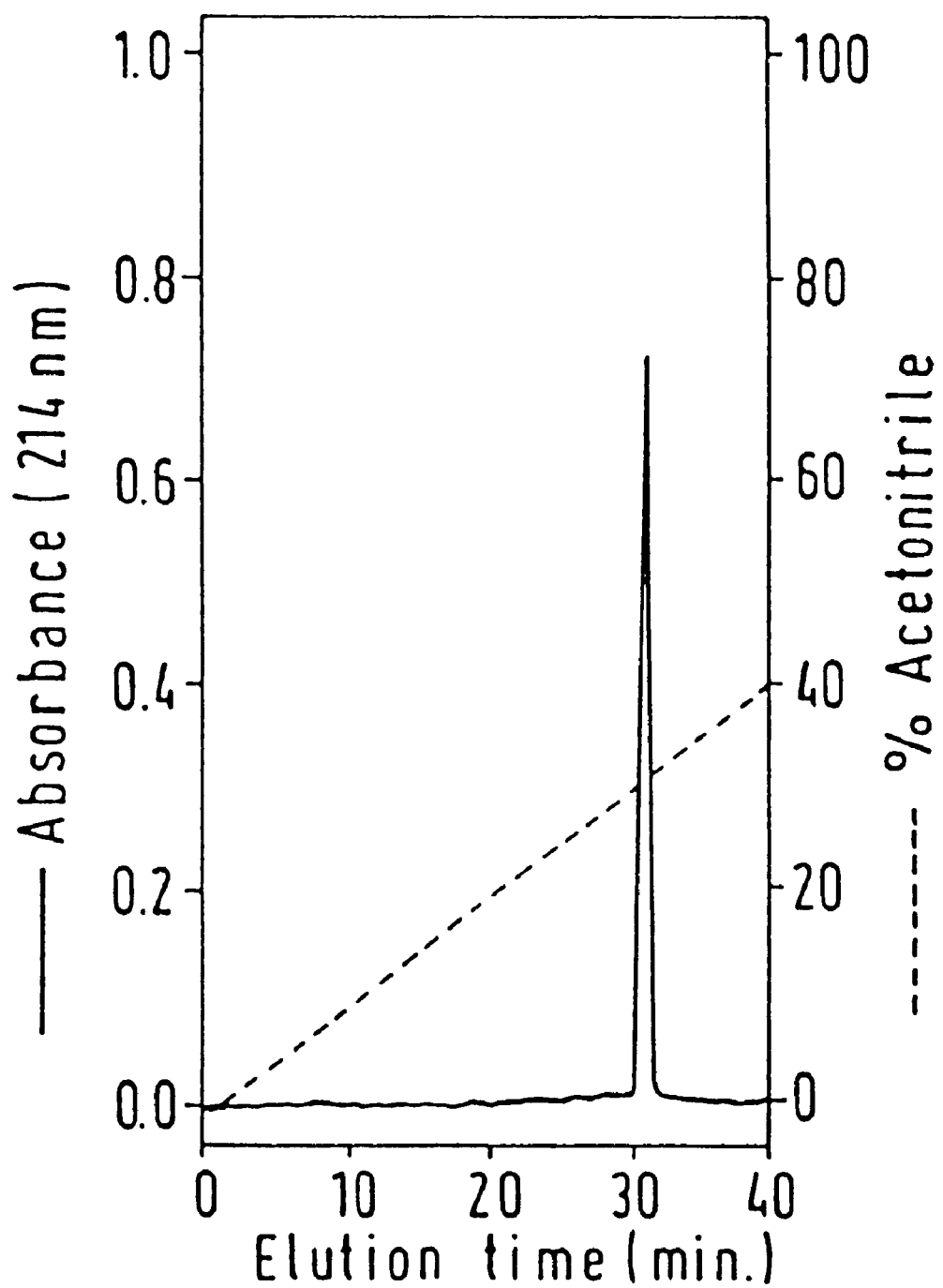
FIG. 10 shows the HPLC profile of purified A thaliana antifungal proteins.

FIGS. 9A and 9B show the cation exchange chromatogram for antifungal protein isolated from *A thaliana*, and the associated graph of fungal growth inhibition. FIG. 10 shows the HPLC profile of the purified *A thaliana* antifungal proteins, isolated from peak 1 (At-AFP1).

All these antifungal proteins behave similarly to Rs-AFP1 and Rs-AFP2 with respect to their SDS-PAGE and isoelectric focusing pattern (as described in Example 5).

EXAMPLE 6
Extraction of the Basic Protein Fraction from *Dahlia merckii, Cnicus benedictus, Lathyrus cicera* and *Clitoria ternatea* Seeds.

Five hundred grams of *D merckii* or *C benedictus* or *Clitoria ternatea* seeds (purchased from Chiltern Seeds, Cumbria, UK) or *Lathyrus cicera* seeds (from Instituto Botanico Universitade Coimbra, Portugal) were ground in a coffee mill and the resulting meal was extracted for 2 hours at 40° C. with 2 litres of an ice-cold extraction buffer containing 10 mM $NaH_2PO_4$, 15 mM $Na_2HPO_4$, 100 mM KCl, 2 mM EDTA and 1 mM benzamidine. The resulting homogenate was squeezed through cheesecloth and clarified by centrifugation (30 min at 7,000×g). Solid ammonium sulphate was added to the supernatant to obtain 75% relative saturation and the precipitate allowed to form by standing overnight at 40° C. Following centrifugation at 7,000×g for 30 minutes, the precipitate was redissolved in a minimal volume of distilled water and dialyzed extensively against distilled water using benzoylated cellulose tubing (Sigma, St Louis, Mo.). After dialysis the solution was adjusted to 50 mM $NH_4AC$ (pH 9) by addition of the ten-fold concentrated buffer and passed over a Q-Sepharose Fast Flow (Pharmacia, Uppsala, Sweden) column (12×5 cm) equilibrated in 50 mM $NH_4Ac$ (pH 9). The protein fraction which passed through the column was adjusted to pH6 with acetic acid.

This material represents the basic (pI>9) protein fraction of the seeds. The fractions were further purified as described in Examples 7, 8, 9 and 10.

EXAMPLE 7
Purification of Antimicrobial Proteins from *Dahlia merckii* Seeds.

The starting material for the isolation of the *D merckii* antimicrobial proteins was the basic protein fraction extracted from the mature seeds as in Example 6. Proteins were further purified by cation exchange chromatography of this extract.

Figure 11A:
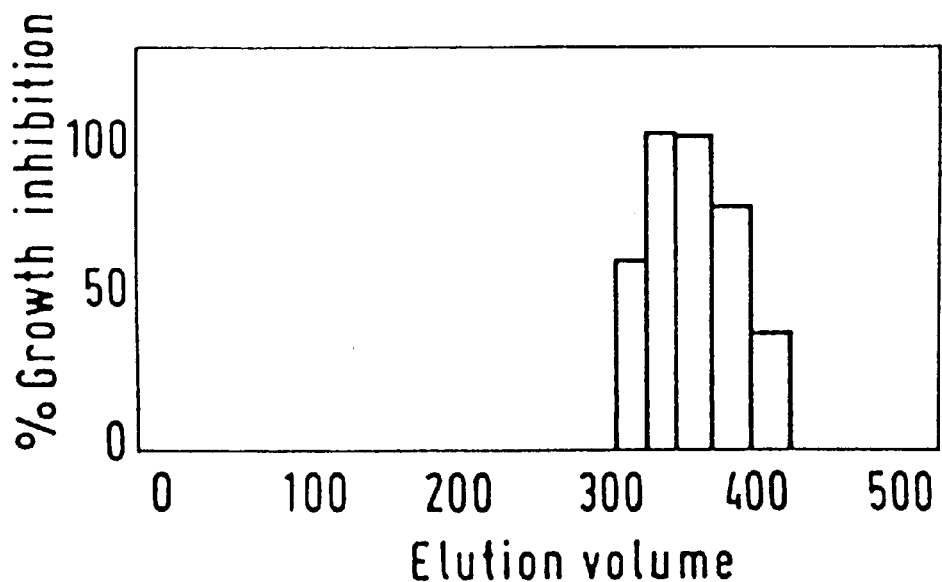
FIGS. 11A and 11B show the cation exchange chromatogram for the basic extract of Dahlia merckii and the corresponding graph of antifungal activity.
Figure 11B:
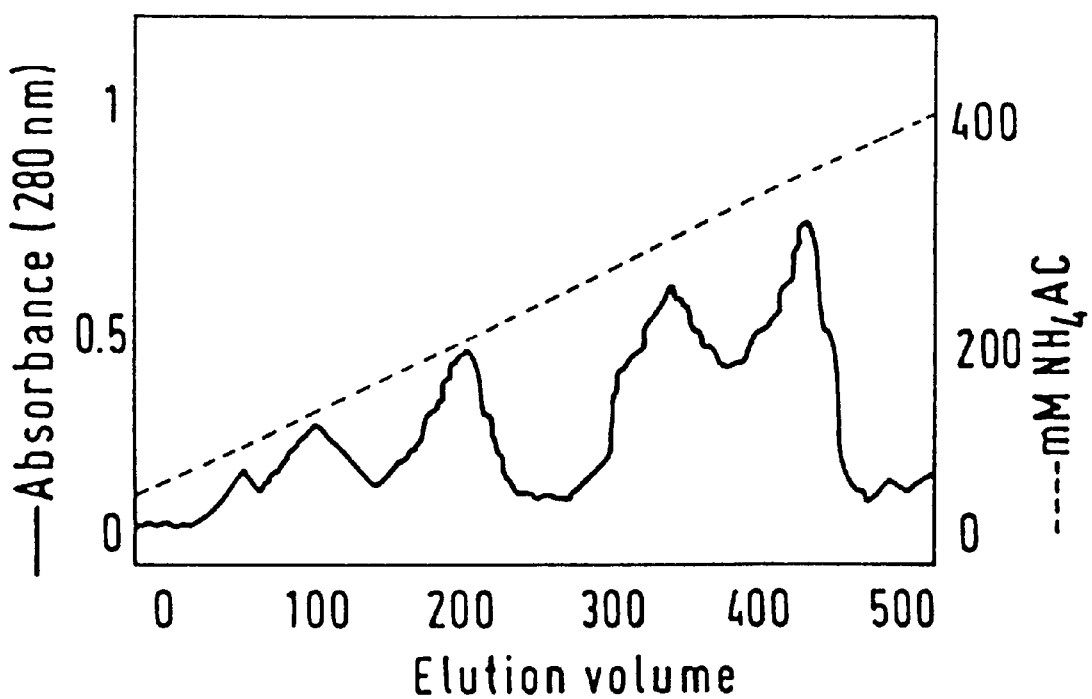

Approximately 500 ml of the basic protein fraction was applied to a S-Sepharose High Performance (Pharmacia) column (10×1.6 cm) equilibrated in 50 mM $NH_4Ac$, pH 6.0. The column was eluted at 3.0 ml/min with a linear gradient of 50–750 ml $NH_4Ac$, pH 6.0 over 325 minutes. The eluate was monitored for protein by online measurement of the absorbance at 280 nm (results shown in FIG. 11B) and collected in 10 ml fractions. Samples from each fraction were assayed for antifungal activity as described in Example 1 (results shown in FIG. 11A).

Figure 12A:
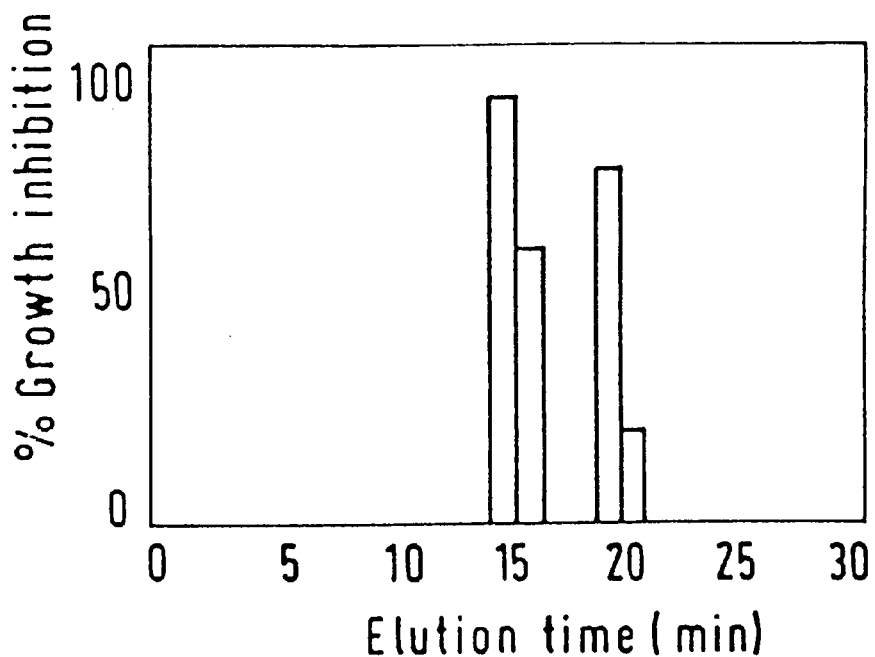
FIGS. 12A and 12B show the reverse-phase HPLC profile of purified Dm-AMP1 and Dm-AMP2.
Figure 12B:
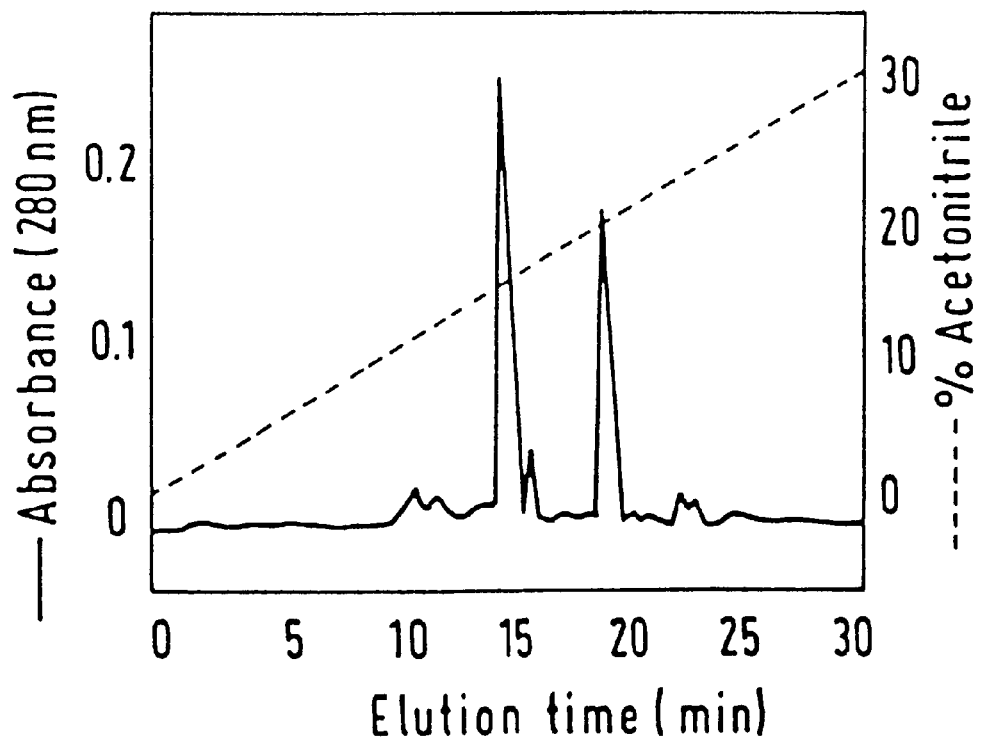

Following chromatography, the extract yielded a broad peak of activity eluting at around 250 mM NH4Ac. The fractions showing antifungal activity were pooled and further purified by reverse-phase HPLC. About 3 mg amounts of the peak were loaded on a PEP-S (porous silica $C_2/C_{18}$, Pharmacia) column (25×0.4 cm) equilibrated with 0.1% TFA (trifluoracetic acid). The column was developed at 1 ml/min with a linear gradient of 0.1% TFA to 100% acetonitrile/0.1% TFA over 100 minutes. The eluate was monitored for protein by online measurement of the absorption at 280 nm (results shown in FIG. 12B). One ml fractions were collected, vacuum-dried, and dissolved in 0.5 ml distilled water. 10 μl from each fraction was assayed for antifungal activity (results shown in FIG. 12A). The material yielded two well-resolved peaks of activity, eluting at 18% and 22% acetonitrile. These represent the purified proteins Dm-AMP1 and Dm-AMP2 respectively.

EXAMPLE 8
Purification of Antimicrobial Proteins from *Cnicus benedictus* Seeds.

Figure 13A:
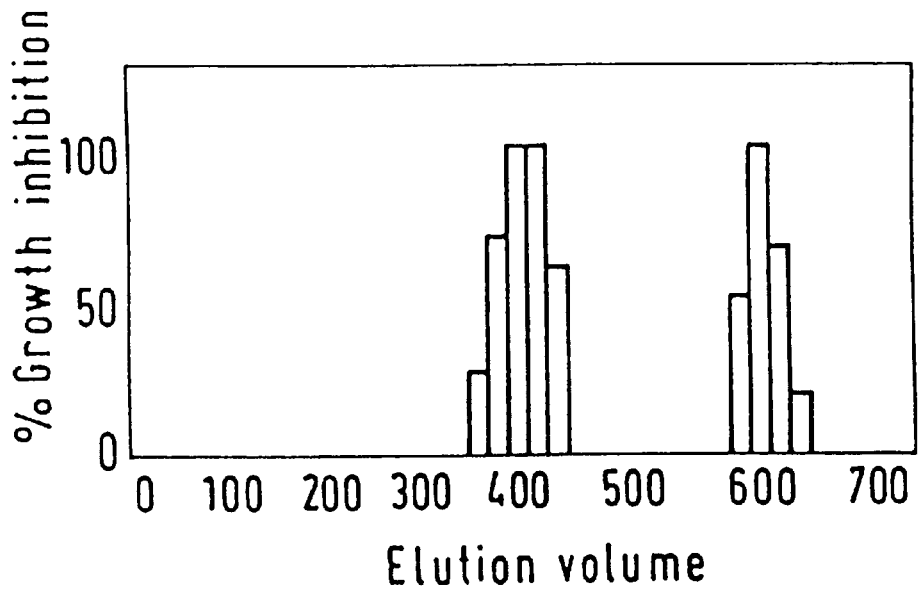
FIGS. 13A and 13B show the cation exchange chromatogram for the basic extract of Cnicus benedictus and the corresponding graph of antifungal activity.
Figure 13B:
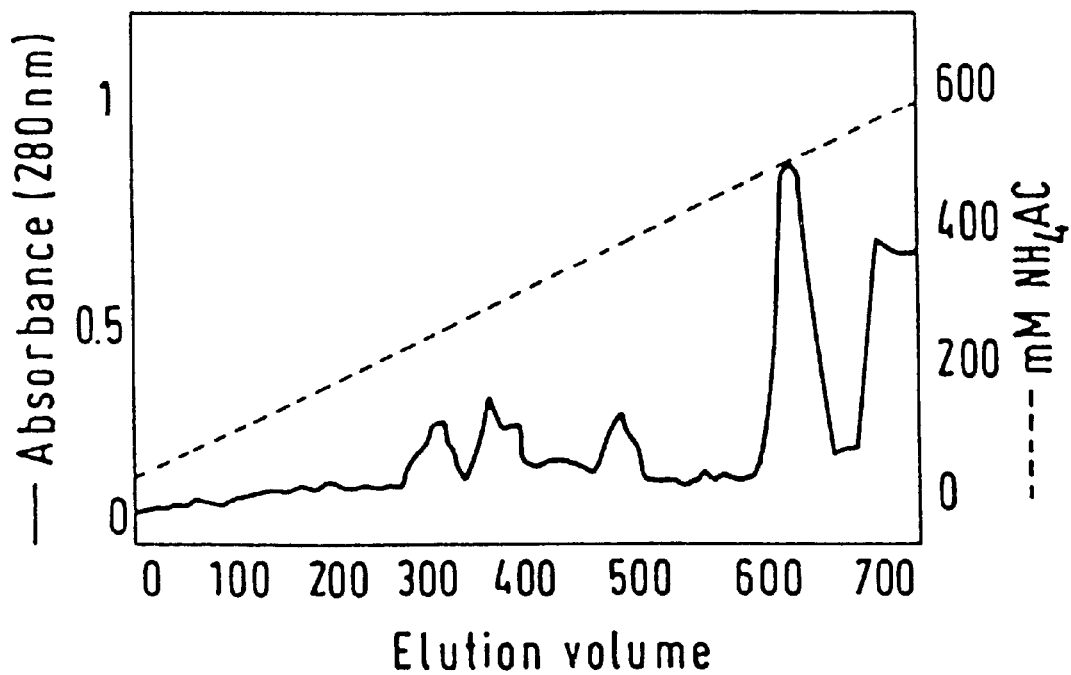

The procedure described in Example 7 was followed using the basic extract from *Cnicus benedictus* seeds. Following chromatography on the S-Sepharose High Performance column, the Cnicus extract yielded two peaks of antifungal activity eluting at approximately 250 mM (peak 1) and 500 mM (peak 2) $NH_4Ac$ (results shown in FIGS. 13A and 13B).

Figure 14A:
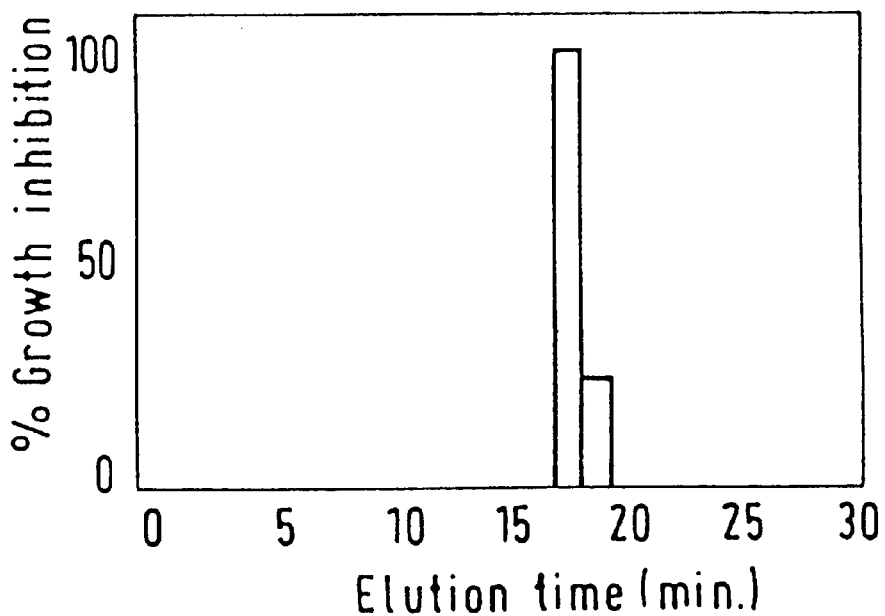
FIGS. 14A and 14B show the reverse-phase HPLC profile of purified Cb-AMP1.
Figure 14B:
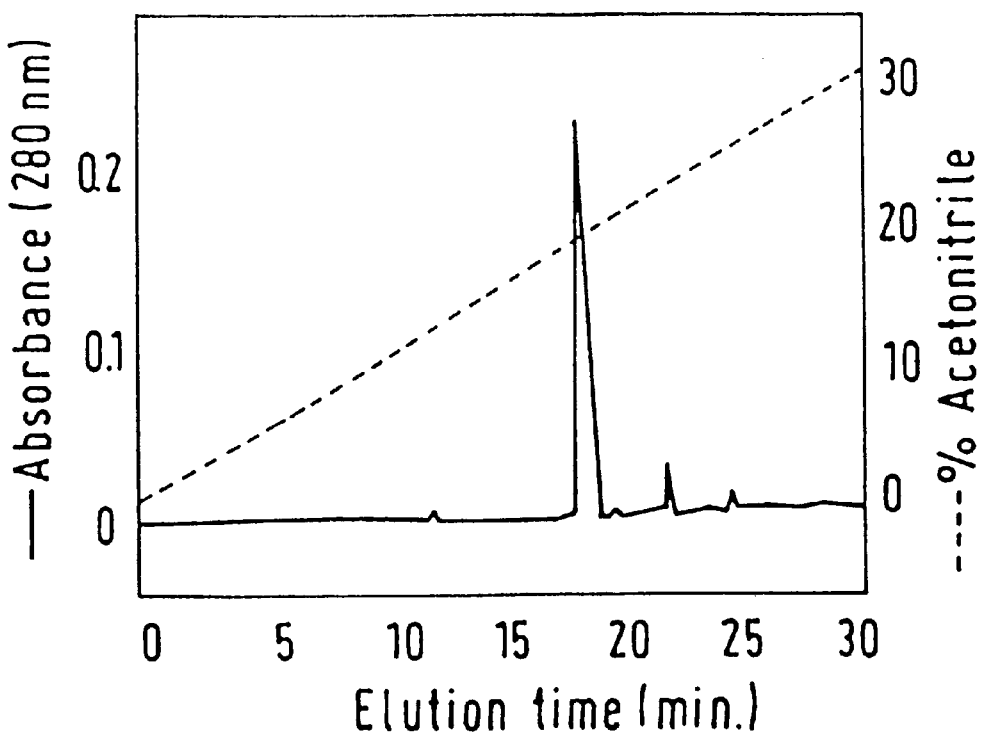
Figure 15A:
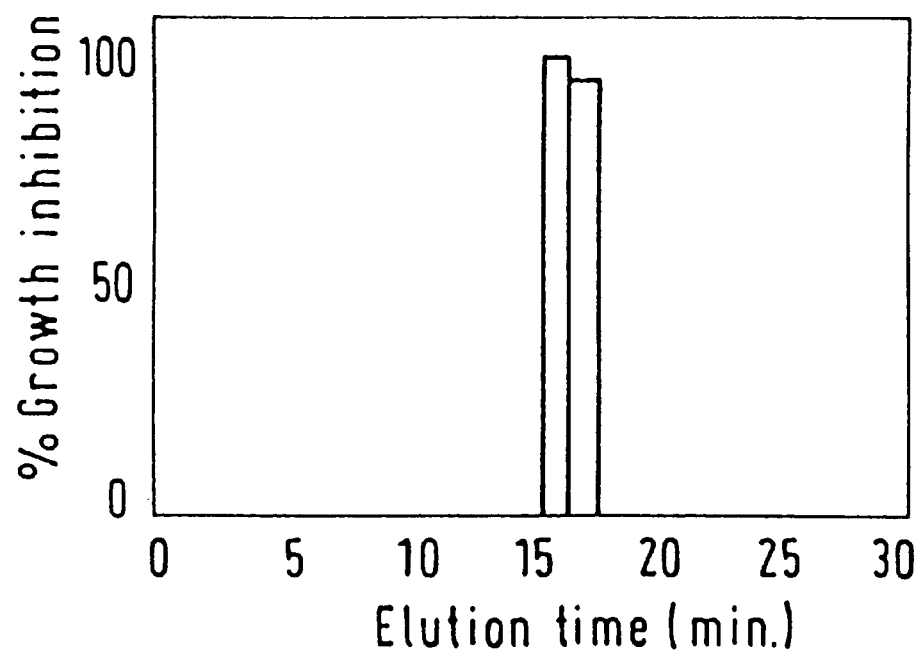
FIGS. 15A and 15B show the reverse-phase HPLC profile of purified Cb-AMP2.
Figure 15B:
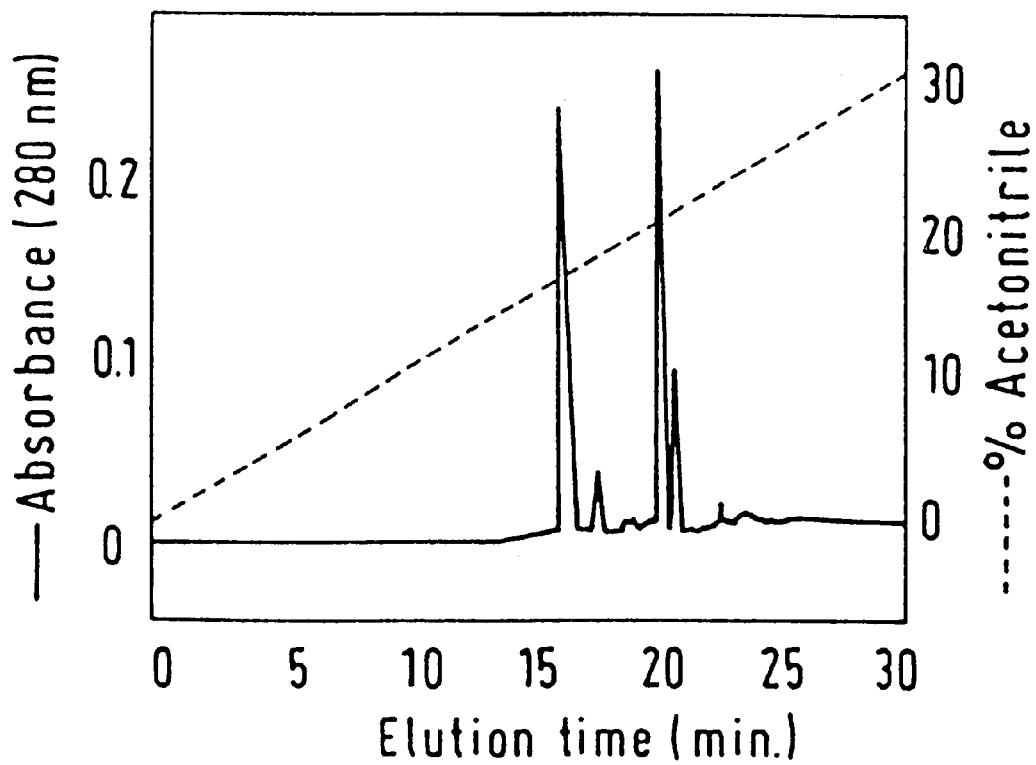

Active fractions were pooled for each peak and further purified on reverse-phase HPLC as described in Example 7. Results for peak 1 are shown in FIGS. 14A and 14B: it yielded an active factor eluting at 18% acetonitrile which is designated Cb-MP1. Similarly peak 2 eluted to a single peak of activity which is designated Cb-AMP2 (results shown in FIGS. 15A and 15B).

EXAMPLE 9
Purification of Antifungal Protein from *Lathyrus cicera* Seeds.

Figure 16A:
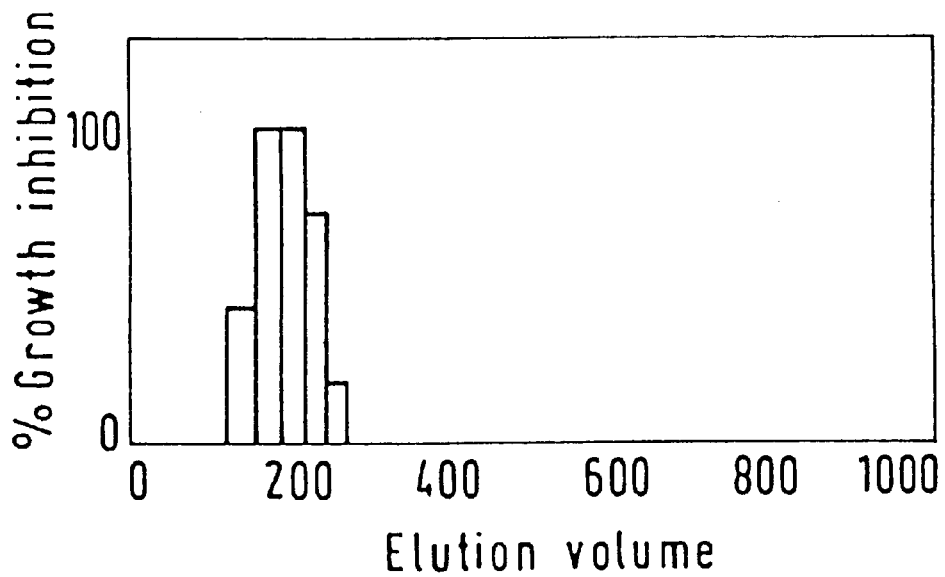
FIGS. 16A and 16B show the cation exchange chromatogram for the basic extract of Lathyrus and the corresponding graph of antifungal activity.
Figure 16B:
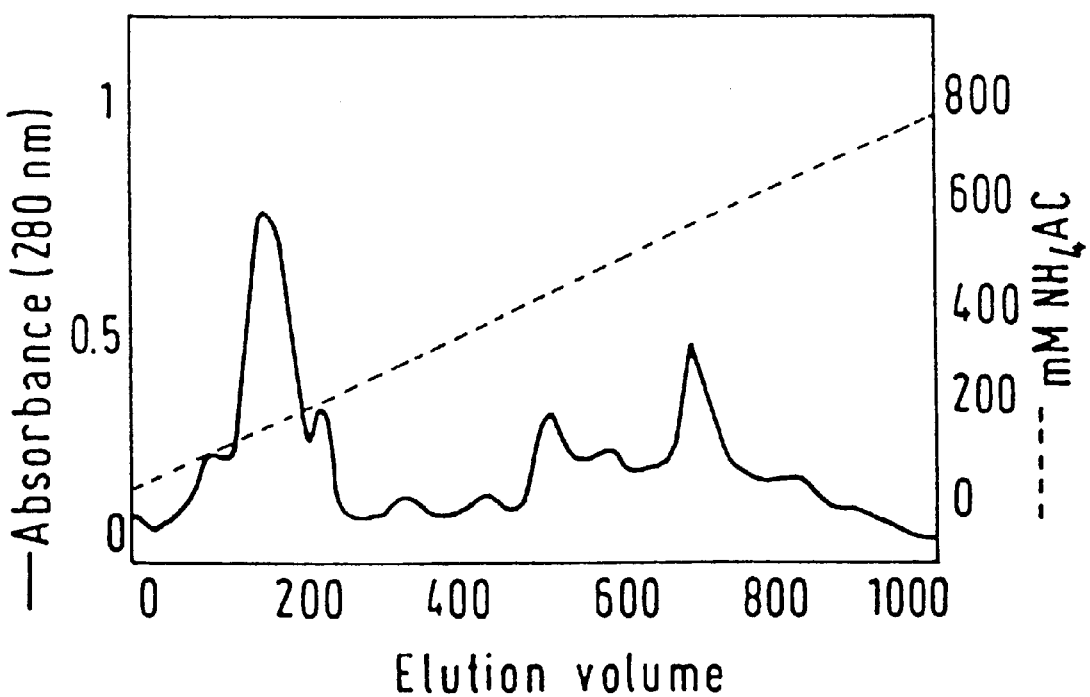

The procedure described in Example 7 was followed using the basic extract from *Lathyrus cicera* seeds. Following chromatography on the S-Sepharose High Performance column, the Lathyrus extract yielded a single peak of antifungal activity eluting at approximately 160 mM $NH_4Ac$ (results shown in FIGS. 16A and 16B).

Figure 17A:
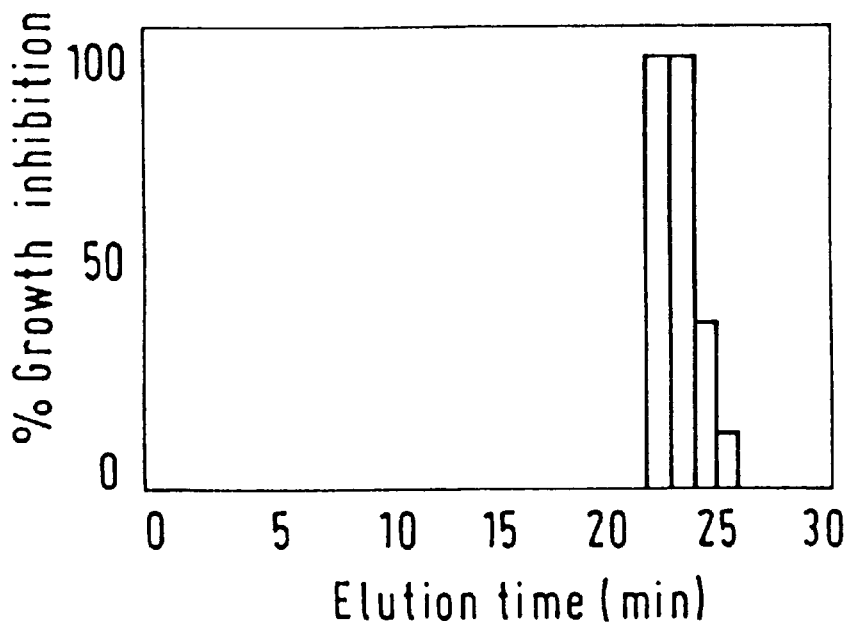
FIGS. 17A and 17B show the reverse-phase HPLC profile of purified Lc-AFP.
Figure 17B:
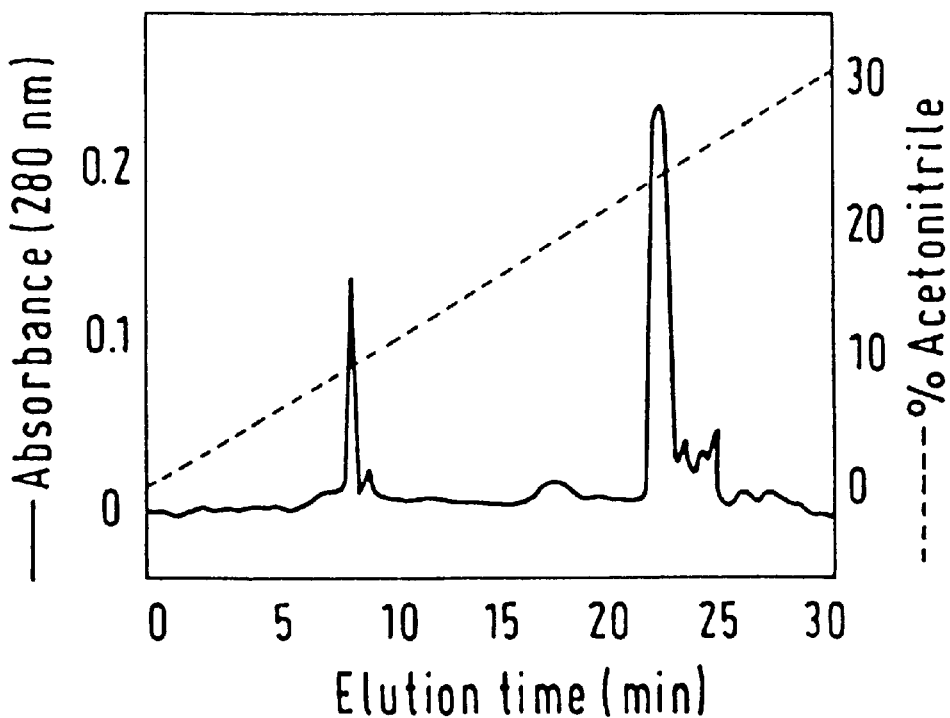

Active fractions were pooled and further purified on reverse-phase HPLC as described in Example 7. Results for peak 1 are shown in FIGS. 17A and 17B: it yielded an active factor eluting at 22% acetonitrile which is designated Lc-AFP.

EXAMPLE 10
Purification of Antimicrobial Proteins from *Clitoria ternatea* Seeds.

Figure 18A:
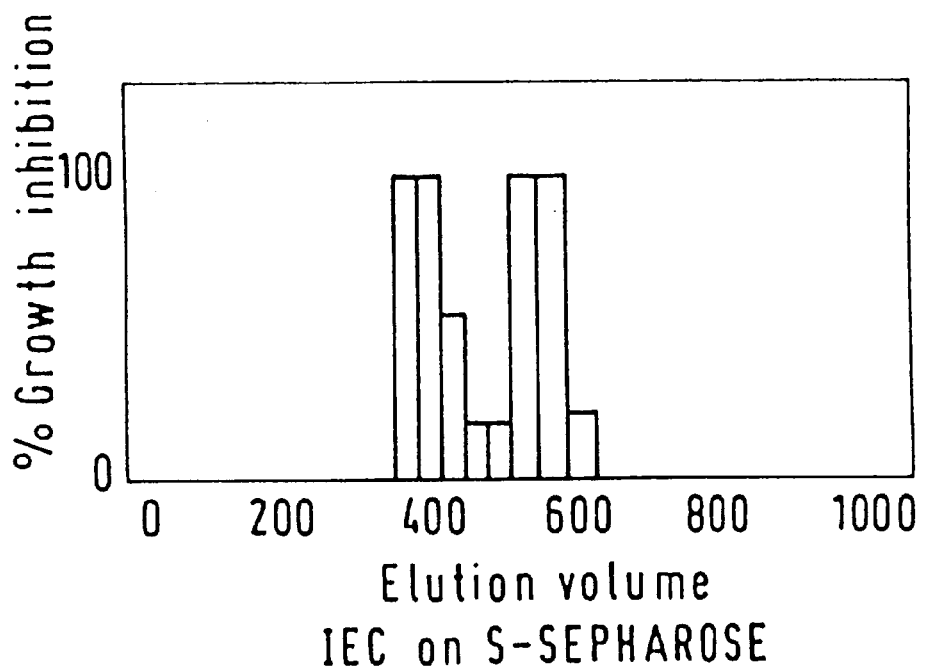
FIGS. 18A and 18B show the cation exchange chromatogram for the basic extract of Clitoria and the corresponding graph of antifungal activity.
Figure 18B:
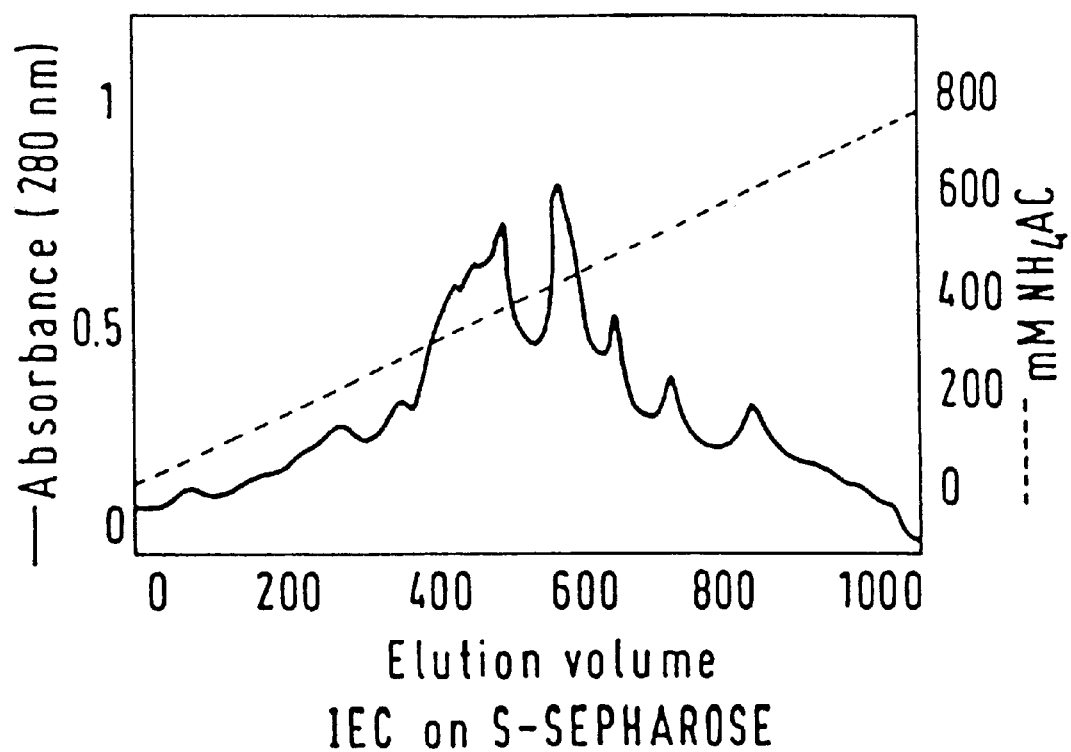

The procedure described in Example 7 was followed using the basic extract from *Clitoria ternatea* seeds. Following chromatography on the S-Sepharose High Performance column, the Clitoria extract yielded two partially resolved peaks of antifungal activity eluting between 260 mM and 400 mM $NH_4Ac$ (results shown in FIGS. 18A and 18B).

Figure 19A:
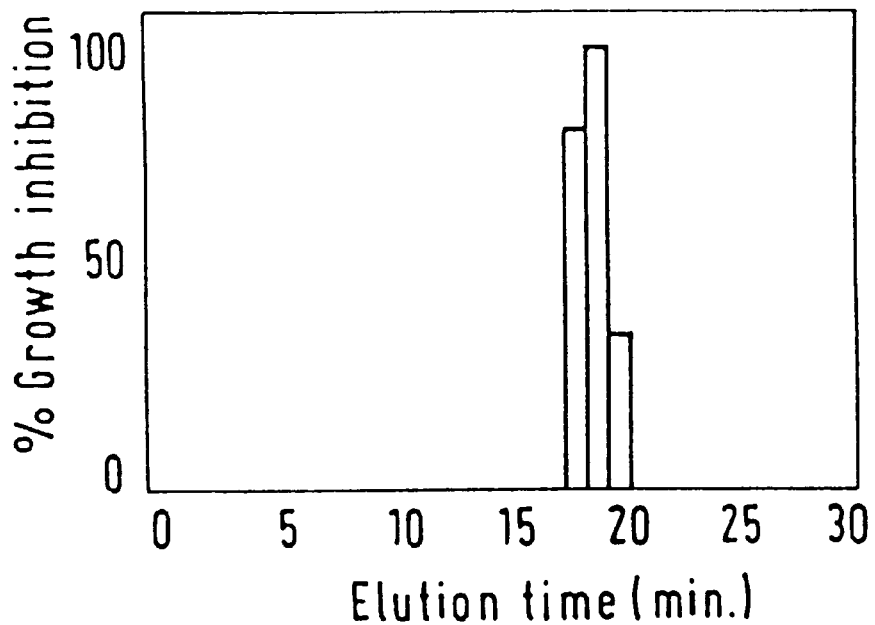
FIGS. 19A and 19B show the reverse-phase HPLC profile of purified Ct-AMP1.
Figure 19B:
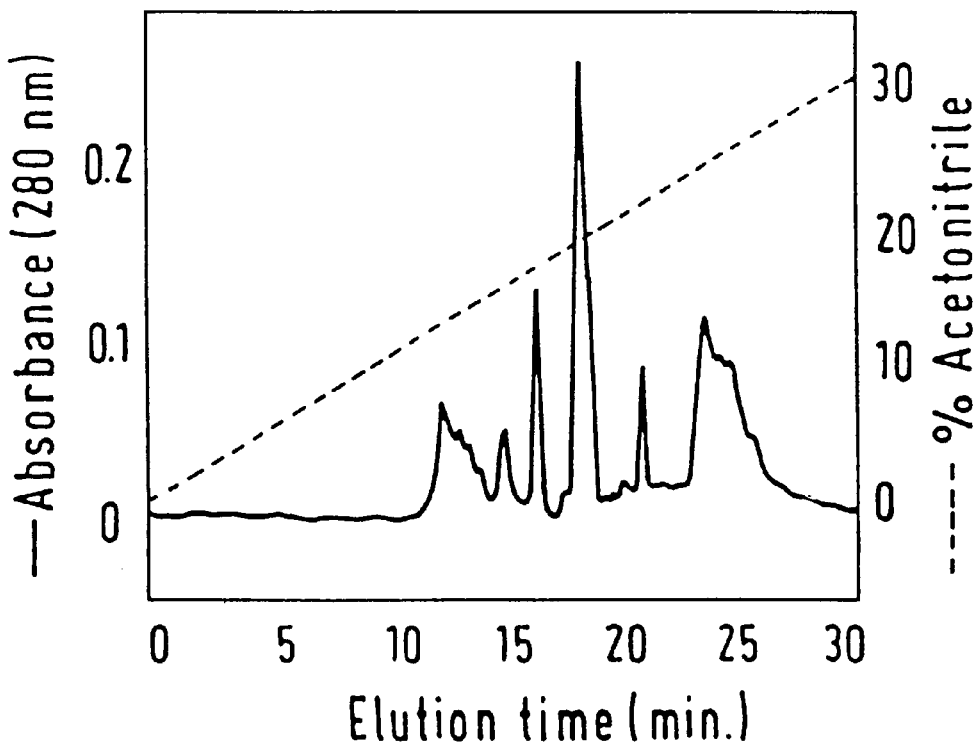
Figure 20A:
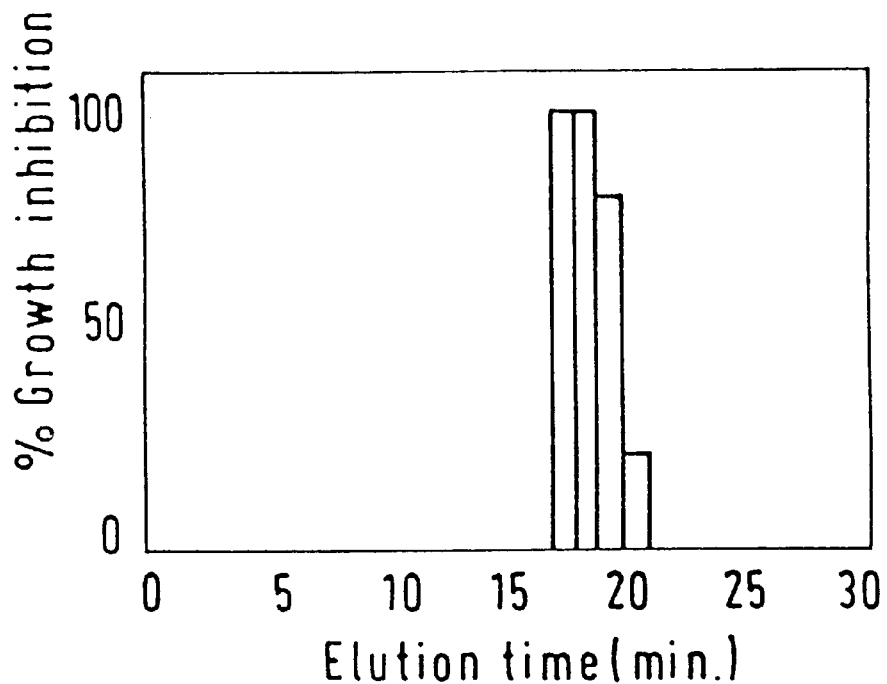
FIGS. 20A and 20B show the reverse-phase HPLC profile of purified Ct-AMP2.
Figure 20B:
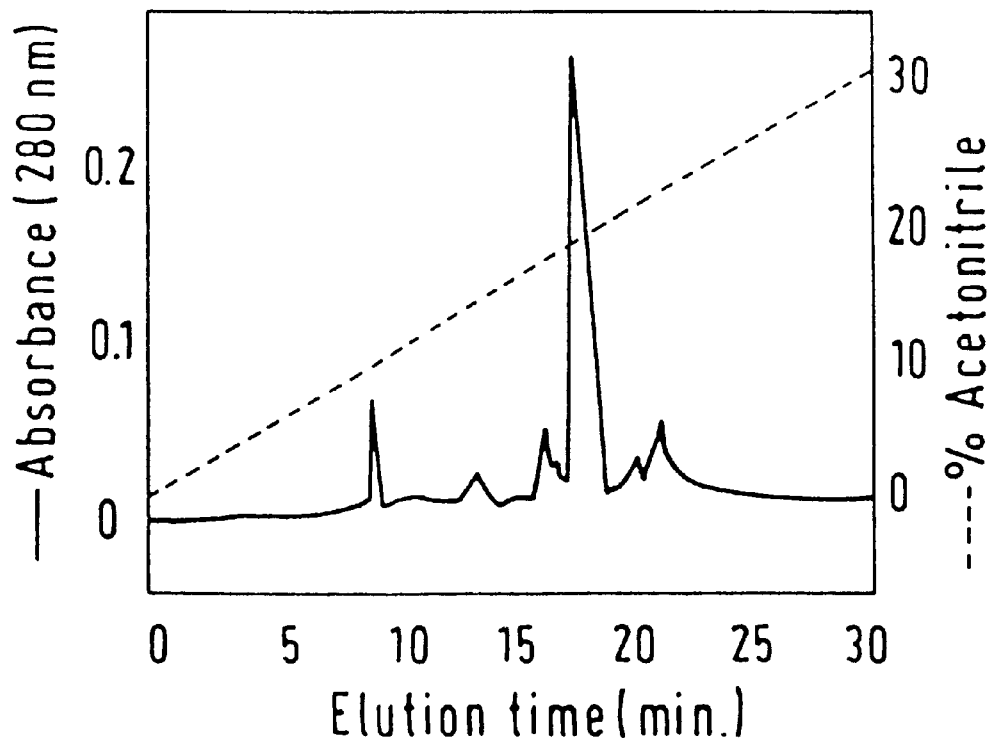

Active fractions were pooled for each peak and further purified on reverse-phase HPLC as described in Example 7. Results for peak 1 are shown in FIGS. 19A and 19B: it yielded an active factor eluting at approximately 18% acetonitrile which is designated Ct-AMP1. Similarly peak 2 yielded an active factor eluting at approximately 18% acetonitrile which is designated Ct-AMP2 (results shown in FIGS. 20A and 20B).

EXAMPLE 11
Molecular Structure of the Purified Antimicrobial Proteins.

The molecular structure of the purified antimicrobial proteins was further analysed. Sodium dodecyl sulphate polyacrylamide gel electrophoresis (SDS-PAGE) was performed on precast commercial gels (PhastGel High Density from Pharmacia) using a PhastSystem (Pharmacia) electrophoresis apparatus. The sample buffer contained 200 mM Tris-HCl (pH 8.3), 1% (w/v) SDS, 1 mM EDTA, 0.005% bromophenol blue and, unless otherwise stated, 1% (w/v) dithioerythritol (DTE). Proteins were fixed after electrophoresis in 12.5% glutaraldehyde and silver-stained according to Heukeshoven and Dernick (1985, Electrophoresis, 6, 103–112).

The Rs-AFPs were analysed by SDS-PAGE. After reduction with β-mercaptoethanol and modification of the cysteine residues by S-pyridylethylation, both Rs-AFP1 and Rs-AFP2 show single bands with an apparent molecular mass of about 5 kDa. After simple reduction without further cysteine derivatisation, the 5 kDa band is always accompanied by a 16 kDa band at variable yields, which may represent an oligomeric form of the 5 kDa protein resisted during electrophoresis. Unreduced Rs-AFP1 and Rs-AFP2 migrate as single bands of 20 kDa and 17 kDa, respectively. These results show that the native Rs-AFPs are oligomeric proteins, consisting of dimers, trimers or tetramers of the 5 kDa polypeptide. The oligomeric structure appears to be stabilised by disulphide linkages.

Unreduced Rs-AFP1, Rs-AFP1 reduced and S-pyridylethylated Rs-AFP2 were analyzed by SDS-PAGE. 200 ng of the proteins were separated on the gels. Myoglobin fragments were used as moleculaar weight markers. (Pharmacia) with the following sizes: 17 kDa, 14.5 kDa, 8 kDa, 6 kDa, and 2.5 kDa.

SDS-PAGE analysis of Rs-nsLTP after reduction with DTE yielded a single 9 kDa band. The unreduced Rs-nsLTP migrated as a single 18 kDa band. It appears therefore that Rs-nsLTP is a dimeric protein (2×9 kDa) stabilised by disulphide bridges.

Purified Rs-nsLTP, reduced and non-reduced, was analyzed by SDS-PAGE with molecular weight markers of myoglobin fragments described above.

Free cysteine thiol groups of the Rs-AFPs were assessed qualitatively as follows. Hundred µg amounts of reduced or unreduced proteins were dissolved in 6 M guanidinium-Cl containing 100 mM sodium phosphate buffer (pH 7) and 1 mM EDTA. The mixtures were allowed to react with 5,5'-dithionitrobenzoic acid and monitored for release of nitrothiobenzoate as described by Creighton (1989, Protein structure, a practical approach, 155–167). Reduction of the proteins was done by addition of Tris-HCl (pH 8.6) to 100 mM and dithioerythritol to 30 mM, followed by incubation at 45° C. for 1 hour. The proteins were separated from the excess reagents by reversed-phase chromatography on a $C_2/C_{18}$ silica column.

The unreduced Rs-AFPs did not contain free cysteine thiol groups, whereas the reduced proteins did, indicating that all cysteine residues participate in disulphide bonds.

The pI values of Rs-AFP1 and Rs-AFP2 were determined by isoelectric focusing and found to be higher than 10 for both proteins. Isoelectric focusing was performed on precast Immobiline Dry Strips (Pharmacia) rehydrated in 8 M urea, using marker proteins in the pI range from 4.7 to 10.6 (Pharmacia).

When reduced with DTT, two purified proteins from Dahlia and two purified proteins from Cnicus run as ⅚KDa bands upon SDS-PAGE analysis. In their unreduced form, the purified proteins run as oligomers. Unreduced Dm-AMP1 runs as a 24 kDa protein and Dm-AMP2 as a 17 kDa protein. Similarly, unreduced Cb-AMP1 runs as a single band of 30 kDa and Cb-AMP2 as a band of 18 kDa. When reduced with DTT, SDS-PAGE analysis of three proteins (two proteins purified from Clitoria and one protein purified from Lathyrus) run as 5/6 kDa bands. In their unreduced form, the purified proteins run as oligomers. unreduced Ct-AMP1 and Ct-AMP2 run as proteins of approximately 15 kDa whereas unreduced Lc-AFP runs as an approximately 12 kDa protein.

EXAMPLE 12
Amino Acid Sequencing of the Rs-AFPs and Related Proteins.

Cysteine residues of the antifungal proteins were modified by S-pyridylethylation using the method of Fullmer (1984, Anal Biochem, 142, 336–341). Reagents were removed by HPLC on a Pep-S (porous silica $C_2/C_{18}$) (Pharmacia) column (25×0.4 cm). The S-pyridylethylated proteins were recovered from the column with a linear gradient from 0.1% trifluoroacetic acid (TFA) to acetonitrile containing 0.1% TFA. The resulting protein fractions were subjected to amino acid sequence analysis in a 477A Protein Sequencer (Applied Biosystems) with on-line detection of phenylthiohydantoin amino acid derivatives in a 120A Analyser (Applied Biosystems). Where necessary due to the proteins being blocked, treatment of the S-pyridylethylated proteins with pyroglutamate amino peptidase was done according to the supplier's instructions (Boehringer Mannheim, Mannheim, FRG).

The N-terminal amino acid sequence of Rs-AFP1 and Rs-AFP2 was determined by automated Edman degradation, after treatment with pyroglutamate amino peptidase which cleaves off cyclic N-terminal glutamate residues. FIG. 21 shows the sequence of the first 44 N-terminal amino acids of Rs-AFP1 and of the first 35 residues of Rs-AFP2. The sequences of Rs-AFP1 and Rs-AFP2 differ at only two positions within the first 36 residues. The replacement of a glutamic acid by a glutamine (position 4) and an asparagine by an arginine (position 27) in Rs-AFP2 are consistent with the higher net positive charge of this protein relative to Rs-AFP1, which was previously evidenced by cathodic gel electrophoresis and cation exchange chromatography (FIG. 1). Rs-AFP1 appears to be rich in cysteine and basic amino acids (5 and 9 respectively within the first 45 residues). The molecular mass of Rs-AFP1 calculated on the basis of the partial amino acid sequence (4964 Da) is very close to the value estimated by SDS-PAGE (about 5000 Da) which indicates that the determined sequence encompasses the major part of the protein. However, it is anticipated that Rs-AFP1 contains at least one more cysteine, since the absence of free thiol groups assumes an even number of cysteines.

FIG. 21 also shows the first 23 to 30 N-terminal amino acids of the Rs-AFP-like proteins isolated from other Brassicaceae as described in Example 5 (Bn-AFP1, Bn-AFP2, Br-AFP1, Br-AFP2, Sa-AFP1, Sa-AFP2, At-AFP1). All proteins were treated with pyroglutamate amino peptidase prior to sequencing but the cysteine residues were not modified. Consequently, cysteine residues appear as blanks upon Edman degradation. Amino acids identical to the corresponding amino acids in Rs-AFP1 are shown by dots. It appears therefore that the Rs-AFP-like proteins from other members of the family Brassicaceae are identical or nearly identical to Rs-AFP1 and Rs-AFP2. Br-AFP2 contains an unidentified uncommon amino acid at position 11.

FIG. 22 shows the complete amino acid sequence for the peptides Dm-AMP1, Cb-AMP1 and Cb-AMP2. Shown also is the sequence for the first 20 N-terminal amino acids of Dm-AMP2. The sequences for Dm-AMP1 and Dm-AMP2 differ at only one position (position 2) in these first 20 amino acids. Comparing the sequences for Cb-AMP1 and Cb-AMP2, there are three changes. The substitution of an acidic residue (aspartic acid at position 22) in Cb-AMP1 for a neutral asparagine in Cb-AMP2 and the substitution of glutamine at position 23 for a basic lysine are consistent with the higher net positive charge. Similarly, Cb-AMP2 also differs from Dm-AMP1 at two positions although the result is the net gain of two positive charges.

All four proteins show striking similarity to the proteins isolated from seeds of the Brassicaceae family. Alignment of the amino acid sequence for Rs-AFP1 (*Raphanus Sativus*— Antifungal Protein 1) with the sequence for Dm-AMP1 reveals that they have approximately 50% identical residues.

FIG. 23 shows the complete amino acid sequence for the peptides Lc-AFP and Ct-AMP1. Ct-AMP2 is expected to be highly homologous to Ct-AMP1. Both Lc-AFP and Ct-AMP1 are also homologous to the Compositae and Brassicaceae proteins. In particular Ct-AMP1 is very homologous to the Dahlia peptide Dm-AMP1, having 35 identical residues in its sequence.

Homologies can be found between this group of closely related proteins and the products encoded by two pea (*Pisum sativum*) genes, pI39 and pI230, which are specifically induced by the fungus *Fusarium solani* (Chiang and Hadwiger, 1991, Mol Plant Microbe Interact, 4, 324–331), and with the protein product of potato (*Solanum tuberosum*) gene p322 (Stiekema et al, 1988, Plant Mol Biol, 11, 255–269). Nothing is known about the biological properties of the proteins encoded by genes pI39, pI230 or p322. In addition, the Rs-AFP-like/Dahlia/Cnicus/Lathyrus/Clitoria class of antimicrobial proteins show homology to inhibitors of insect gut α-amylases from *Sorghum bicolor* (Bloch and Richardson, 1991, FEBS Lett, 279, 101–104), and also to γ-purothionins from *Triticum aestivum* (Colilla et al, 1990, FEBS Lett, 270, 191–194) which inhibit in vitro protein synthesis in cell-free systems (Mendez et al, 1990, Eur J Biochem, 194, 533–539).

Figures 3, 24:
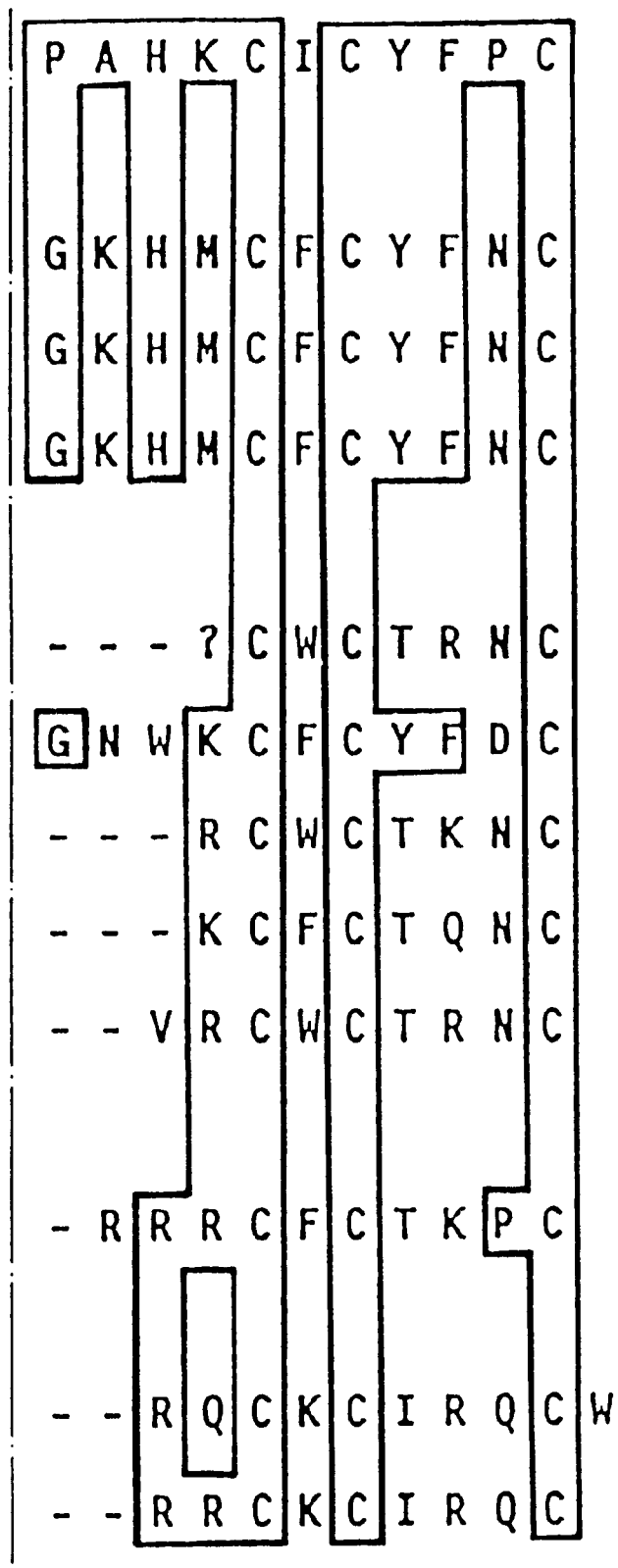

FIGS. 24-1, 24-2 and 24-2 show the alignment of the amino acid sequences of Rs-AFP1, Dm-AMP1, the Cb-AMPs, Lc-AFP, Ct-AMP1, the sorghum α-amylase inhibitor SIα2, wheat γ1 purothionin, and the predicted sequences of the mature protein products of the Fusarium-induced pea genes pI230 and pI39, of the cowpea gene pSAS10, and of the potato gene p322. Sequence identities and conserved changes compared with Rs-AFP1 are boxed. Conserved changes are considered as substitutions within the amino acid homology groups FWY, MILV, RHK, EDNQ, and PAGST. Gaps introduced for optimal alignment are represented by dashes.

Upon alignment of the sequences, all of the cysteines and most of the glycines appear at conserved positions, suggesting their importance with respect to structure and function of these proteins. Also noteworthy are the conserved aromatic residues at positions 11 and 40.

FIGS. 25A-1 and 25A-2 show one of the possible DNA sequences of the genes encoding Dm-AMP1, Dm-AMP2, Cb-AMP1 and Cb-AMP2. Similarly FIG. 25B shows one of the possible DNA sequences of the genes encoding Lc-AFP and Ct-AMP1. These gene sequences have been predicted from the known amino acid sequences using codons which commonly occur in dicotyledonous plants. The actual gene sequences within the seed may differ due to the degeneracy of the genetic code.

EXAMPLE 13
Amino Acid Sequencing of Rs-nSLTP.

Amino acid sequencing of the Rs-nsLTP protein was carried out according to the description in Example 12.

FIG. 26 shows the first 43 N-terminal amino acids of Rs-nsLTP of which the cysteine residues were modified by S-pyridylethylation. In FIGS. 27-1 and 27-2 the sequence of Rs-nsLTP is aligned with the N-terminal sequences of non-specific lipid transfer proteins isolated from *Spinacia oleracea* (So-nsLTP; Bernhard et al, 1990, Plant Physiol, 95, 164–170), *Ricinus communis* (Rc-nsLTP; Takishima et al, 1986, Biochim Biophys Acta, 870, 248–255), *Daucus carota* (Dc-nsLTP; Stenk et al, 1991, Plant Cell, 9, 907–921), *Hordeum vulgare* (Hv-nsLTP; Bernhard and Somerville, 1989, Arch Biochem Biophys, 269, 695–697), and *Zea mays* (Zm-nsLTP; Tchang et al, 1988, J Biol Chem, 263, 16849–16855). Gaps introduced for optimal alignment of the sequences are indicated by dashes. Identical amino acids and conserved substitutions occurring in at least 4 of the 6 sequences are boxed. Conserved changes are considered as substitutions within the amino acid homology groups FWY, MILV, RHK, EDNQ and PAGST. Rs-nsLTP shows 38 to 53% sequence identity with the non-specific lipid transport proteins from other plant sources. Non-specific lipid transport proteins are proteins that can translocate phospholipids or other apolar compounds between two membrane systems. These proteins were previously thought to play a role in the transport of phospholipids from endoplasmic reticulum to cell and organelle membranes (Arondel and Kaden, 1990, Experientia, 46, 579–585). However, recent evidence shows that nsLTPs are located extra-cellularly, making their proposed function in membrane biogenesis unlikely (Sterk et al, 1991, Plant Cell, 3, 907–921).

EXAMPLE 14
Stability of the Proteins' antifungal Activity.

Tests for antifungal activity were performed with 20 μl samples diluted five-fold with growth medium containing *Fusarium culmorum* spores, according to the assay method given in Example 1. Untreated control samples consisted of the test proteins at 500 μg/ml in 10 mM sodium phosphate buffer (pH 7). Heat stability tests were performed by heating aliquots of the test proteins for 10 minutes at different temperatures up to 100° C. Reduction of disulphide bridges was done by addition of dithiothreitol at 30 mM and Tris-HCl (pH 8.6) at 300 mM. The reagents were removed by reversed-phase chromatography. For digestions, different proteases were added at 100 μg/ml and incubated at 37° C. for 16 hours. The control treatment containing only the reagents proved negative for antifungal activity after the reversed-phase chromatography step.

The antifungal activity of all the purified proteins tested was resistant to heat treatments at up to 100° C. for 10 minutes. Reduction of their disulphide bonds by dithiothreitol, however, completely abolished the antifungal activity. These disulphide linkages are essential for biological activity. Treatment of the Rs-AFP proteins with trypsin, chymotrypsin, proteinase K or pronase E reduced the antifungal activity by at least 10-fold.

EXAMPLE 15
Antifungal Potency of the Proteins.

The antifungal potency of the purified proteins was assessed on different plant pathogenic fungi, using the assay described in Example 1. Growth of fungi, collection and harvest of fungal spores, and preparation of mycelial fragments were done as previously described (Broekaert et al, 1990, FEMS Microbiol Lett, 69:55–60). The following fungal strains were used: *Alternaria brassicola* MUCL 20297, *Ascochyta pisi* MUCL 30164, *Botrytis cinerea* MUCL 30158, *Cercospora beticola* strain K897, *Cladosporium sphaerosperum* (K0791), *Colletotrichum lindemuthianum* MUCL 9577, *Fusarium culmorum* IMI 180420, *Fusarium oxysporum* f.sp. *pisi* IMI 236441, *Fusarium oxysporum* f.sp. *lycopersici* MUCL 909, *Mycosphaerella fijiensis* var *fijiensis* IMI 105378, Nectria haematococca Collection Van Etten 160-2-2, *Penicillium digitatum* (K0879), *Phoma betae* MUCL 9916, *Pyrenophora tritici-repentis* MUCL 30217, *Pyricularia oryzae* MUCL 30166, *Rhizoctonia solani* CBS 207–84, *Sclerotinia sclerotianum* MUCL 30163, *Septoria nodorum* MUCL 30111, *Septoria tritici* (K1097D), *Trichoderma hamatum* MUCL 29736, *Trichoderma viride* (K1127), *Verticillium albo-atrum* (K0937), *Verticillium dahliae* MUCL 19210, *Venturia inaequalis* MUCL 15927.

For *C beticola, R solani, S sclerotianum, S nodorum* and *M fijiensis*, mycelial fragments were used as inoculum, whereas all other fungi were inoculated as spores.

Serial dilutions of the antifungal proteins were applied to the fungi, either using growth medium A or medium B. The percent growth inhibition was measured by microspectrophotometry. The concentration required for 50% growth inhibition after 48 h of incubation ($IC_{50}$ value) was calculated from the dose-reponse curves. The $IC_{50}$ values for the slow growing fungi *S nodorum* and *V inaequalis* was measured after 5 and 15 days of incubation respectively.

The results for Rs-AFP1 and Rs-AFP2 are summarised in Table 1.

TABLE 1

| ANTIFUNGAL ACTIVITY of Rs-AFP1 and Rs-AFP2 | | | | |
|---|---|---|---|---|
| | $IC_{50}$ (μg/ml) | | | |
| | Medium A | | Medium B | |
| Fungus | Rs-AFP1 | Rs-AFP2 | Rs-AFP1 | Rs-AFP2 |
| A brassicola | 15 | 2 | >100 | 20 |
| A pisi | 5 | 4 | >100 | 50 |
| B cinerea | 8 | 2 | >100 | >100 |

TABLE 1-continued

ANTIFUNGAL ACTIVITY of Rs-AFP1 and Rs-AFP2

| | IC$_{50}$ ($\mu$g/ml) | | | |
|---|---|---|---|---|
| | Medium A | | Medium B | |
| Fungus | Rs-AFP1 | Rs-AFP2 | Rs-AFP1 | Rs-AFP2 |
| C beticola | 2 | 2 | 100 | 3 |
| C lindemuthianum | 100 | 3 | >100 | >100 |
| F culmorum | 12 | 2 | 70 | 5 |
| F oxysporum pisi | 30 | 2 | >100 | >100 |
| F oxysporum lycopersici | 15 | 2 | >100 | >100 |
| M fijiensis | 4 | 1.5 | 30 | 10 |
| N haematococca | 6 | 2 | >100 | 30 |
| P betae | 2 | 1 | 20 | 6 |
| P tritici-repentis | 3 | 1.5 | 30 | 7 |
| P oryzae | 0.3 | 0.4 | >100 | 7 |
| R solani | 100 | >100 | >100 | >100 |
| S sclerotianum | 20 | >100 | >100 | >100 |
| S nodorum | 20 | 15 | 100 | 20 |
| T hamatum | 2 | 2 | 20 | 4 |
| V dahliae | 5 | 1.5 | >100 | 50 |

$\mu$g/ml, whereas Rs-AFP2 is inhibitory on 11 out of 18 fungi at this concentration. For some fungi, such as *F culmorum* and *C beticola*, the IC$_{50}$ value of Rs-AFP2 measured in medium A is comparable to that obtained in medium B. On other fungi, such as *F oxysporum* f.sp. pisi, the IC$_{50}$ value of Rs-AFP2 is increased from 2 $\mu$g/ml in medium A to over 100 $\mu$g/ml in medium B.

The antifungal potency of the Rs-AFP-like proteins from *B napus, rapa, S alba* and *A thaliana* was compared to that of Rs-AFP1 and Rs-AFP2 using five different test fungi. The results of these experiments are shown in Table 2. With the exception of Br-AFP2, all proteins had specific activities comparable to that of the Rs-AFPs. The fact that Br-AFP2 is on average 20-fold less active than the related species may be related to the observation that Br-AFP2 has an uncommon amino acid at position 11 (see FIG. 21) whereas the Rs-AFPs and related proteins all have an aromatic residue at this position (see FIGS. 24-1, 24-2 and 24-3). When tested in medium B, Rs-AFP2 appears to be the most potent protein, especially on the fungus *F culmorum*.

TABLE 2

Antifungal Activity of Rs-AFP-like proteins from *Brassica rapa, Brassica napus, Sinapis alba* and *Arabidopsis thaliana*

| Fungus | Rs-AFP1 | Rs-AFP2 | Br-AFP1 | Br-AFP2 | Bn-AFP1 | Bn-AFP2 | Sa-AFP1 | Sa-AFP2 | At-AFP1 |
|---|---|---|---|---|---|---|---|---|---|
| IC$_{50}$ ($\mu$g/ml) in medium A | | | | | | | | | |
| A brassicola | 15 | 2 | 3 | 75 | 0.60 | 1.20 | 1.2 | 4.5 | 10 |
| B cinerea | 8 | 2 | 1.50 | >100 | 2 | 2 | 1.8 | 3.5 | 3.90 |
| F culmorum | 12 | 2 | 2 | 38 | 2.80 | 2.10 | 4 | 2.3 | 3 |
| F oxysporum lycopersici | 15 | 2 | 1.80 | 42 | 1.30 | 1.50 | 6 | 2.3 | 3 |
| P oryzae | 0.3 | 0.4 | 0.25 | 3 | 0.35 | 0.25 | 0.5 | 0.3 | 0.25 |
| V dahliae | 5 | 1.5 | 0.80 | 15 | 1.20 | 1 | 1.5 | 1.2 | 1.50 |
| IC$_{50}$ ($\mu$g/ml) in medium B | | | | | | | | | |
| A brassicola | >100 | 20 | >100 | >100 | >100 | >100 | >100 | >100 | >100 |
| B cinerea | >100 | >100 | >100 | >100 | >100 | >100 | >100 | >100 | >100 |
| F culmorum | 70 | 5 | 19 | 32 | 33 | 40 | 40 | 32 | 35 |
| F oxysporum lycopersici | >100 | >100 | >100 | >100 | >100 | >100 | >100 | >100 | >100 |
| P oryzae | >100 | 7 | >100 | >100 | 32 | 8 | 25 | 3.8 | >100 |
| V dahliae | >100 | 50 | >100 | >100 | >100 | >100 | >100 | >100 | >100 |

TABLE 1-continued

ANTIFUNGAL ACTIVITY of Rs-AFP1 and Rs-AFP2

| | IC$_{50}$ ($\mu$g/ml) | | | |
|---|---|---|---|---|
| | Medium A | | Medium B | |
| Fungus | Rs-AFP1 | Rs-AFP2 | Rs-AFP1 | Rs-AFP2 |
| V inaequalis | ND | 25 | ND | >50 |

ND = not determined

The concentration of Rs-AFPs required for 50% growth inhibition in medium A varied from 0.3 $\mu$g/ml to over 100 $\mu$g/ml, depending on the test organism. The antifungal potency of Rs-AFP1 is generally slightly lower than that of Rs-AFP2 in medium A. The difference in antifungal potency between Rs-AFP1 and Rs-AFP2 is more pronounced for the tests performed in medium B. Rs-AFP1 only inhibits 4 out of 17 fungi by more than 50% at concentrations below 100

The antifungal potency of Rs-nsLTP is shown in Table 3. On most fungi Rs-nsLTP is 10 to 20 fold less potent relative to Rs-AFP2. Rs-nsLTP also appears to be highly salt-sensitive. None of the 13 fungi tested are inhibited by Rs-nsLTP in Medium B at concentrations below 100 $\mu$g/ml.

TABLE 3

Antifungal Activity of Rs-nsLTP

| | IC$_{50}$ ($\mu$g/ml) | |
|---|---|---|
| Fungus | Medium A | Medium B |
| A brassicola | 48 | 500 |
| A pisi | 41 | 700 |
| B cinerea | 45 | 680 |
| C lindemuthianum | 25 | >1000 |
| F culmorum | 20 | 520 |
| F oxysporum lycopersici | 54 | >1000 |
| F oxysporum pisi | 58 | 900 |

TABLE 3-continued

Antifungal Activity of Rs-nsLTP

| | IC$_{50}$ ($\mu$g/ml) | |
|---|---|---|
| Fungus | Medium A | Medium B |
| M fijiensis | >100 | >100 |
| N haematococca | 100 | >1000 |
| P betae | 18 | 750 |
| F oryzae | 10 | >1000 |
| T hamatum | 30 | >1000 |
| V dahliae | 7 | 135 |

The results for the Compositae proteins are summarised in Table 4.

The concentration of antimicrobial proteins required for 50% growth inhibition in medium A varied from 0.3 μg/ml to over 100 μg/ml, depending on the test organism. In general, the antifungal potency of the proteins was in the order: Cb-AMP 2>cb-AMP1>Dm-AMP1>Dm-AMP2. The differences in activity between the proteins is more pronounced in medium B, with Cb-AMP2 showing the best salt tolerance. Dm-AMP1 and Dm-AMP2 only inhibit the growth of 6 out of 11 fungi by more than 50% at concentrations below 100 μg/ml, whereas the two Cnicus proteins inhibit the growth of 7 out of 8 fungi when assayed in medium B.

Table 5 summarises the results for the antimicrobial proteins isolated from Leguminosae seeds.

These proteins are active, although their activity is somewhat lower than that of the Rs-AFPs and Compositae proteins, especially when assayed in high salt buffer, Medium B. In particular, the activity of Lc-AFP is markedly lower and comparable to the activity of Br-AFP2. The amino acid sequence of Lc-AFP also shows a substitution at position 11 which is normally tryptophan (FIGS. 21 and 23).

The high levels of antifungal activities demonstrated in vitro by each of the purified proteins suggest that they may play a role in the defence of seeds or seedlings against fungal attack.

TABLE 4

ANTIFUNGAL ACTIVITY of the Dm-AMPS and the Cb-AMPS

| | IC$_{50}$ ($\mu$g/ml) | | | | | | |
|---|---|---|---|---|---|---|---|
| | Medium A | | | | Medium B | | |
| FUNGUS | Dm-AMP1 | Dm-AMP2 | Cb-AMP1 | Cb-AMP2 | Dm-AMP1 | Dm-AMP2 | Cb-AMP1 |
| A brassicola | 1.1 | 2 | ND | ND | 140 | 140 | ND |
| B cinerea | 12 | 10 | 5 | 7 | >200 | >200 | 40 |
| C beticola | 1 | 3 | 1.2 | 1 | 6 | 6 | 5 |
| C sphaerospermum | 3 | 3 | 1 | 0.35 | 12 | 12 | 8 |
| F culmorum | 5 | 3 | 5 | 2 | 8 | 55 | 16 |
| F oxysporum pisi | 2.7 | 17 | ND | ND | >200 | >200 | ND |
| P digitatum | 2 | 2 | 2 | 1.4 | 70 | 50 | 15 |
| P oryzae | 5 | 6 | ND | ND | >200 | >200 | ND |
| S tritici | 1 | 0.5 | 0.8 | 0.5 | 4 | 2 | 2 |
| T viride | >80 | >80 | >100 | 40 | >100 | >100 | >100 |
| V albo-atrum | 4 | 2 | ND | ND | ND | ND | ND |
| V dahliae | 0.3 | 0.6 | 0.5 | 1.2 | 3 | 4 | 5 |

ND = not determined

TABLE 5

ANTIFUNGAL ACTIVITY of the Ct-AMPs and Lc-AFP

| | IC$_{50}$ ($\mu$g/ml) | | | | | |
|---|---|---|---|---|---|---|
| | Medium A | | | Medium B | | |
| FUNGUS | Ct-AMP1 | Ct-AMP2 | Lc-AFP | Ct-AMP1 | Ct-AMP2 | Lc-AFP |
| B cinerea | 37 | 15 | 80 | >150 | >150 | >200 |
| C sphaerospermum | 9 | 3 | 10 | >150 | 50 | >200 |
| F culmorum | 18 | 6 | 20 | 75 | 50 | >200 |
| P digitatum | >150 | >150 | 9 | >150 | >150 | >200 |
| P oryzae | >150 | >150 | >200 | >150 | >150 | >200 |
| S tritici | 9 | 2 | 37 | >150 | 60 | >200 |
| T viride | >150 | >150 | >200 | >150 | >150 | >200 |
| V albo-atrum | 9 | 3 | 37 | >150 | 100 | >200 |
| V dahliae | 2 | 1 | 20 | 40 | 12 | >200 |

EXAMPLE 16
Effect of Ions on Antifungal Activity.

The effect of ions on the antifungal activity of the Rs-AFPs and Rs-nsLTP was examined in more detail. The IC$_{50}$ values of Rs-AFP1, Rs-AFP2 and Rs-nsLTP on *F culmorum* and *T hamatum* were measured in five different media. The reference medium was the synthetic growth medium described in Example 1 which contains a total of 2.5 mM monovalent cations and 0.1 mM divalent cations. The four other media contained 10 mM KCl, 50 mM KCl, 1 mM CaCl$_2$ or 5 mM CaCl$_2$ in supplement, respectively. For the purpose of comparison, these tests were performed in parallel with β-purothionin, an antifungal protein from wheat seeds (isolated as described in Redman and Fisher, 1969, J Sci Food Agric, 20, 427–432) and Mj-AMP2, an antifungal protein from *Mirabilis jalapa* seeds (Cammue et al, 1992, J Biol Chem, 267, 2228–2233).

Table 6 shows the results of the antifungal activity assays in the presence of K$^+$ and Ca$^{2+}$.

Addition of KCl at up to 50 mM did not affect the antifungal activity of either Rs-AFP1 or Rs-AFP2. CaCl$_2$ at 1mM had no effect on Rs-AFP2 but increased the IC$_{50}$ value of Rs-AFP1 by about four-fold (ie, Ca$^{2+}$ reduced the antifungal activity of Rs-AFP1). CaCl$_2$ at 5 mM almost completely inactivated Rs-AFP1 while its effect on Rs-AFP2 varied from a slight increase in IC$_{50}$ for *F culmorum* to complete inactivation for *T hamatum*. Addition of KCl at 50 mM decreases the activity of Rs-nsLTP by more than 30-fold with both test fungi. In comparison, the IC$_{50}$ value of β-purothionin increased by about 7-fold in the presence of 5 mm CaCl$_2$. Mj-AMP2 appeared to be highly sensitive to the presence of salts, since its IC$_{50}$ values increased by about 10-fold upon addition of either 1 mM CaCl$_2$ or 50 mM KCl.

These results show that the Rs-AFPs are antagonised by divalent cations. Rs-AFP1 is much more sensitive to the presence of divalent cations than Rs-AFP2. Rs-nsLTP is clearly more salt-sensitive than either Rs-AFP1 or Rs-AFP2. The antagonistic effect of cations appears to be strongly dependent on the test organism.

EXAMPLE 17
Effect of the Purified Antimicrobial Proteins on the Growth of the Yeast, *Saccharomyces cerevisiae*.

The purified proteins were tested for their effect on *Saccharomyces cerevisiae*. The method used was similar to the antifungal assay described in Example 1 except that the growth medium was YPD (10 g/l yeast extract, 20 g/l bactopeptone, 20 g/l glucose) with 0.5% seaplaque agarose.

When assayed at levels of 250 μg/ml, none of the purified Brassicaceae proteins had an effect on the growth of *Saccharomyces cerevisiae* (strain Sp1). Similarly, Lc-AFP did not inhibit the growth of *S cerevisiae* (strain JRY188) at a concentration of 200 μg/ml.

The Compositae and Clitoria peptides were active against the growth of *S cerevisiae* (strain JRY188). These results are shown in Table 7. Of the six peptides, the two Clitoria peptides, Ct-AMP1 and Ct-AMP2 showed the highest level of activity.

TABLE 6

VARIATIONS IN ANTIFUNGAL ACTIVITY IN THE PRESENCE OF K$^+$ AND CA$^{2+}$

| | | IC$_{50}$ ($\mu$g/ml) | | | | |
|---|---|---|---|---|---|---|
| | Antifungal | Reference medium supplement: | | | | |
| Fungus | protein | None | 10 mM K$^+$ | 50 mM K$^+$ | 1 mM Ca$^{2+}$ | 5 mM Ca$^{2+}$ |
| F culmorum | Rs-AFP1 | 5 | 5 | 6 | 10 | 100 |
| | Rs-AFP2 | 3 | 2 | 2 | 2 | 5 |
| | Rs-nsLTP | 20 | 35 | >1000 | 108 | >1000 |
| | β-purothionin | 10 | 7 | 4 | 10 | 70 |
| | Mj-AMP2 | 4 | 5 | 40 | 50 | >100 |
| T hamatum | Rs-AFP1 | 7 | 7 | 7 | 30 | >100 |
| | Rs-AFP2 | 2 | 2 | 3 | 2 | >100 |
| | Rs-nsLTP | 30 | 60 | >1000 | >1000 | >1000 |
| | β-purothionin | 4 | 3 | 1.5 | 4 | 30 |
| | Mj-AMP2 | 2 | 2 | 25 | 20 | >100 |

TABLE 7

ACTIVITY OF Dm-AMPs, Cb-AMPs and Ct-AMPs on YEAST

| Protein | IC$_{50}$ ($\mu$g/ml) |
|---|---|
| Dm-AMP1 | 50 |
| Dm-AMP2 | 50 |
| Cb-AMP1 | 30 |
| Cb-AMP2 | 20 |
| Ct-AMP1 | 18 |
| Ct-AMP2 | 9 |

EXAMPLE 18
Effect of the Purified Antimicrobial Proteins on Bacteria.

The antibacterial effect of the purified proteins was assessed on *Agrobacterium tumefaciens* C58, *Alcaligenes eutrophus*, *Azospirillum brasilense* Sp7, *Bacillus megaterium* ATCC 13632, *Erwinia carotovora* strain 3912, *Escherichia coli* strain HB101, *Pseudomonas solanacearum* strain K60 and *Sarcina lutea* ATCC 9342, using the assay described in Example 1.

Rs-AFP2 caused 50% inhibition in *B megaterium* at 200 $\mu$g/ml, but had no effect on the other bacteria at concentrations up to 500 $\mu$g/ml.

The Compositae peptides Dm-AMP1, Dm-AMP2, Cb-AMP1 and Cb-AMP2 showed activity only on *B megaterium* where they inhibited growth to 50% at concentrations of 180, 40, 80 and 32 $\mu$g/ml respectively.

Rs-AFP1, Bn-AFPs, Br-AFP2, Sa-AFPs, Ct-AMPs and Lc-AFP had no effect on any of the bacteria at concentrations up to 500 $\mu$g/ml.

Results show that in general these proteins possess only weak antibacterial activity.

EXAMPLE 19
Effect of the Purified Antifungal Proteins on Cultured Human Cells.

Human cell toxicity assays were performed either on umbilical vein endothelial cells (Alessi et al, 1988, Eur J Biochem, 175, 531–540) or skin-muscle fibroblasts (Van Damme et al, 1987, Eur J Immunol, 17, 1–7) cultured in 96-well microplates. The growth medium was replaced by 80 $\mu$l of serum-free medium (Optimem 1 for endothelial cells or Eagle's minimal essential medium (EMEM) for fibroblasts, both from GIBCO), to which 20 $\mu$l of a filter-sterilised test solution was added. The cells were further incubated for 24 hours at 37° C. under a 5% CO$_2$ atmosphere with 100% relative humidity. The viability of the cells was assessed microscopically after staining with trypane blue (400 mg/l in phosphate buffered saline, PBS) for 10 minutes. Alternatively, cells were stained with neutral red (56 mg/l in PBS) for 2 hours at 37° C. Cells were lysed in acidic ethanol (100 mM sodium citrate, pH 4, containing 50% ethanol) and scored for release of the dye by microspectrophotometry at 540 nm.

The Rs-AFPs and Rs-nsLTP were evaluated for their potential toxic effects using this assay. When added at up to 500 $\mu$g/ml to either cultured human umbilical vein endothelial cells or human skin-muscle fibroblasts, neither Rs-AFP1, Rs-AFP2, nor Rs-nsLTP affected cell viability after 24 h of incubation. In contrast, β-purothionin administered at 50 $\mu$g/ml decreased the viability of both cell types by more than 90%.

EXAMPLE 20
Anti-fungal Activity of the Rs-AFPs Against Foliar Disease: in vivo test Rs-AFP2 was tested against the sugarbeet foliar disease *Cercospora beticola* (strain E897) using the following method.

Sugarbeet plants were grown in John Innes potting compost (No. 1 or 2 ) in 4cm diameter mini-pots. The protein preparation was formulated immediately prior to use by dissolving in sterile distilled water and diluting to the appropriate concentration. The formulation was applied to the plants as a foliar spray. The spray was applied to maximum discrete droplet retention. Plants were treated with the protein one day prior to inoculation with the disease which was applied as a foliar spray at a concentration of 50000 spores/ml. Plants were kept in an humidity chamber for 48 hours and then transferred to the glasshouse. Disease was assessed following a further incubation of 8 days.

Figure 28:
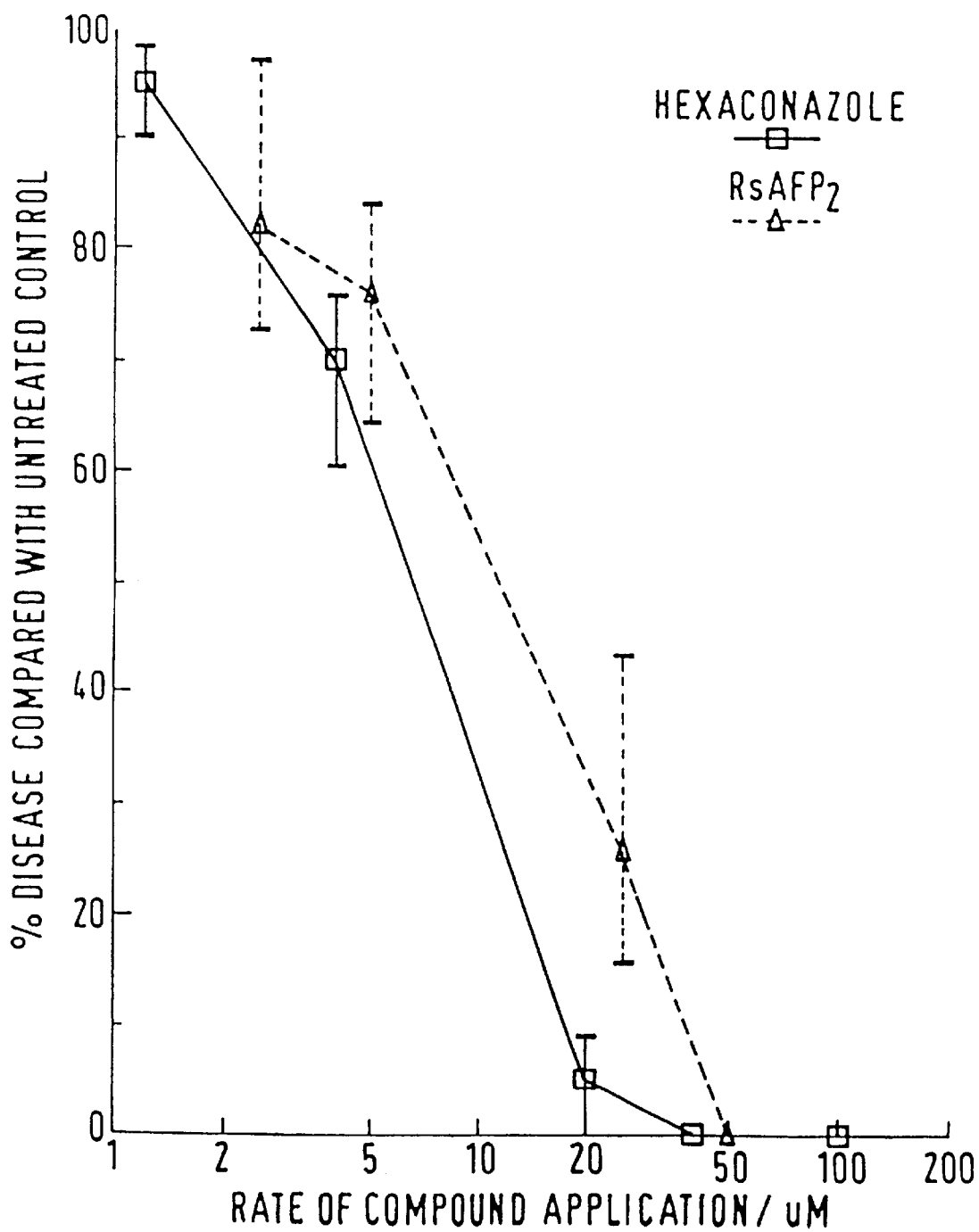
FIG. 28 is a graph of Rs-AFP2 in vivo activity.

Results are shown in FIG. 28. The commercially available fungicide hexaconazole was used as a standard. Rs-AFP2 gave good control of the disease and the concentration giving 50% control was approximately 15 $\mu$M. In comparison hexaconazole gave 50% disease control when applied at approximately 7 $\mu$M. This confirms that the protein can act as an effective fungicide in vivo and that its activity is on a molar basis comparable to the chemical standard.

EXAMPLE 21
Molecular Cloning of Rs-AFP1 and Rs-AFP2 cDNAs

From outdoor grown *Raphanus sativus* plants, seeds at 6 different developmental stages were collected, frozen in liquid nitrogen and stored at −800° C. After pulverisation, total RNA was extracted from 15 g of a mixture of the 6 different developmental stages, using the method of De Vries et al (1988, Plant Molecular Biology-Manual, B6, 1–13) with the exception that 6 ml of a 1:2 phenol:RNA extraction buffer mixture and 2 ml of chloroform were used per g of tissue. Poly (A)$^+$ mRNA was purified by affinity chromatography on oligo(dT)-cellulose as described by Siflow et al (1979, Biochemistry 18, 2725–2731) yielding about 10 $\mu$g of poly(A)$^+$ RNA per g of tissue. Double stranded cDNAs were prepared from 1,5 $\mu$g of poly(A)$^+$ RNA according to Gubler and Hoffman (1983, Gene 25, 263–269) and ligated to EcoRI/NotI adaptors using the cDNA Synthesis Kit of Pharmacia. The cDNAs were cloned into the lambda ZAPII phage vector (Stratagene) according to the manufacturers instructions. A DNA probe for screening the cDNA library was produced by polymerase chain reaction (PCR) as follows. Two degenerate oligonucleotides were synthesised:
OWB15 (5'AAAGAATTCAARYTNTGYSARMGNCC 3') and OWB17 (5'AAAGAATTCRTGNGCNGGRAANACRTARTTRC 3'). OWB15 corresponds to amino acids 2 to 7 of Rs-AFP1 and has a sense orientation. OWB17 corresponds to amino acids 36 to 43 of Rs-AFP1 and has an antisense orientation. Both primers have the AAAGAATTC (i.e. AAA followed by the EcoRI recognition sequence) sequence at their 5' ends. PCR was performed with the Taq polymerase under standard conditions (Sambrook et al, 1989, Molecular Cloning, Cold Spring Harbor Laboratory Press) using OWB15 and OWB17 as amplimers and 25 ng of cDNA as target DNA. The temperature programme included an initial step at 94° C. for 5 min, 30 cycles (94° C. for 1 min; 45° C. for 2 min, 72° C. for 3 min) and a final step at 72° C. for 10 min. The 144 bp PCR amplification product was purified on a 3% agarose (NuSieve, FMC) gel. This PCR product was partially reamplified using the sense degenerate oligonucleotide OWB16 (5'AAAGAATTCGGNACNTGGWSNGGNGTNTG 3') and OWB17. OWB16 also has the AAAGAATTC extension at its 5' end. This 123 bp PCR amplification product was again purified on a 3% agarose (NuSieve, FMC) gel and reamplified by PCR under the same conditions except that the reaction mixture contained 130 $\mu$M dTTP and 70 $\mu$M digoxigenin-11-dUTP instead of 200 $\mu$M dTTP. The digoxigenin-labeled PCR product was purified on a 3% NuSieve agarose gel. About 10,000 plaque forming units of the lambda ZAPII cDNA library were screened with the digoxigenin-labeled PCR product by in situ plaque hybridisation using nylon membranes (Hybond-N, Amersham). Membranes were air-dried and DNA was crosslinked to the membranes under UV light (0.15 J/cm$^2$). Hybridisation was performed for 16 h at 64° C. in 5×SSC, 1% blocking reagent (Boehringer Mannheim), 0.1% N-lauroylsarcosine, 0.02% sodium dodecylsulphate containing 10 ng/ml of heat denatured digoxigenin-labeled probe. Non-specifically bound probe was removed by rinsing two times 5 min in 2×SSC/ 0.1% SDS at 25° C. and two times 15 min in 0.1×SSC/0.1% SDS at 60° C. Detection of the probe was done using anti-digoxigenin antibodies linked to alkaline phosphatase (Boehringer Mannheim) and its substrate 5-bromo-4-chloro-3-indolyl phosphate (Boehringer Mannheim) according to the manufacturers instructions. Positive plaques were purified by two additional screening rounds with the same probe under the same conditions. Inserts from purified plaques were excised in vivo into the pBluescript phagemid form with the aid of the helper phage R408. The inserts from 22 different positive clones were excised by EcoRI digestion and their sizes compared by agarose gel electrophoresis. Four clones had an insert of approximately 400 bp, the other 18 positive clones contained inserts ranging between approximately 250 and 300 bp. The four clones with the 400 bp inserts and six clones with the smaller inserts were subjected to nucleotide sequence analysis. The clones with the largest insert all had an open reading frame of 80 amino acids corresponding to Rs-AFP1, as could be determined by comparison to the experimental N-terminal amino acid sequences (see Example 12). The 243 bp open reading frames code for the mature Rs-AFP1 (50 amino acids) preceded by a putative 29 amino acid signal sequence obeying the (−1,−3) rule (von Heijne 1985, Mol. Biol. 184, 99–105). These full-length cDNA clones only differed from each other in the length of their 5' and 3' end untranslated regions. Five of the clones with the smallest insert were partially identical to the full-length Rs-AFP1 cDNA clones except that they were truncated at their 5' ends. The remaining clone was identified as a 5' truncated Rs-AFP2 cDNA clone by comparing the deduced and the experimentally determined amino acid sequences. When comparing the full-length Rs-AFP1 cDNA clone pFRG1 (FIG. 29) and the truncated Rs-AFP2 cDNA clone pFRG2 (FIG. 30), it can be seen that the codon usage is slightly different and that the 3' end untranslated region of the Rs-AFP2 cDNA is longer than the one of the Rs-AFP1 cDNA. Finally, both the Rs-AFP1 and the Rs-AFP2 cDNA clones have at least two polyadenylation signals. FIG. 29 shows the nucleotide sequence and the deduced amino acid sequence of the full-length Rs-AFP1 cDNA clone pFRG1. The putative signal sequence is underlined and the sequence of the mature Rs-AFP1 is boxed. FIG. 30 shows the nucleotide sequence and the deduced amino acid sequence of the 5' truncated Rs-AFP2 cDNA clone pFRG2.

In order to obtain a full-length Rs-AFP2 cDNA, another approach was followed:PCR was performed under standard conditions using the antisense oligonucleotide OWB23 (5'ATAGAATTCGACGTGAGCTTATCATCTTATTATCCG 3') in combination with the M13 universal primer at one hand and the M13 reverse primer at the other hand. The last 30 nucleotides of OWB23 form the inverted complementary sequence of the part of the 3' untranslated region immediately flanking the poly-A tail of pFRG2 (see FIG. 30). This sequence is extended to the 5' end with the GAATTC EcoRI recognition site preceded by the nucleotides 'ATA'. As a template, either 2 μg of total cDNA or 10$^5$ recombinant phages were used. In both cases, 3 separate reactions were set up. Prior to amplification, phages were lysed by an initial step in the PCR temperature programme of 5 min at 99° C. to liberate the phage DNA. The size of the amplification products was determined by electrophoresis on a 3% agarose (NuSieve, FMC) gel. Products were obtained with sizes corresponding to inserts of 280 to 300 bp. Thus, it can be concluded that no full-length Rs-AFP2 cDNA clones seem to be present in the cDNA library.

EXAMPLE 22
Mutagenesis of Rs-AFP1 cDNA to Rs-AFP2 DNA

As can be deduced from the experimentally determined N-terminal sequences (see Example 12) and the nucleotide sequences (see Example 21), Rs-AFP1 and Rs-AFP2 only differ in two amino acids as stated in Example 12. As the antifungal potency of Rs-AFP2 is significantly higher than that of Rs AFP1 (see Table 1) and a full-length cDNA clone of the Rs-AFP2 is not available, the Rs-AFP1 cDNA was transformed into the Rs-AFP2 nucleotide sequence by PCR-assisted site-directed mutagenesis according to the method of E. Merino et al (1992, BioTechniques 12, 508–510). The following oligonucleotides were used:
OWB28 (5'CTTGGCCTTTGGCACAACTTC 3'),
OWB29 (5'GCTTTCTCAAGTCTAATGCAC 3'),
O W B 3 0
(5'AACTCGAGCTGCAGTGTCGACCTATTAACAA GGAAAGTAGC 3'),
O W B 3 5
(5'GGAATAGCCGATCGAGATCTAGGAAACAGCT ATGACCATG 3'),
OWB36 (5'GGAATAGCCGATCGAGATCTAGGA3').

The first mutation (glutamate into glutamine at position 5 of the mature protein) was introduced by performing PCR with the Pfu polymerase (Stratagene) using OWB35 (this is the M13 universal primer with a 5' tag sequence) and OWB28 (the first antisense mutagenesis primer) as amplimers and 100 ng of the KpnI-digested pFRG1 cDNA as target DNA. MgCl$_2$ was added to the amplification mixture to a final concentration of 50 mM. The temperature programme included an initial step at 94° C. for 5 min, 30 cycles (94° C. for 1 min, 45° C. for 2 min, 72° C. for 3 min) and a final step at 72° C. for 10 min. In a second step, this PCR product was used as a megaprimer and extended by the Pfu polymerase using 50 ng of the KpnI-digested pFRG1 cDNA as the target DNA. The temperature programme included an initial step at 94° C. for 5 min followed by a 5 cycles extension (94° C. for 1 min, 50° C. for 1 min, 72° C. for 1 min). Then OWB29 (the antisense primer introducing the second mutation, from asparagine to arginine at position 27 of the mature protein) and OWB36 (which is identical to the 5' tag sequence of OWB35) were added, followed by PCR amplification by the Pfu-polymerase as described for the introduction of the first mutation. To get a full-length Rs-AFP2 nucleotide sequence, the procedure outlined in the second step was repeated though using the oligonucleotide primers OWB36 and OWB30 (which introduces a second stop codon followed by the SalI, PstI and XhoI restriction sites, thus also eliminating the 3' end untranslated region of the Rs-AFP1 cDNA clone pFRG1). The final PCR product was cut with BamHI (occurring in the polylinker of the pBluescript phagemid pFRG1) and SalI, subcloned in pEMBL18+ (pre-digested with the same restriction enzymes) and subjected to nucleotide sequence analysis. FIGS. 31-1 and 31-2 show the nucleotide sequence and the derived amino acid sequence of the full-length Rs-AFP2 DNA clone pFRG4 obtained by PCR-assisted site-directed mutagenesis of the Rs-AFP1 cDNA clone pFRG1. The putative signal sequence is underlined and the sequence of the mature Rs-AFP2 is boxed.

EXAMPLE 23
Construction of the Expression Vector pFRG7

Figure 32:
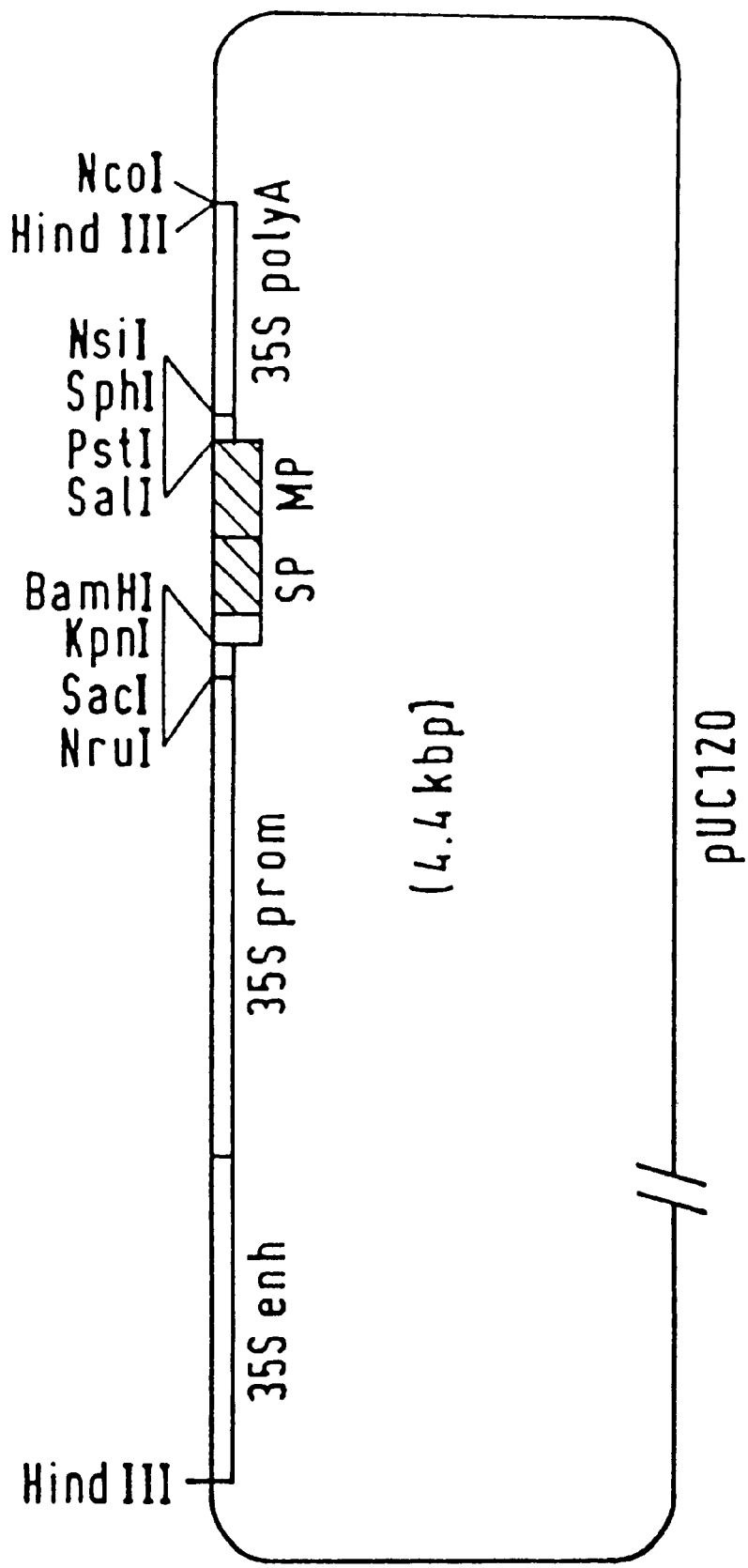
FIG. 32 shows the expression vector pFRG7.

The expression vector pFRG7 (FIG. 32; SP=signal peptide, MP=mature protein) contains the full coding region of the Rs-AFP2 DNA flanked at its 5' end by the strong constitutive promoter of the 35S RNA of the cauliflower mosaic virus (Odell et al, 1985, Nature 313, 810–812) with a duplicated enhancer element to allow for high transcriptional activity (Kay et al, 1987, Science 236, 1299–1302). The coding region of the Rs-AFP2 DNA is flanked at its 3' end side by the polyadenylation sequence of 35S RNA of the cauliflower mosaic virus (CaMV35S). The plasmid backbone of this vector is the phagemid pUC120 (Vieira and Messing 1987, Methods Enzymol. 153, 3–11). pFRG7 was constructed as follows clone pFRG4 which consisted of the Rs-AFP2 DNA (FIG. 37) cloned into the BamHI/SalI sites of pEMBL18+, Boehringer). The 298 bp BamHI/SalI fragment was subcloned into the expression vector pFAJ3002 which was pre-digested with BamHI and SalI. pFAJ3002 is a derivative of the expression vector pFF19 (Timmermans et al, 1990, J. Biotechnol. 14, 333–344) of which the unique EcoRI site is replaced by a HindIII site.

EXAMPLE 24
Construction of the Plant Transformation Vector pFRG8

Figure 33:
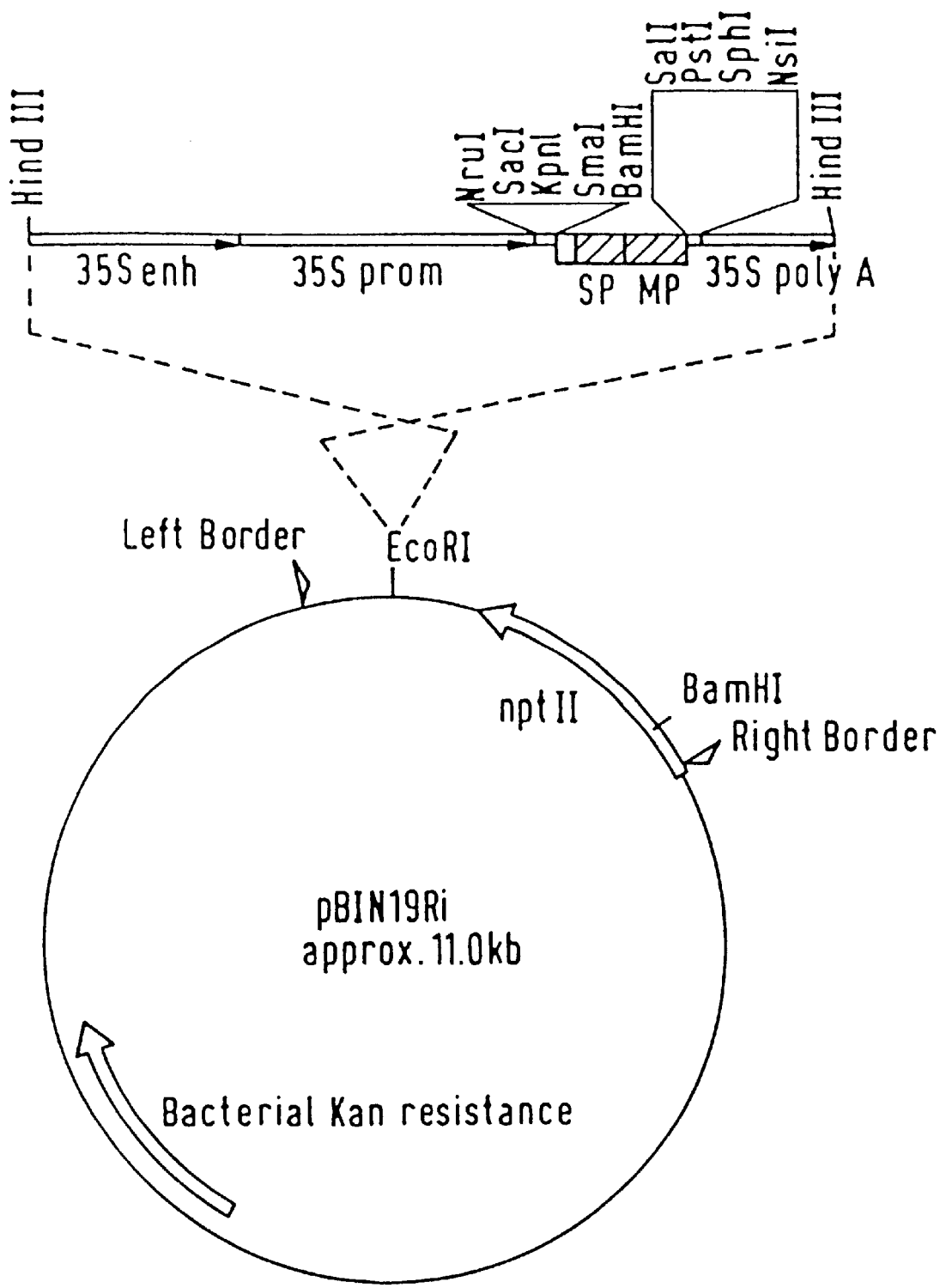
FIG. 33 shows the expression vector pFRG8.

The expression vector pFRG7 was digested with HindIII and the fragment containing the Rs-AFP2 DNA expression cassette was subcloned into the unique HindIII site of pBin19Ri. pBin19Ri is a modified version of the plant transformation vector pBin19 (Bevan 1984, Nucleic Acids Research 12, 8711–8721) wherein the unique EcoRI and HindIII sites are switched and the defective nptII expression cassette (Yenofsky et al. 1990, Proc. Natl. Acad. Sci. USA 87: 3435–3439) is introduced. The new plant transformation vector is designated pFRG8 (FIG. 33).

EXAMPLE 25
Plant Transformation

The disarmed *Agrobacterium tumefaciens* strain LBA4404 (pAL4404)(Hoekema et al, 1983, Nature 303, 179–180) was transformed with the vector pFRG8 using the method of de Framond et al (BioTechnology 1, 262–269).

Tobacco transformation was carried out using leaf discs of *Nicotiana tabacum* Samsun based on the method of Hdrsch et al (1985, Science 227, 1229–1231) and co-culturing with Agrobacterium strains containing pFRG8. Co-cultivation was carried out under selection pressure of 100 µg/ml kanamycin. Transgenic plants (transformed with pFRG8) were regenerated on media containing 100 µg/ml kanamycin. These transgenic plants may be analysed for expression of the newly introduced genes using standard western blotting techniques. Plants capable of constitutive expression of the introduced genes may be selected and self-pollinated to give seed. F1 seedlings of the transgenic plants may be further analysed.

What is claimed is:

1. An isolated antimicrobial protein having the amino acid sequence of amino acids 30–80 of SEQ ID NO: 49.

2. An isolated antimicrobial protein having the amino acid sequence of amino acids 30–80 of SEQ ID NO: 59.

* * * * *

SEQUENCE LISTING (1) GENERAL INFORMATION:

(iii) NUMBER OF SEQUENCES: 59

(2) INFORMATION FOR SEQ ID NO: 1:

(i) SEQUENCE CHARACTERISTICS:
      (A) LENGTH: 44 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Gln Lys Leu Cys Glu Arg Pro Ser Gly Thr Trp Ser Gly Val Cys Gl
1          5              10              15

Asn Asn Asn Ala Cys Lys Asn Gln Cys Ile Asn Leu Glu Lys Ala Ar
          20              25              30

His Gly Ser Cys Asn Tyr Val Phe Pro Ala His Lys
       35             40

(2) INFORMATION FOR SEQ ID NO: 2:

(i) SEQUENCE CHARACTERISTICS:
      (A) LENGTH: 36 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

Gln Lys Leu Cys Gln Arg Pro Ser Gly Thr Trp Ser Gly Val Cys Gl
1          5              10              15

```
Asn Asn Asn Ala Cys Lys Asn Gln Cys Ile Arg Leu Glu Lys Ala Ar
            20                  25                  30

His Gly Ser Cys
        35
```

(2) INFORMATION FOR SEQ ID NO: 3:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Gln Lys Leu Cys Glu Arg Pro Ser Gly Thr Trp Ser Gly Val Cys Gl
1               5                   10                  15

Asn Asn Asn Ala Cys Lys Asn Gln Cys Ile Asn
            20                  25
```

(2) INFORMATION FOR SEQ ID NO: 4:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Gln Lys Leu Cys Glu Arg Pro Ser Gly Thr Xaa Ser Gly Val Cys Gl
1               5                   10                  15

Asn Asn Asn Ala Cys Lys Asn Gln Cys Ile Arg
            20                  25
```

(2) INFORMATION FOR SEQ ID NO: 5:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Gln Lys Leu Cys Glu Arg Pro Ser Gly Thr Trp Ser Gly Val Cys Gl
1               5                   10                  15

Asn Asn Asn Ala Cys Lys Asn Gln Cys Ile Asn Leu Glu Lys
            20                  25                  30
```

(2) INFORMATION FOR SEQ ID NO: 6:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Gln Lys Leu Cys Glu Arg Pro Ser Gly Thr Trp Ser Gly Val Cys Gl
1               5                   10                  15
```

```
Asn Asn Asn Ala Cys Lys Asn
            20
```

(2) INFORMATION FOR SEQ ID NO: 7:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Gln Lys Leu Cys Glu Arg Pro Ser Gly Thr Trp Ser Gly Val Cys Gl
1               5                   10                  15
Asn Asn Asn Ala Cys Lys Asn Gln Cys
            20                  25
```

(2) INFORMATION FOR SEQ ID NO: 8:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Gln Lys Leu Cys Gln Arg Pro Ser Gly Thr Trp Ser Gly Val Cys Gl
1               5                   10                  15
Asn Asn Asn Ala Cys Arg Asn Gln Cys Ile
            20                  25
```

(2) INFORMATION FOR SEQ ID NO: 9:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Gln Lys Leu Cys Glu Arg Pro Ser Gly Thr Trp Ser Gly Val Cys Gl
1               5                   10                  15
Asn Ser Asn Ala Cys Lys Asn Gln Cys Ile Asn
            20                  25
```

(2) INFORMATION FOR SEQ ID NO: 10:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Glu Leu Cys Glu Lys Ala Ser Lys Thr Trp Ser Gly Asn Cys Gly As
1               5                   10                  15
Thr Gly His Cys Asp Asn Gln Cys Lys Ser Trp Glu Gly Ala Ala Hi
            20                  25                  30
```

```
Gly Ala Cys His Val Arg Asn Gly Lys His Met Cys Phe Cys Tyr Ph
        35                  40                  45

Asn Cys
    50

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Glu Val Cys Glu Lys Ala Ser Lys Thr Trp Ser Gly Asn Cys Gly As
1               5                   10                  15

Thr Gly His Cys
        20

(2) INFORMATION FOR SEQ ID NO: 12:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Glu Leu Cys Glu Lys Ala Ser Lys Thr Trp Ser Gly Asn Cys Gly As
1               5                   10                  15

Thr Lys His Cys Asp Asp Gln Cys Lys Ser Trp Glu Gly Ala Ala Hi
        20                  25                  30

Gly Ala Cys His Val Arg Asn Gly Lys His Met Cys Phe Cys Tyr Ph
        35                  40                  45

Asn Cys
    50

(2) INFORMATION FOR SEQ ID NO: 13:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Glu Leu Cys Glu Lys Ala Ser Lys Thr Trp Ser Gly Asn Cys Gly As
1               5                   10                  15

Thr Lys His Cys Asp Asn Lys Cys Lys Ser Trp Glu Gly Ala Ala Hi
        20                  25                  30

Gly Ala Cys His Val Arg Ser Gly Lys His Met Cys Phe Cys Tyr Ph
        35                  40                  45

Asn Cys
    50

(2) INFORMATION FOR SEQ ID NO: 14:
```

(i) SEQUENCE CHARACTERISTICS:
    (A) LENGTH: 47 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 14:

```
Lys Thr Cys Glu Asn Leu Ser Gly Thr Phe Lys Gly Pro Cys Ile Pr
1               5                   10                  15
Asp Gly Asn Cys Asn Lys His Cys Lys Asn Asn Glu His Leu Leu Se
            20                  25                  30
Gly Arg Cys Arg Asp Asp Phe Xaa Cys Trp Cys Thr Arg Asn Cys
        35                  40                  45
```

(2) INFORMATION FOR SEQ ID NO: 15:

(i) SEQUENCE CHARACTERISTICS:
    (A) LENGTH: 49 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 15:

```
Asn Leu Cys Glu Arg Ala Ser Leu Thr Trp Thr Gly Asn Cys Gly As
1               5                   10                  15
Thr Gly His Cys Asp Thr Gln Cys Arg Asn Trp Glu Ser Ala Lys Hi
            20                  25                  30
Gly Ala Cys His Lys Arg Gly Asn Trp Lys Cys Phe Cys Tyr Phe As
        35                  40                  45
Cys
```

(2) INFORMATION FOR SEQ ID NO: 16:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 16:

```
Met Ile Leu Val
1
```

(2) INFORMATION FOR SEQ ID NO: 17:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 17:

```
Glu Asp Asn Gln
1
```

(2) INFORMATION FOR SEQ ID NO: 18:

(i) SEQUENCE CHARACTERISTICS:

(A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Pro Ala Gly Ser Thr
1               5

(2) INFORMATION FOR SEQ ID NO: 19:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Gln Lys Leu Cys Glu Arg Pro Ser Gly Thr Trp Ser Gly Val Cys Gl
1               5                   10                  15

Asn Asn Asn Ala Cys Lys Asn Gln Cys Ile Asn Leu Glu Lys Ala Ar
                20                  25                  30

His Gly Ser Cys Asn Tyr Val Phe Pro Ala His Lys Cys Ile Cys Ty
            35                  40                  45

Phe Pro Cys
    50

(2) INFORMATION FOR SEQ ID NO: 20:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Glu Leu Cys Glu Lys Ala Ser Lys Thr Trp Ser Gly Asn Cys Gly As
1               5                   10                  15

Thr Gly His Cys Asp Asn Gln Cys Lys Ser Trp Glu Gly Ala Ala Hi
                20                  25                  30

Gly Ala Cys His Val Arg Asn Gly Lys His Met Cys Phe Cys Tyr Ph
            35                  40                  45

Asn Cys
    50

(2) INFORMATION FOR SEQ ID NO: 21:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Glu Leu Cys Glu Lys Ala Ser Lys Thr Trp Ser Gly Asn Cys Gly As
1               5                   10                  15

Thr Lys His Cys Asp Asp Gln Cys Lys Ser Trp Glu Gly Ala Ala Hi

```
                    20                  25                  30
Gly Ala Cys His Val Arg Asn Gly Lys His Met Cys Phe Cys Tyr Ph
            35                  40                  45
Asn Cys
    50

(2) INFORMATION FOR SEQ ID NO: 22:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Glu Leu Cys Glu Lys Ala Ser Lys Thr Trp Ser Gly Asn Cys Gly As
1               5                  10                  15
Thr Lys His Cys Asp Asn Lys Cys Lys Ser Trp Glu Gly Ala Ala Hi
            20                  25                  30
Gly Ala Cys His Val Arg Ser Gly Lys His Met Cys Phe Cys Tyr Ph
            35                  40                  45
Asn Cys
    50

(2) INFORMATION FOR SEQ ID NO: 23:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Lys Thr Cys Glu Asn Leu Ser Gly Thr Phe Lys Gly Pro Cys Ile Pr
1               5                  10                  15
Asp Gly Asn Cys Asn Lys His Cys Lys Asn Asn Glu His Leu Leu Se
            20                  25                  30
Gly Arg Cys Arg Asp Asp Phe Xaa Cys Trp Cys Thr Arg Asn Cys
            35                  40                  45

(2) INFORMATION FOR SEQ ID NO: 24:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Asn Leu Cys Glu Arg Ala Ser Leu Thr Trp Thr Gly Asn Cys Gly As
1               5                  10                  15
Thr Gly His Cys Asp Thr Gln Cys Arg Asn Trp Glu Ser Ala Lys Hi
            20                  25                  30
Gly Ala Cys His Lys Arg Gly Asn Trp Lys Cys Phe Cys Tyr Phe As
            35                  40                  45
Cys
```

(2) INFORMATION FOR SEQ ID NO: 25:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Asn Thr Cys Glu Asn Leu Ala Gly Ser Tyr Lys Gly Val Cys Phe Gl
1               5                   10                  15

Gly Cys Asp Arg His Cys Arg Thr Gln Glu Gly Ala Ile Ser Gly Ar
            20                  25                  30

Cys Arg Asp Asp Phe Arg Cys Trp Cys Thr Lys Asn Cys
            35                  40                  45

ATION FOR SEQ ID NO: 26:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Asn Thr Cys Glu His Leu Ala Asp Thr Tyr Arg Gly Val Cys Phe Th
1               5                   10                  15

Asn Ala Ser Cys Asp Asp His Cys Lys Asn Lys Ala His Leu Ile Se
            20                  25                  30

Gly Thr Cys His Asp Trp Lys Cys Phe Cys Thr Gln Asn Cys
            35                  40                  45

ATION FOR SEQ ID NO: 27:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Lys Thr Cys Glu Leu Asn Ala Asp Thr Tyr Arg Gly Pro Cys Phe Th
1               5                   10                  15

Thr Gly Ser Cys Asp Asp His Cys Lys Asn Lys Glu His Leu Leu Se
            20                  25                  30

Gly Arg Cys Arg Asp Asp Val Arg Cys Trp Cys Thr Arg Asn Cys
            35                  40                  45

ATION FOR SEQ ID NO: 28:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

```
Arg His Cys Glu Ser Leu Ser His Arg Phe Lys Gly Pro Cys Thr Ar
1               5                   10                  15

Asp Ser Asn Cys Ala Ser Val Cys Glu Thr Glu Arg Phe Ser Gly Gl
            20                  25                  30

Asn Cys His Gly Phe Arg Arg Arg Cys Phe Cys Thr Lys Pro Cys
        35                  40                  45
```

ATION FOR SEQ ID NO: 29:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

```
Arg Val Cys Met Gly Lys Ser Ala Gly Phe Lys Gly Leu Cys Met Ar
1               5                   10                  15

Asp Gln Asn Cys Ala Gln Val Cys Leu Gln Glu Gly Trp Gly Gly Gl
            20                  25                  30

Asn Cys Asp Gly Val Met Arg Gln Cys Lys Cys Ile Arg Gln Cys Tr
        35                  40                  45
```

ATION FOR SEQ ID NO: 30:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

```
Lys Ile Cys Arg Arg Arg Ser Ala Gly Phe Lys Gly Pro Cys Met Se
1               5                   10                  15

Asn Lys Asn Cys Ala Gln Val Cys Gln Gln Glu Gly Trp Gly Gly Gl
            20                  25                  30

Asn Cys Asp Gly Pro Phe Arg Arg Cys Lys Cys Ile Arg Gln Cys
        35                  40                  45
```

ATION FOR SEQ ID NO: 31:

(i) SEQUENCE CHARACTERISTICS:
        (A) LENGTH: 150 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 31:

```
GAGCTTTGCG AGAAGGCTTC TAAGACTTGG TCTGGAAACT GCGGAAACAC TGGACATTGC    60

GATAACCAAT GCAAGTCTTG GGAGGGAGCT GCTCATGGAG CTTGCCATGT TAGAAACGG    120

AAGCATATGT GCTTCTGCTA CTTCAACTGC                                    150
```

(2) INFORMATION FOR SEQ ID NO: 32:

(i) SEQUENCE CHARACTERISTICS:
        (A) LENGTH: 60 base pairs
        (B) TYPE: nucleic acid
        (C) STRANDEDNESS: both (D) TOPOLOGY: linear (ii) MOLECULE TYPE: cDNA (xi) SEQUENCE DESCRIPTION: SEQ ID NO: 32:

GAGGTTTGCG AGAAGGCTTC TAAGACTTGG TCTGGAAACT GCGGAAACAC TGGACATTGC      60

(2) INFORMATION FOR SEQ ID NO: 33:

(i) SEQUENCE CHARACTERISTICS:
        (A) LENGTH: 150 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 33:

GAGCTTTGCG AGAAGGCTTC TAAGACTTGG TCTGGAAACT GCGGAAACAC TAAGCATTGC      60

GATGATCAAT GCAAGTCTTG GGAGGGAGCT GCTCATGGAG CTTGCCATGT TAGAAACGG      120

AAGCATATGT GCTTCTGCTA CTTCAACTGC                                      150

(2) INFORMATION FOR SEQ ID NO: 34:

(i) SEQUENCE CHARACTERISTICS:
        (A) LENGTH: 150 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 34:

GAGCTTTGCG AGAAGGCTTC TAAGACTTGG TCTGGAAACT GCGGAAACAC TAAGCATTGC      60

GATAACAAGT GCAAGTCTTG GGAGGGAGCT GCTCATGGAG CTTGCCATGT TAGATCTGG      120

AAGCATATGT GCTTCTGCTA CTTCAACTGC                                      150

(2) INFORMATION FOR SEQ ID NO: 35:

(i) SEQUENCE CHARACTERISTICS:
        (A) LENGTH: 141 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 35:

AAGACTTGCG AGAACCTTTC TGGAACTTTC AAGGGACCAT GCATTCCAGA TGGAAACTGC      60

AACAAGCATT GCAAGAACAA CGAGCATCTT CTTTCTGGAA GATGCAGAGA TGATTTCNN     120

TGCTGGTGCA CTAGAAACTG C                                              141

(2) INFORMATION FOR SEQ ID NO: 36:

(i) SEQUENCE CHARACTERISTICS:
        (A) LENGTH: 147 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 36:

AACCTTTGCG AGAGAGCTTC TCTTACTTGG ACTGGAAACT GCGGAAACAC TGGACATTGC      60

```
GATACTCAAT GCAGAAACTG GGAGTCTGCT AAGCATGGAG CTTGCCATAA GAGAGGAAA      120

TGGAAGTGCT TCTGCTACTT CGATTGC                                         147
```

(2) INFORMATION FOR SEQ ID NO: 37:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Ala Leu Ser Cys Gly Thr Val Asn Ser Asn Leu Ala Ala Cys Ile Gl
1               5                   10                  15

Tyr Leu Thr Gln Asn Ala Pro Leu Ala Arg Gly Cys Cys Thr Gly Va
            20                  25                  30

Thr Asn Leu Asn Asn Met Ala Xaa Thr Thr Pro
        35                  40
```

(2) INFORMATION FOR SEQ ID NO: 38:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

```
Ala Leu Ser Cys Gly Thr Val Asn Ser Asn Leu Ala Ala Cys Ile Gl
1               5                   10                  15

Tyr Leu Thr Gln Asn Ala Pro Leu Ala Arg Gly Cys Cys Thr Gly Va
            20                  25                  30

Thr Asn Leu Asn Asn Met Ala Xaa Thr Thr Pro
        35                  40
```

(2) INFORMATION FOR SEQ ID NO: 39:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Gly Ile Thr Cys Gly Met Val Ser Ser Lys Leu Ala Pro Cys Ile Gl
1               5                   10                  15

Tyr Leu Lys Gly Gly Pro Leu Gly Gly Gly Ser Ser Gly Gly Ile Ly
            20                  25                  30

Ala Leu Asn Ala Ala Ala Ala Thr Thr Pro
        35                  40
```

(2) INFORMATION FOR SEQ ID NO: 40:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Val Asp Cys Gly Gln Val Asn Ser Ser Leu Ala Ser Cys Ile Pro Ph
1               5                   10                  15

Leu Thr Gly Gly Val Ala Ser Pro Ser Ala Ser Cys Cys Ala Gly Va
                20                  25                  30

Gln Asn Leu Lys Thr Leu Ala Pro Thr Ser Ala
            35                  40

(2) INFORMATION FOR SEQ ID NO: 41:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Val Leu Thr Cys Gly Gln Val Thr Gly Ala Leu Ala Pro Cys Leu Gl
1               5                   10                  15

Tyr Leu Arg Ser Gln Val Asn Val Pro Val Pro Leu Thr Cys Cys As
                20                  25                  30

Val Val Arg Gly Leu Asn Asn Ala Ala Arg Thr Thr Leu
            35                  40                  45

(2) INFORMATION FOR SEQ ID NO: 42:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Ala Leu Asn Cys Gly Gln Val Asp Ser Lys Asn Lys Pro Cys Leu Th
1               5                   10                  15

Tyr Val Gln Gly Gly Pro Gly Pro Ser Gly Leu Cys Cys Asn Gl
                20                  25                  30

Val Arg Asp Leu His Asn Gln Ala Gln Ser Ser Gly
            35                  40

(2) INFORMATION FOR SEQ ID NO: 43:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Ala Ile Ser Cys Gly Gln Val Ala Ser Ala Ile Ala Pro Cys Ile Se
1               5                   10                  15

Tyr Ala Arg Gly Gln Gly Ser Gly Pro Ser Ala Gly Cys Cys Ser Gl
                20                  25                  30

Val Arg Ser Leu Asn Asn Ala Ala Arg Thr Thr Ala
            35                  40

(2) INFORMATION FOR SEQ ID NO: 44:

(i) SEQUENCE CHARACTERISTICS:
       (A) LENGTH: 26 base pairs
       (B) TYPE: nucleic acid
       (C) STRANDEDNESS: both
       (D) TOPOLOGY: linear (ii) MOLECULE TYPE: cDNA (xi) SEQUENCE DESCRIPTION: SEQ ID NO: 44:

AAAGAATTCA ARYTNTGYSA RMGNCC                                   26

(2) INFORMATION FOR SEQ ID NO: 45:

(i) SEQUENCE CHARACTERISTICS:
       (A) LENGTH: 32 base pairs
       (B) TYPE: nucleic acid
       (C) STRANDEDNESS: both
       (D) TOPOLOGY: linear (ii) MOLECULE TYPE: cDNA (xi) SEQUENCE DESCRIPTION: SEQ ID NO: 45:

AAAGAATTCR TGNGCNGGRA ANACRTARTT RC                            32

(2) INFORMATION FOR SEQ ID NO: 46:

(i) SEQUENCE CHARACTERISTICS:
       (A) LENGTH: 29 base pairs
       (B) TYPE: nucleic acid
       (C) STRANDEDNESS: both
       (D) TOPOLOGY: linear (ii) MOLECULE TYPE: cDNA (xi) SEQUENCE DESCRIPTION: SEQ ID NO: 46:

AAAGAATTCG GNACNTGGWS NGGNGTNTG                                29

(2) INFORMATION FOR SEQ ID NO: 47:

(i) SEQUENCE CHARACTERISTICS:
       (A) LENGTH: 9 base pairs
       (B) TYPE: nucleic acid
       (C) STRANDEDNESS: both
       (D) TOPOLOGY: linear (ii) MOLECULE TYPE: cDNA (xi) SEQUENCE DESCRIPTION: SEQ ID NO: 47:

AAAGAATTC                                                      9

(2) INFORMATION FOR SEQ ID NO: 48:

(i) SEQUENCE CHARACTERISTICS:
       (A) LENGTH: 414 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 16..255

(xi) SEQUENCE DESCRIPTION: SEQ ID NO: 48:

GTTTTATTAG TGATC ATG GCT AAG TTT GCG TCC ATC ATC GCA CTT CTT TTT    51

```
                Met Ala Lys Phe Ala Ser Ile Ile Ala Leu Leu Phe
                  1               5                  10

GCT GCT CTT GTT CTT TTT GCT GCT TTC GAA GCA CCA ACA ATG GTG GAA         99
Ala Ala Leu Val Leu Phe Ala Ala Phe Glu Ala Pro Thr Met Val Glu
         15                  20                  25

GCA CAG AAG TTG TGC GAA AGG CCA AGT GGG ACA TGG TCA GGA GTC TGT        147
Ala Gln Lys Leu Cys Glu Arg Pro Ser Gly Thr Trp Ser Gly Val Cys
 30                  35                  40

GGA AAC AAT AAC GCA TGC AAG AAT CAG TGC ATT AAC CTT GAG AAA GCA        195
Gly Asn Asn Asn Ala Cys Lys Asn Gln Cys Ile Asn Leu Glu Lys Ala
 45                  50                  55                  60

CGA CAT GGA TCT TGC AAC TAT GTC TTC CCA GCT CAC AAG TGT ATC TGC        243
Arg His Gly Ser Cys Asn Tyr Val Phe Pro Ala His Lys Cys Ile Cys
                 65                  70                  75

TAC TTT CCT TGT TAATTTATCG CAAACTCTTT GGTGAATAGT TTTTATGTAA            295
Tyr Phe Pro Cys
             80

TTTACACAAA ATAAGTCAGT GTCACTATCC ATGAGTGATT TTAAGACATG TACCAGATA       355

GTTATGTTGG TTCGGTTATA CAAATAAAGT TTTATTCACC AAAAAAAAAA AAAAAAAA        414

(2) INFORMATION FOR SEQ ID NO: 49:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 49:

Met Ala Lys Phe Ala Ser Ile Ile Ala Leu Leu Phe Ala Ala Leu Val
  1               5                  10                  15

Leu Phe Ala Ala Phe Glu Ala Pro Thr Met Val Glu Ala Gln Lys Leu
                 20                  25                  30

Cys Glu Arg Pro Ser Gly Thr Trp Ser Gly Val Cys Gly Asn Asn Asn
                 35                  40                  45

Ala Cys Lys Asn Gln Cys Ile Asn Leu Glu Lys Ala Arg His Gly Ser
 50                  55                  60

Cys Asn Tyr Val Phe Pro Ala His Lys Cys Ile Cys Tyr Phe Pro Cys
 65                  70                  75                  80

(2) INFORMATION FOR SEQ ID NO: 50:

(i) SEQUENCE CHARACTERISTICS:
        (A) LENGTH: 284 base pairs
        (B) TYPE: nucleic acid
        (C) STRANDEDNESS: both
        (D) TOPOLOGY: linear (ii) MOLECULE TYPE: cDNA (ix) FEATURE:
         (A) NAME/KEY: CDS
         (B) LOCATION: 1..108

(xi) SEQUENCE DESCRIPTION: SEQ ID NO: 50:

GGA AAT AAT AAC GCA TGC AAG AAT CAG TGC ATT CGA CTT GAG AAA GCA         48
Gly Asn Asn Asn Ala Cys Lys Asn Gln Cys Ile Arg Leu Glu Lys Ala
  1               5                  10                  15

CGA CAT GGG TCT TGC AAC TAT GTC TTC CCA GCT CAC AAG TGT ATC TGT         96
Arg His Gly Ser Cys Asn Tyr Val Phe Pro Ala His Lys Cys Ile Cys
                 20                  25                  30
```

```
TAT TTC CCT TGT TAATTCCATA AACTCTTCGG TGGTTAATAG TGTGCGCATA          148
Tyr Phe Pro Cys
         35

TTACATATAA TTAATAAGTT TGTGTCACTA TTTATTAGTG ACTTTATGAC ATGTGCCAG     208

TATGTTTATG TTGGGTTGGT TGTAATATAA AAAAGTTCAC GGATAATAAG ATGATAAGC    268

CACGTCGCCA AAAAAA                                                   284
```

(2) INFORMATION FOR SEQ ID NO: 51:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO: 51:

```
Gly Asn Asn Asn Ala Cys Lys Asn Gln Cys Ile Arg Leu Glu Lys Ala
 1               5                  10                  15

Arg His Gly Ser Cys Asn Tyr Val Phe Pro Ala His Lys Cys Ile Cys
             20                  25                  30

Tyr Phe Pro Cys
         35
```

(2) INFORMATION FOR SEQ ID NO: 52:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 52:

```
ATAGAATTCG ACGTGAGCTT ATCATCTTAT TATCCG                              36
```

(2) INFORMATION FOR SEQ ID NO: 53:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 53:

```
CTTGGCCTTT GGCACAACTT C                                              21
```

(2) INFORMATION FOR SEQ ID NO: 54:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 54:

```
GCTTTCTCAA GTCTAATGCA C                                              21
```

(2) INFORMATION FOR SEQ ID NO: 55:

(i) SEQUENCE CHARACTERISTICS:
    (A) LENGTH: 41 base pairs
    (B) TYPE: nucleic acid
    (C) STRANDEDNESS: both
    (D) TOPOLOGY: linear (ii) MOLECULE TYPE: cDNA (xi) SEQUENCE DESCRIPTION: SEQ ID NO: 55:

AACTCGAGCT GCAGTGTCGA CCTATTAACA AGGAAAGTAG C                                41

(2) INFORMATION FOR SEQ ID NO: 56:

(i) SEQUENCE CHARACTERISTICS:
        (A) LENGTH: 40 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 56:

GGAATAGCCG ATCGAGATCT AGGAAACAGC TATGACCATG                                 40

(2) INFORMATION FOR SEQ ID NO: 57:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO: 57:

GGAATAGCCG ATCGAGATCT AGGA                                                  24

(2) INFORMATION FOR SEQ ID NO: 58:

(i) SEQUENCE CHARACTERISTICS:
        (A) LENGTH: 288 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 43..282

(xi) SEQUENCE DESCRIPTION: SEQ ID NO: 58:

```
CCCCGGGCTG CAGGAATTCG CGGCCGCGTT TTATTAGTGA TC ATG GCT AAG TTT              54
                                                Met Ala Lys Phe
                                                  1

GCG TCC ATC ATC GCA CTT CTT TTT GCT GCT CTT GTT CTT TTT GCT GCT            102
Ala Ser Ile Ile Ala Leu Leu Phe Ala Ala Leu Val Leu Phe Ala Ala
  5              10                  15                  20

TTC GAA GCA CCA ACA ATG GTG GAA GCA CAG AAG TTG TGC CAA AGG CCA            150
Phe Glu Ala Pro Thr Met Val Glu Ala Gln Lys Leu Cys Gln Arg Pro
              25                  30                  35

AGT GGG ACA TGG TCA GGA GTC TGT GGA AAC AAT AAC GCA TGC AAG AAT            198
Ser Gly Thr Trp Ser Gly Val Cys Gly Asn Asn Asn Ala Cys Lys Asn
          40                  45                  50

CAG TGC ATT AGA CTT GAG AAA GCA CGA CAT GGA TCT TGC AAC TAT GTC            246
Gln Cys Ile Arg Leu Glu Lys Ala Arg His Gly Ser Cys Asn Tyr Val
      55                  60                  65
```

```
TTC CCA GCT CAC AAG TGT ATC TGC TAC TTT CCT TGT TAATAG                    288
Phe Pro Ala His Lys Cys Ile Cys Tyr Phe Pro Cys
    70                  75                  80
```

(2) INFORMATION FOR SEQ ID NO: 59:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 59:

```
Met Ala Lys Phe Ala Ser Ile Ile Ala Leu Leu Phe Ala Ala Leu Val
 1               5                  10                  15

Leu Phe Ala Ala Phe Glu Ala Pro Thr Met Val Glu Ala Gln Lys Leu
                20                  25                  30

Cys Gln Arg Pro Ser Gly Thr Trp Ser Gly Val Cys Gly Asn Asn Asn
            35                  40                  45

Ala Cys Lys Asn Gln Cys Ile Arg Leu Glu Lys Ala Arg His Gly Ser
        50                  55                  60

Cys Asn Tyr Val Phe Pro Ala His Lys Cys Ile Cys Tyr Phe Pro Cys
65                  70                  75                  80
```